US012774495B2

(12) United States Patent
Bernstein et al.

(10) Patent No.: US 12,774,495 B2
(45) Date of Patent: Oct. 27, 2026

(54) LINEAGE INFERENCE FROM SINGLE-CELL TRANSCRIPTOMES

(71) Applicants: The General Hospital Corporation, Boston, MA (US); The Children's Medical Center Corporation, Boston, MA (US)

(72) Inventors: Bradley Bernstein, Boston, MA (US); Peter van Galen, Boston, MA (US); Tyler Miller, Boston, MA (US); Caleb Lareau, Boston, MA (US); Vijay Sankaran, Boston, MA (US)

(73) Assignees: The General Hospital Corporation; The Children's Medical Center Corporation

(*) Notice: Subject to any disclaimer, the term of this patent is extended or adjusted under 35 U.S.C. 154(b) by 468 days.

(21) Appl. No.: 16/944,943

(22) Filed: Jul. 31, 2020

(65) Prior Publication Data

US 2021/0032702 A1 Feb. 4, 2021

Related U.S. Application Data

(60) Provisional application No. 63/002,147, filed on Mar. 30, 2020, provisional application No. 62/881,148, filed on Jul. 31, 2019.

(51) Int. Cl.
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2600/112* (2013.01); *C12Q 2600/158* (2013.01)

(58) Field of Classification Search
CPC C12Q 1/6886; C12Q 1/686; C12Q 2600/112; C12Q 2600/158; C12Q 1/6806; C12Q 2600/156; C12Q 1/6881
See application file for complete search history.

(56) References Cited

U.S. PATENT DOCUMENTS

| | | | | |
|---|---|---|---|---|
| 5,843,728 | A | 12/1998 | Seed et al. | |
| 5,851,828 | A | 12/1998 | Seed et al. | |
| 5,912,170 | A | 6/1999 | Seed et al. | |
| 6,004,811 | A | 12/1999 | Seed et al. | |
| 6,284,240 | B1 | 9/2001 | Seed et al. | |
| 6,392,013 | B1 | 5/2002 | Seed et al. | |
| 6,410,014 | B1 | 6/2002 | Seed et al. | |
| 6,753,162 | B1 | 6/2004 | Seed et al. | |
| 8,211,422 | B2 | 7/2012 | Eshhar et al. | |
| 9,856,530 | B2* | 1/2018 | Hindson | C12Q 1/6855 |
| 10,221,436 | B2* | 3/2019 | Hardenbol | C12Q 1/6806 |
| 2009/0233292 | A1* | 9/2009 | Podini | C12Q 1/6876 435/6.12 |
| 2010/0029498 | A1 | 2/2010 | Gnirke et al. | |
| 2013/0260373 | A1* | 10/2013 | Kavlick | C12Q 1/6851 435/6.11 |
| 2014/0227705 | A1* | 8/2014 | Vogelstein | C12Q 1/6806 435/6.12 |
| 2016/0002623 | A1* | 1/2016 | Thiruvengadam | C12Q 1/6883 506/9 |
| 2016/0060691 | A1 | 3/2016 | Giresi et al. | |
| 2016/0208323 | A1 | 7/2016 | Bernstein et al. | |
| 2017/0227531 | A1* | 8/2017 | Ting | C12Q 1/6816 |

FOREIGN PATENT DOCUMENTS

| | | | | |
|---|---|---|---|---|
| CN | 104278022 | A * | 1/2015 | |
| KR | 20160013613 | A * | 2/2016 | A47K 5/12 |
| TW | 201028505 | * | 8/2010 | |
| WO | 92/15322 | A1 | 9/1992 | |
| WO | 2014/210353 | A2 | 12/2014 | |
| WO | 2016/040476 | A1 | 3/2016 | |
| WO | 2016/168584 | A1 | 10/2016 | |
| WO | WO-2017075294 | A1 * | 5/2017 | C12N 15/1075 |
| WO | 2017/156336 | A1 | 9/2017 | |
| WO | 2017/164936 | A1 | 9/2017 | |
| WO | 2019/084046 | A1 | 5/2019 | |
| WO | 2019/084055 | A1 | 5/2019 | |
| WO | 2019/094984 | A1 | 5/2019 | |

(Continued)

OTHER PUBLICATIONS

Illumina, Illumina Sequencing Technology, Oct. 21, 2013, YouTube, retrieved from https://www.youtube.com/watch?v=womKfikWIxM (Year: 2013).*v
Hamalainen et al., mtDNA Mutagenesis Disrupts Pluripotent Stem Cell Function by Altering Redox Signaling, 2015, Cell Reports, vol. 11, pp. 1614-1624 (Year: 2015).*
Lafzi et al., Tutorial: guidelines for the experimental design of single-cell RNA sequencing studies, 2018, Nature Protocols, vol. 13, pp. 2742-2757 (Year: 2018).*
Prigione et al., Human Induced Pluripotent Stem Cells Harbor Homoplasmic and Heteroplasmic Mitochondrial DNA Mutations While Maintaining Human Embryonic Stem Cell-like Metabolic Reprogramming, 2011, Stem Cells, vol. 29, pp. 1338-1348 (Year: 2011).*
Ziegenhain et al., Comparative Analysis of Single-Cell RNA Sequencing Methods, 2017, Molecular Cell, vol. 65, pp. 631-643 (Year: 2017).*

(Continued)

*Primary Examiner* — Jeffrey Stucker
*Assistant Examiner* — Brittney E Donoghue
(74) *Attorney, Agent, or Firm* — NIXON PEABODY LLP; David S. Resnick; Jeanne N. Jodoin

(57) ABSTRACT

Embodiments disclosed herein provide methods of using somatic mutations in mitochondrial genomes to retrospectively infer cell lineages in native contexts and to serve as genetic barcodes to measure clonal dynamics in complex cellular populations. Further, somatic mutations in mitochondrial DNA (mtDNA) are tracked by single cell genomic approaches for simultaneous analysis of single cell lineage and state. Applicants further show that mitochondrial mutations can be readily detected with contemporary single cell transcriptomic and epigenomic technologies to concomitantly capture gene expression profiles and chromatin accessibility, respectively.

21 Claims, 28 Drawing Sheets

Specification includes a Sequence Listing.

(56) References Cited

FOREIGN PATENT DOCUMENTS

| | | | |
|---|---|---|---|
| WO | 2019/241273 | A1 | 12/2019 |
| WO | 2020/077236 | A1 | 4/2020 |

OTHER PUBLICATIONS

Cohrt, Cell of the Month: CD34+ Cells, 2019, Tempo Bioscience (retrieved from: https://www.tempobioscience.com/cell-of-the-month-cd34-cells/) (Year: 2019).*

Samanthi, Difference Between Myeloid and Lymphoid Cells, 2017, Difference Between (retrieved from: https://www.differencebetween.com/difference-between-myeloid-and-vs-lymphoid-cells/) (Year: 2017).*

NIH , Somatic Cells, 2018, National Institute of Health, retrieved from (https://www.cancer.gov/publications/dictionaries/cancer-terms/def/somatic-cell) (Year: 2018).*

Haque et al., A practical guide to single-cell RNA-sequencing for biomedical research and clinical applications, 2017, Genome Medicine, vol. 9, Issue 75, pp. 1-12 (Year: 2017).*

Samanthi et al., Difference Between Myeloid and Lymphoid Cells, 2017, Difference Between (Year: 2017).*

Cravero et al., Biotinylated amplicon sequencing: A method for preserving DNA samples of limited quantity, 2018, Practical Laboratory Medicine 12, pp. e00108 1-e00108 10 (Year: 2018).*

Illumina, Illumina Sequencing Technology, Oct. 21, 2013, YouTube (Year: 2013).*

Schenk et al., Amplification of overlapping DNA amplicons in a single-tube multiplex PCR for targeted next-generation sequencing of BRCA1 and BRCA2, 2017, PLOS ONE, vol. 12, Issue 7, pp. 1-16 (Year: 2017).*

Cohrt, Cell of the Month: CD34+ Cells, 2019, Tempo Bioscience (Year: 2019).*

Chen et al., Precancerous Stem Cells Have Potential for both Benign and Malignant Differentiation, 2007, PLoS ONE, Issue 3, e293 1-16 (Year: 2007).*

Hopkins et al., Mutations in Mitochondrial DNA From Pancreatic Ductal Adenocarcinomas Associate With Survival Times of Patients and Accumulate as Tumors Progress, 2018, Gastroenterology, vol. 154, No. 6, pp. 1620-1624 (Year: 2018).*

Kang, et al., "Age-Related Accumulation of Somatic Mitochondrial DNA Mutations in Adult-Derived Human iPSCs", Cell Stem Cell, vol. 18, Issue 5, May 5, 2016, 13 pages.

Li, et al., "Extensive Tissue-related and Allele-related mtDNA Heteroplasmy Suggests Positive Selection for Somatic Mutations", Proceedings of the National Academy of Sciences of the United States of America, vol. 112, No. 8, Feb. 24, 2015, 2491-2496.

Ludwig, et al., "Lineage Tracing in Humans Enabled by Mitochondrial Mutations and Single-Cell Genomics", Cell, vol. 176, Mar. 7, 2019, 38 pages.

Nam, et al., "Somatic Mutations and Cell Identity Linked by Genotyping of Transcriptomes", Nature, vol. 571, Jul. 18, 2019, 22 pages.

Taylor, et al., "Mitochondrial DNA Mutations in Human Colonic Crypt Stem Cells", Journal of Clinical Investigation, vol. 112, No. 9, 2003, 11 pages.

Teixeira, et al., "Stochastic Homeostasis in Human Airway Epithelium is Achieved by Neutral Competition of Basal Cell Progenitors", eLife, vol. 2, 2013, 18 pages.

Van Galen, et al., "Single-Cell RNA-Seq Reveals AML Hierarchies Relevant to Disease Progression and Immunity", Cell, vol. 176, Mar. 7, 2019, 42 pages.

Yao, et al., "Accumulation of MtDNA Variations in Human Single Cd34+ Cells from Maternally Related Individuals: Effects of Aging and Family Genetic Background", Stem Cell Research, vol. 10, No. 3, Jan. 29, 2013, 10 pages.

Ye, et al., "Extensive Pathogenicity of Mitochondrial Heteroplasmy in Healthy Human Individuals", Proceedings of the National Academy of Sciences of the United States of America, vol. 111, No. 29, Jul. 22, 2014, 10654-10659.

* cited by examiner

Bulk mtDNA amplification by amplicon approach

Bulk mtDNA amplification by RCA approach

SEQUENCE LISTING

```
<160> NUMBER OF SEQ ID NOS: 174

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1

tggtcctagc ctttctatta gctc                                            24


<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2

gcggtcacac gattaaccca                                                 20


<210> SEQ ID NO 3
<211> LENGTH: 20
<212> TYPE: DNA
<213> ORGANISM: Artificial Sequence
<220> FEATURE:
```

<223> OTHER INFORMATION: Synthetic

<400> SEQUENCE: 3
actgctcgcc agaacactac 20

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ggtggcaaga aatgggctac a 21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tagccccaaa cccactccac 20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ctaagacccc cgaaaccaga 20

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
acagctcttt ggacactagg aa 22

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
attctcctcc gcataagcct g 21

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
accagtatta gaggcaccgc 20

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
agtacctaac aaacccacag gtc 23

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
cctcgatgtt ggatcaggac 20

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
acctcctact cctcattgta ccc 23

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
agctctcacc atcgctcttc 20

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
tggctccttt aacctctcca c 21

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
aacaccctca ccactacaat ct 22

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
cccaacccgt catctactct ac 22

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
ccggacaatg aaccataacc aa 22

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
agccttctcc tcactctctc aa 22

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
acgaccctac tactatctcg ca 22

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
ctccacctca atcacactac tcc 23

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
gccgaccgtt gactattctc t 21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
taatcggagg ctttggcaac t 21

<210> SEQ ID NO 23
<211> LENGTH: 21

<212> TYPE: DNA
<213> ORGANISM: Artificial Sequence
<220> FEATURE:
<223> OTHER INFORMATION: Synthetic

<400> SEQUENCE: 23
gcctccgtag acctaaccat c 21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
tcaacaccac cttcttcgac c 21

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
ttggcttcct agggtttatc gtg 23

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ggcctgactg gcattgtatt 20

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
acaacacttt ctcggcctat cc 22

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
tctacaagac gctacttccc c 21

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
acataacaga cgaggtcaac ga 22

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
atgagctgtc cccacattag g 21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
tgccccaact aaatactacc g 21

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
gttcgcttca ttcattgccc c 21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
cacaactaac ctcctcggac t 21

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
ctggccgtac gcctaacc 18

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
acccaccaat cacatgccta tc 22

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tccactccat aacgctcctc 20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
cccaattagg agggcactgg 20

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
tctcccttca ccatttccga c 21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
tcaacaccct cctagcctta c 21

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
ttgccctcct tttaccccta c 21

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
actagcattt accatctcac ttct 24

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
tgctaaaact aatcgtccca acaa 24

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gcaagccaac gccacttatc 20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
taggctccct tcccctactc 20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
taaagcccat gtcgaagccc 20

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
acgcctcaca ctcattctca a 21

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
ttcaccggcg cagtcatt 18

<210> SEQ ID NO 48
<211> LENGTH: 22
<212> TYPE: DNA
<213> ORGANISM: Artificial Sequence
<220> FEATURE:
<223> OTHER INFORMATION: Synthetic

<400> SEQUENCE: 48
gtgctagtaa ccacgttctc ct 22

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
caccctaacc ctgacttccc 20

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
ttcatccctg tagcattgtt cgt 23

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
cacagcagcc attcaagcaa 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gccctactcc actcaagcac 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ggcatcaacc aaccacacct 20

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
ccacatcatc gaaaccgcaa a 21

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
actaacaaca tttcccccgc a 21

<210> SEQ ID NO 56

<211> LENGTH: 20
<212> TYPE: DNA
<213> ORGANISM: Artificial Sequence
<220> FEATURE:
<223> OTHER INFORMATION: Synthetic

<400> SEQUENCE: 56
tagcatcaca caccgcacaa 20

<210> SEQ ID NO 57
<211> LENGTH: 22
<212> TYPE: DNA
<213> ORGANISM: Artificial Sequence
<220> FEATURE:
<223> OTHER INFORMATION: Synthetic

<400> SEQUENCE: 57
gctttgtttc tgttgagtgt gg 22

<210> SEQ ID NO 58
<211> LENGTH: 22
<212> TYPE: DNA
<213> ORGANISM: Artificial Sequence
<220> FEATURE:
<223> OTHER INFORMATION: Synthetic

<400> SEQUENCE: 58
ggggaatgat ggttgtcttt gg 22

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gtcagggttg attcgggagg 20

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
ccccaatacg caaaactaac cc 22

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
catcaatcgc ccacatcact c 21

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
catcggcatt atcctcctgc t 21

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
agtcccaccc tcacacgat 19

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
ccctcggctt acttctcttc c 21

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
catcctagca ataatcccca tcct 24

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
catccccgtt ccagtgagtt 20

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67 atcacccccct ccccaataaa g 21

<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
gaggcgacaa acctaccga 19

<210> SEQ ID NO 69
<211> LENGTH: 21
<212> TYPE: DNA

<213> ORGANISM: Artificial Sequence
<220> FEATURE:
<223> OTHER INFORMATION: Synthetic

<400> SEQUENCE: 69
taccctcact gtcaacccaa c 21

<210> SEQ ID NO 70
<211> LENGTH: 22
<212> TYPE: DNA
<213> ORGANISM: Artificial Sequence
<220> FEATURE:
<223> OTHER INFORMATION: Synthetic

<400> SEQUENCE: 70
gcctagccgt ttactcaatc ct 22

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71
aggaatagcc ccctttcact tc 22

<210> SEQ ID NO 72
<211> LENGTH: 22
<212> TYPE: DNA
<213> ORGANISM: Artificial Sequence
<220> FEATURE:
<223> OTHER INFORMATION: Synthetic

<400> SEQUENCE: 72
ttacctccct ctctcctact cc 22

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
cgcaacctca acaccacctt 20

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
ggtcaacgat ccctccctta c 21

<210> SEQ ID NO 75
<211> LENGTH: 22
<212> TYPE: DNA
<213> ORGANISM: Artificial Sequence
<220> FEATURE:
<223> OTHER INFORMATION: Synthetic

<400> SEQUENCE: 75
actcatttac accaaccacc ca 22

<210> SEQ ID NO 76
<211> LENGTH: 22
<212> TYPE: DNA
<213> ORGANISM: Artificial Sequence
<220> FEATURE:
<223> OTHER INFORMATION: Synthetic

<400> SEQUENCE: 76
gaaaccacac ttatccccac ct 22

<210> SEQ ID NO 77
<211> LENGTH: 37
<212> TYPE: DNA
<213> ORGANISM: Artificial Sequence
<220> FEATURE:
<223> OTHER INFORMATION: Synthetic

<400> SEQUENCE: 77
cacccgagaa ttccaaacac cctcaccact acaatct 37

<210> SEQ ID NO 78
<211> LENGTH: 38
<212> TYPE: DNA
<213> ORGANISM: Artificial Sequence
<220> FEATURE:
<223> OTHER INFORMATION: Synthetic

<400> SEQUENCE: 78
cacccgagaa ttccactcca cctcaatcac actactcc 38

<210> SEQ ID NO 79
<211> LENGTH: 37
<212> TYPE: DNA
<213> ORGANISM: Artificial Sequence
<220> FEATURE:
<223> OTHER INFORMATION: Synthetic

<400> SEQUENCE: 79
cacccgagaa ttccaacaac actttctcgg cctatcc 37

<210> SEQ ID NO 80
<211> LENGTH: 36
<212> TYPE: DNA
<213> ORGANISM: Artificial Sequence
<220> FEATURE:
<223> OTHER INFORMATION: Synthetic

<400> SEQUENCE: 80
cacccgagaa ttccatgccc caactaaata ctaccg 36

<210> SEQ ID NO 81
<211> LENGTH: 36
<212> TYPE: DNA
<213> ORGANISM: Artificial Sequence
<220> FEATURE:
<223> OTHER INFORMATION: Synthetic

<400> SEQUENCE: 81
cacccgagaa ttccatctcc cttcaccatt tccgac 36

<210> SEQ ID NO 82
<211> LENGTH: 36
<212> TYPE: DNA
<213> ORGANISM: Artificial Sequence
<220> FEATURE:

<223> OTHER INFORMATION: Synthetic

<400> SEQUENCE: 82
cacccgagaa ttccattgcc ctccttttac ccctac 36

<210> SEQ ID NO 83
<211> LENGTH: 39
<212> TYPE: DNA
<213> ORGANISM: Artificial Sequence
<220> FEATURE:
<223> OTHER INFORMATION: Synthetic

<400> SEQUENCE: 83
cacccgagaa ttccaactag catttaccat ctcacttct 39

<210> SEQ ID NO 84
<211> LENGTH: 37
<212> TYPE: DNA
<213> ORGANISM: Artificial Sequence
<220> FEATURE:
<223> OTHER INFORMATION: Synthetic

<400> SEQUENCE: 84
cacccgagaa ttccagtgct agtaaccacg ttctcct 37

<210> SEQ ID NO 85
<211> LENGTH: 35
<212> TYPE: DNA
<213> ORGANISM: Artificial Sequence
<220> FEATURE:
<223> OTHER INFORMATION: Synthetic

<400> SEQUENCE: 85
cacccgagaa ttccatagca tcacacaccg cacaa 35

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
ggatcctatt ggtgcgggg 19

<210> SEQ ID NO 87
<211> LENGTH: 34
<212> TYPE: DNA
<213> ORGANISM: Artificial Sequence
<220> FEATURE:
<223> OTHER INFORMATION: Synthetic

<400> SEQUENCE: 87
cacccgagaa ttccaggatc ctattggtgc gggg 34

<210> SEQ ID NO 88
<211> LENGTH: 39
<212> TYPE: DNA
<213> ORGANISM: Artificial Sequence
<220> FEATURE:
<223> OTHER INFORMATION: Synthetic

<400> SEQUENCE: 88
cacccgagaa ttccacatcc tagcaataat ccccatcct 39

<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89
cacccgagaa ttccatggct cctttaacct ctccac 36

<210> SEQ ID NO 90
<211> LENGTH: 37
<212> TYPE: DNA
<213> ORGANISM: Artificial Sequence
<220> FEATURE:
<223> OTHER INFORMATION: Synthetic

<400> SEQUENCE: 90
cacccgagaa ttccaacgac cctactacta tctcgca 37

<210> SEQ ID NO 91
<211> LENGTH: 35
<212> TYPE: DNA
<213> ORGANISM: Artificial Sequence
<220> FEATURE:
<223> OTHER INFORMATION: Synthetic

<400> SEQUENCE: 91
cacccgagaa ttccaggcct gactggcatt gtatt 35

<210> SEQ ID NO 92
<211> LENGTH: 36
<212> TYPE: DNA
<213> ORGANISM: Artificial Sequence
<220> FEATURE:
<223> OTHER INFORMATION: Synthetic

<400> SEQUENCE: 92
cacccgagaa ttccaggtca acgatccctc ccttac 36

<210> SEQ ID NO 93
<211> LENGTH: 36
<212> TYPE: DNA
<213> ORGANISM: Artificial Sequence
<220> FEATURE:
<223> OTHER INFORMATION: Synthetic

<400> SEQUENCE: 93
cacccgagaa ttccacacaa ctaacctcct cggact 36

<210> SEQ ID NO 94
<211> LENGTH: 35
<212> TYPE: DNA
<213> ORGANISM: Artificial Sequence
<220> FEATURE:
<223> OTHER INFORMATION: Synthetic

<400> SEQUENCE: 94
cacccgagaa ttccacccaa ttaggagggc actgg 35

<210> SEQ ID NO 95
<211> LENGTH: 22
<212> TYPE: DNA
<213> ORGANISM: Artificial Sequence
<220> FEATURE:
<223> OTHER INFORMATION: Synthetic

<400> SEQUENCE: 95
actaccacaa ctcaacggct ac 22

<210> SEQ ID NO 96
<211> LENGTH: 37
<212> TYPE: DNA
<213> ORGANISM: Artificial Sequence
<220> FEATURE:
<223> OTHER INFORMATION: Synthetic

<400> SEQUENCE: 96
cacccgagaa ttccaactac cacaactcaa cggctac 37

<210> SEQ ID NO 97
<211> LENGTH: 33
<212> TYPE: DNA
<213> ORGANISM: Artificial Sequence
<220> FEATURE:
<223> OTHER INFORMATION: Synthetic

<400> SEQUENCE: 97
cacccgagaa ttccattcac cggcgcagtc att 33

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
cgcatccccc ttccaaaca 19

<210> SEQ ID NO 99
<211> LENGTH: 34
<212> TYPE: DNA
<213> ORGANISM: Artificial Sequence
<220> FEATURE:
<223> OTHER INFORMATION: Synthetic

<400> SEQUENCE: 99
cacccgagaa ttccacgcat cccccttcca aaca 34

<210> SEQ ID NO 100
<211> LENGTH: 37
<212> TYPE: DNA
<213> ORGANISM: Artificial Sequence
<220> FEATURE:
<223> OTHER INFORMATION: Synthetic

<400> SEQUENCE: 100
cacccgagaa ttccagggga atgatggttg tctttgg 37

<210> SEQ ID NO 101
<211> LENGTH: 36
<212> TYPE: DNA
<213> ORGANISM: Artificial Sequence
<220> FEATURE:
<223> OTHER INFORMATION: Synthetic

<400> SEQUENCE: 101
cacccgagaa ttccaccctc ggcttacttc tcttcc 36

<210> SEQ ID NO 102
<211> LENGTH: 35

<212> TYPE: DNA
<213> ORGANISM: Artificial Sequence
<220> FEATURE:
<223> OTHER INFORMATION: Synthetic

<400> SEQUENCE: 102
cacccgagaa ttccaagctc tcaccatcgc tcttc 35

<210> SEQ ID NO 103
<211> LENGTH: 37
<212> TYPE: DNA
<213> ORGANISM: Artificial Sequence
<220> FEATURE:
<223> OTHER INFORMATION: Synthetic

<400> SEQUENCE: 103
cacccgagaa ttccaagcct tctcctcact ctctcaa 37

<210> SEQ ID NO 104
<211> LENGTH: 38
<212> TYPE: DNA
<213> ORGANISM: Artificial Sequence
<220> FEATURE:
<223> OTHER INFORMATION: Synthetic

<400> SEQUENCE: 104
cacccgagaa ttccattggc ttcctagggt ttatcgtg 38

<210> SEQ ID NO 105
<211> LENGTH: 36
<212> TYPE: DNA
<213> ORGANISM: Artificial Sequence
<220> FEATURE:
<223> OTHER INFORMATION: Synthetic

<400> SEQUENCE: 105
cacccgagaa ttccatctac aagacgctac ttcccc 36

<210> SEQ ID NO 106
<211> LENGTH: 36
<212> TYPE: DNA
<213> ORGANISM: Artificial Sequence
<220> FEATURE:
<223> OTHER INFORMATION: Synthetic

<400> SEQUENCE: 106
cacccgagaa ttccagttcg cttcattcat tgcccc 36

<210> SEQ ID NO 107
<211> LENGTH: 35
<212> TYPE: DNA
<213> ORGANISM: Artificial Sequence
<220> FEATURE:
<223> OTHER INFORMATION: Synthetic

<400> SEQUENCE: 107
cacccgagaa ttccatccac tccataacgc tcctc 35

<210> SEQ ID NO 108
<211> LENGTH: 36
<212> TYPE: DNA
<213> ORGANISM: Artificial Sequence
<220> FEATURE:
<223> OTHER INFORMATION: Synthetic

<400> SEQUENCE: 108
cacccgagaa ttccaacgcc tcacactcat tctcaa 36

<210> SEQ ID NO 109
<211> LENGTH: 36
<212> TYPE: DNA
<213> ORGANISM: Artificial Sequence
<220> FEATURE:
<223> OTHER INFORMATION: Synthetic

<400> SEQUENCE: 109
cacccgagaa ttccaccaca tcatcgaaac cgcaaa 36

<210> SEQ ID NO 110
<211> LENGTH: 37
<212> TYPE: DNA
<213> ORGANISM: Artificial Sequence
<220> FEATURE:
<223> OTHER INFORMATION: Synthetic

<400> SEQUENCE: 110
cacccgagaa ttccagcttt gtttctgttg agtgtgg 37

<210> SEQ ID NO 111
<211> LENGTH: 34
<212> TYPE: DNA
<213> ORGANISM: Artificial Sequence
<220> FEATURE:
<223> OTHER INFORMATION: Synthetic

<400> SEQUENCE: 111
cacccgagaa ttccaagtcc caccctcaca cgat 34

<210> SEQ ID NO 112
<211> LENGTH: 39
<212> TYPE: DNA
<213> ORGANISM: Artificial Sequence
<220> FEATURE:
<223> OTHER INFORMATION: Synthetic

<400> SEQUENCE: 112
cacccgagaa ttccatggtc ctagcctttc tattagctc 39

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
tacaactacg caaaggcccc 20

<210> SEQ ID NO 114
<211> LENGTH: 35
<212> TYPE: DNA
<213> ORGANISM: Artificial Sequence
<220> FEATURE:
<223> OTHER INFORMATION: Synthetic

<400> SEQUENCE: 114
cacccgagaa ttccatacaa ctacgcaaag gcccc 35

<210> SEQ ID NO 115
<211> LENGTH: 37
<212> TYPE: DNA
<213> ORGANISM: Artificial Sequence
<220> FEATURE:
<223> OTHER INFORMATION: Synthetic

<400> SEQUENCE: 115
cacccgagaa ttccaccgga caatgaacca taaccaa 37

<210> SEQ ID NO 116
<211> LENGTH: 36
<212> TYPE: DNA
<213> ORGANISM: Artificial Sequence
<220> FEATURE:
<223> OTHER INFORMATION: Synthetic

<400> SEQUENCE: 116
cacccgagaa ttccatcaac accaccttct tcgacc 36

<210> SEQ ID NO 117
<211> LENGTH: 37
<212> TYPE: DNA
<213> ORGANISM: Artificial Sequence
<220> FEATURE:
<223> OTHER INFORMATION: Synthetic

<400> SEQUENCE: 117
cacccgagaa ttccaaccca ccaatcacat gcctatc 37

<210> SEQ ID NO 118
<211> LENGTH: 35
<212> TYPE: DNA
<213> ORGANISM: Artificial Sequence
<220> FEATURE:
<223> OTHER INFORMATION: Synthetic

<400> SEQUENCE: 118
cacccgagaa ttccataaag cccatgtcga agccc 35

<210> SEQ ID NO 119
<211> LENGTH: 35
<212> TYPE: DNA
<213> ORGANISM: Artificial Sequence
<220> FEATURE:
<223> OTHER INFORMATION: Synthetic

<400> SEQUENCE: 119
cacccgagaa ttccaggcat caaccaacca cacct 35

<210> SEQ ID NO 120
<211> LENGTH: 36
<212> TYPE: DNA
<213> ORGANISM: Artificial Sequence
<220> FEATURE:
<223> OTHER INFORMATION: Synthetic

<400> SEQUENCE: 120
cacccgagaa ttccacatcg gcattatcct cctgct 36

<210> SEQ ID NO 121
<211> LENGTH: 37
<212> TYPE: DNA
<213> ORGANISM: Artificial Sequence
<220> FEATURE:
<223> OTHER INFORMATION: Synthetic

<400> SEQUENCE: 121
cacccgagaa ttccacccaa cccgtcatct actctac 37

<210> SEQ ID NO 122
<211> LENGTH: 36
<212> TYPE: DNA
<213> ORGANISM: Artificial Sequence
<220> FEATURE:
<223> OTHER INFORMATION: Synthetic

<400> SEQUENCE: 122
cacccgagaa ttccagcctc cgtagaccta accatc 36

<210> SEQ ID NO 123
<211> LENGTH: 35
<212> TYPE: DNA
<213> ORGANISM: Artificial Sequence
<220> FEATURE:
<223> OTHER INFORMATION: Synthetic

<400> SEQUENCE: 123
cacccgagaa ttccataggc tcccttcccc tactc 35

<210> SEQ ID NO 124
<211> LENGTH: 35
<212> TYPE: DNA
<213> ORGANISM: Artificial Sequence
<220> FEATURE:
<223> OTHER INFORMATION: Synthetic

<400> SEQUENCE: 124
cacccgagaa ttccagccct actccactca agcac 35

<210> SEQ ID NO 125
<211> LENGTH: 36
<212> TYPE: DNA
<213> ORGANISM: Artificial Sequence
<220> FEATURE:
<223> OTHER INFORMATION: Synthetic

<400> SEQUENCE: 125
cacccgagaa ttccacatca atcgcccaca tcactc 36

<210> SEQ ID NO 126
<211> LENGTH: 35
<212> TYPE: DNA
<213> ORGANISM: Artificial Sequence
<220> FEATURE:
<223> OTHER INFORMATION: Synthetic

<400> SEQUENCE: 126
cacccgagaa ttccaaccag tattagaggc accgc 35

<210> SEQ ID NO 127
<211> LENGTH: 36
<212> TYPE: DNA
<213> ORGANISM: Artificial Sequence
<220> FEATURE:
<223> OTHER INFORMATION: Synthetic

<400> SEQUENCE: 127
cacccgagaa ttccataatc ggaggctttg gcaact 36

<210> SEQ ID NO 128
<211> LENGTH: 35
<212> TYPE: DNA
<213> ORGANISM: Artificial Sequence
<220> FEATURE:
<223> OTHER INFORMATION: Synthetic

<400> SEQUENCE: 128
cacccgagaa ttccagcaag ccaacgccac ttatc 35

<210> SEQ ID NO 129
<211> LENGTH: 35
<212> TYPE: DNA
<213> ORGANISM: Artificial Sequence
<220> FEATURE:
<223> OTHER INFORMATION: Synthetic

<400> SEQUENCE: 129
cacccgagaa ttccacacag cagccattca agcaa 35

<210> SEQ ID NO 130
<211> LENGTH: 22
<212> TYPE: DNA
<213> ORGANISM: Artificial Sequence
<220> FEATURE:
<223> OTHER INFORMATION: Synthetic

<400> SEQUENCE: 130
aaccactcat tcatcgacct cc 22

<210> SEQ ID NO 131
<211> LENGTH: 37
<212> TYPE: DNA
<213> ORGANISM: Artificial Sequence
<220> FEATURE:
<223> OTHER INFORMATION: Synthetic

<400> SEQUENCE: 131
cacccgagaa ttccaaacca ctcattcatc gacctcc 37

<210> SEQ ID NO 132
<211> LENGTH: 37
<212> TYPE: DNA
<213> ORGANISM: Artificial Sequence
<220> FEATURE:
<223> OTHER INFORMATION: Synthetic

<400> SEQUENCE: 132
cacccgagaa ttccaacagc tctttggaca ctaggaa 37

<210> SEQ ID NO 133
<211> LENGTH: 36
<212> TYPE: DNA
<213> ORGANISM: Artificial Sequence
<220> FEATURE:
<223> OTHER INFORMATION: Synthetic

<400> SEQUENCE: 133
cacccgagaa ttccagccga ccgttgacta ttctct 36

<210> SEQ ID NO 134
<211> LENGTH: 39
<212> TYPE: DNA
<213> ORGANISM: Artificial Sequence
<220> FEATURE:
<223> OTHER INFORMATION: Synthetic

<400> SEQUENCE: 134
cacccgagaa ttccatgcta aaactaatcg tcccaacaa 39

<210> SEQ ID NO 135

<211> LENGTH: 38
<212> TYPE: DNA
<213> ORGANISM: Artificial Sequence
<220> FEATURE:
<223> OTHER INFORMATION: Synthetic

<400> SEQUENCE: 135
cacccgagaa ttccattcat ccctgtagca ttgttcgt 38

<210> SEQ ID NO 136
<211> LENGTH: 35
<212> TYPE: DNA
<213> ORGANISM: Artificial Sequence
<220> FEATURE:
<223> OTHER INFORMATION: Synthetic

<400> SEQUENCE: 136
cacccgagaa ttccatagcc ccaaacccac tccac 35

<210> SEQ ID NO 137
<211> LENGTH: 35
<212> TYPE: DNA
<213> ORGANISM: Artificial Sequence
<220> FEATURE:
<223> OTHER INFORMATION: Synthetic

<400> SEQUENCE: 137
cacccgagaa ttccacaccc taaccctgac ttccc 35

<210> SEQ ID NO 138
<211> LENGTH: 36
<212> TYPE: DNA
<213> ORGANISM: Artificial Sequence
<220> FEATURE:
<223> OTHER INFORMATION: Synthetic

<400> SEQUENCE: 138
cacccgagaa ttccaggtgg caagaaatgg gctaca 36

<210> SEQ ID NO 139
<211> LENGTH: 35
<212> TYPE: DNA
<213> ORGANISM: Artificial Sequence
<220> FEATURE:
<223> OTHER INFORMATION: Synthetic

<400> SEQUENCE: 139
cacccgagaa ttccacctcg atgttggatc aggac 35

<210> SEQ ID NO 140
<211> LENGTH: 33
<212> TYPE: DNA
<213> ORGANISM: Artificial Sequence
<220> FEATURE:
<223> OTHER INFORMATION: Synthetic

<400> SEQUENCE: 140
cacccgagaa ttccactggc cgtacgccta acc 33

<210> SEQ ID NO 141
<211> LENGTH: 35
<212> TYPE: DNA
<213> ORGANISM: Artificial Sequence
<220> FEATURE:
<223> OTHER INFORMATION: Synthetic

<400> SEQUENCE: 141
cacccgagaa ttccaactgc tcgccagaac actac 35

<210> SEQ ID NO 142
<211> LENGTH: 38
<212> TYPE: DNA
<213> ORGANISM: Artificial Sequence
<220> FEATURE:
<223> OTHER INFORMATION: Synthetic

<400> SEQUENCE: 142
cacccgagaa ttccaagtac ctaacaaacc cacaggtc 38

<210> SEQ ID NO 143
<211> LENGTH: 35
<212> TYPE: DNA
<213> ORGANISM: Artificial Sequence
<220> FEATURE:
<223> OTHER INFORMATION: Synthetic

<400> SEQUENCE: 143
cacccgagaa ttccagcggt cacacgatta accca 35

<210> SEQ ID NO 144
<211> LENGTH: 36
<212> TYPE: DNA
<213> ORGANISM: Artificial Sequence
<220> FEATURE:
<223> OTHER INFORMATION: Synthetic

<400> SEQUENCE: 144
cacccgagaa ttccaattct cctccgcata agcctg 36

<210> SEQ ID NO 145
<211> LENGTH: 35
<212> TYPE: DNA
<213> ORGANISM: Artificial Sequence
<220> FEATURE:
<223> OTHER INFORMATION: Synthetic

<400> SEQUENCE: 145
cacccgagaa ttccactaag acccccgaaa ccaga 35

<210> SEQ ID NO 146
<211> LENGTH: 36
<212> TYPE: DNA
<213> ORGANISM: Artificial Sequence
<220> FEATURE:
<223> OTHER INFORMATION: Synthetic

<400> SEQUENCE: 146
cacccgagaa ttccaatgag ctgtccccac attagg 36

<210> SEQ ID NO 147
<211> LENGTH: 29
<212> TYPE: DNA
<213> ORGANISM: Artificial Sequence
<220> FEATURE:
<223> OTHER INFORMATION: Synthetic

<400> SEQUENCE: 147
agatcggaag agcgtcgtgt agggaaaga 29

<210> SEQ ID NO 148
<211> LENGTH: 57
<212> TYPE: RNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: V represents a or g or c
<220> FEATURE:
<221> NAME/KEY: misc_feature
<223> OTHER INFORMATION: V ia a or g or c
<220> FEATURE:
<221> NAME/KEY: misc_feature
<222> LOCATION: (56)..(56)
<223> OTHER INFORMATION: n is a, c, g, or u
<220> FEATURE:
<221> NAME/KEY: misc_feature
<222> LOCATION: (62)..(62)
<223> OTHER INFORMATION: V represents a or g or c

<400> SEQUENCE: 148
gguauuuggu uucccagucc acuauacuga cgucuccaac augagccgcu uggcgnv 57

<210> SEQ ID NO 149
<211> LENGTH: 30
<212> TYPE: RNA
<213> ORGANISM: Artificial Sequence
<220> FEATURE:
<223> OTHER INFORMATION: Synthetic

<400> SEQUENCE: 149
aaaaaaaaaa aaaaaaaaaa aaaaaaaaaa 30

<210> SEQ ID NO 150
<211> LENGTH: 82
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(50)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (99)..(99)
<223> OTHER INFORMATION: V ia a or g or c

<400> SEQUENCE: 150
ctacacgacg ctcttccgat ctnnnnnnnn nnnnnnnnnn nnnnnnnnnn tttttttttt 60
tttttttttt tttttttttt vn 82

<210> SEQ ID NO 151
<211> LENGTH: 30
<212> TYPE: DNA
<213> ORGANISM: Artificial Sequence
<220> FEATURE:
<223> OTHER INFORMATION: Synthetic

<400> SEQUENCE: 151
aagcagtggt atcaacgcag agtacatggg 30

<210> SEQ ID NO 152
<211> LENGTH: 55
<212> TYPE: DNA
<213> ORGANISM: Artificial Sequence
<220> FEATURE:
<223> OTHER INFORMATION: Synthetic

<400> SEQUENCE: 152
ggtatttggt ttcccagtcc actatactga cgtctccaac atgagccgct tggcg 55

<210> SEQ ID NO 153
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(31)
<223> OTHER INFORMATION: n is a, c, g, or t

<400> SEQUENCE: 153
aaannnnnnn nnnnnnnnnn nnnnnnnnnn nagatcggaa gagcgtcgtg tag 53

<210> SEQ ID NO 154
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(50)
<223> OTHER INFORMATION: n is a, c, g, or t

<400> SEQUENCE: 154
ctacacgacg ctcttccgat ctnnnnnnnn nnnnnnnnnn nnnnnnnnnn ttt 53

<210> SEQ ID NO 155
<211> LENGTH: 55
<212> TYPE: DNA
<213> ORGANISM: Artificial Sequence
<220> FEATURE:
<223> OTHER INFORMATION: Synthetic

<400> SEQUENCE: 155
cgccaagcgg ctcatgttgg agacgtcagt atagtggact gggaaaccaa atacc 55

<210> SEQ ID NO 156
<211> LENGTH: 30
<212> TYPE: DNA
<213> ORGANISM: Artificial Sequence
<220> FEATURE:
<223> OTHER INFORMATION: Synthetic

<400> SEQUENCE: 156
cccatgtact ctgcgttgat accactgctt 30

<210> SEQ ID NO 157
<211> LENGTH: 30
<212> TYPE: DNA
<213> ORGANISM: Artificial Sequence
<220> FEATURE:
<223> OTHER INFORMATION: Synthetic

<400> SEQUENCE: 157
aagcagtggt atcaacgcag agtacatggg 30

<210> SEQ ID NO 158
<211> LENGTH: 55
<212> TYPE: DNA
<213> ORGANISM: Artificial Sequence
<220> FEATURE:

<223> OTHER INFORMATION: Synthetic

<400> SEQUENCE: 158
ggtatttggt ttcccagtcc actatactga cgtctccaac atgagccgct tggcg 55

<210> SEQ ID NO 159
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(19)
<223> OTHER INFORMATION: n is a, c, g, or t

<400> SEQUENCE: 159
aaannnnnnn nnnnnnnnna gatcggaaga gcgtcgtgta g 41

<210> SEQ ID NO 160
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 160
aatgatacgg cgaccaccga gatctacacn nnnnnnntct ttccctacac gacgctc 57

<210> SEQ ID NO 161
<211> LENGTH: 36
<212> TYPE: DNA
<213> ORGANISM: Artificial Sequence
<220> FEATURE:
<223> OTHER INFORMATION: Synthetic

<400> SEQUENCE: 161
cacccgagaa ttccaactga cgtctccaac atgagc 36

<210> SEQ ID NO 162
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(50)
<223> OTHER INFORMATION: n is a, c, g, or t

<400> SEQUENCE: 162
ctacacgacg ctcttccgat ctnnnnnnnn nnnnnnnnnn nnnnnnnnnn ttt 53

<210> SEQ ID NO 163
<211> LENGTH: 55
<212> TYPE: DNA
<213> ORGANISM: Artificial Sequence
<220> FEATURE:
<223> OTHER INFORMATION: Synthetic

<400> SEQUENCE: 163
cgccaagcgg ctcatgttgg agacgtcagt atagtggact gggaaaccaa atacc 55

<210> SEQ ID NO 164
<211> LENGTH: 30
<212> TYPE: DNA
<213> ORGANISM: Artificial Sequence
<220> FEATURE:
<223> OTHER INFORMATION: Synthetic

<400> SEQUENCE: 164
cccatgtact ctgcgttgat accactgctt 30

<210> SEQ ID NO 165
<211> LENGTH: 45
<212> TYPE: DNA
<213> ORGANISM: Artificial Sequence
<220> FEATURE:
<223> OTHER INFORMATION: Synthetic

<400> SEQUENCE: 165
cacccgagaa ttccaactga cgtctccaac atgagccgct tggcg 45

<210> SEQ ID NO 166
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(31)
<223> OTHER INFORMATION: n is a, c, g, or t
<220> FEATURE:
<221> NAME/KEY: misc_feature
<222> LOCATION: (61)..(68)
<223> OTHER INFORMATION: n is a, c, g, or t

<400> SEQUENCE: 166
aaannnnnnn nnnnnnnnnn nnnnnnnnnn nagatcggaa gagcgtcgtg tagggaaaga 60
nnnnnnnngt gtagatctcg gtggtcgccg tatcatt 97

<210> SEQ ID NO 167
<211> LENGTH: 29
<212> TYPE: DNA
<213> ORGANISM: Artificial Sequence
<220> FEATURE:
<223> OTHER INFORMATION: Synthetic

<400> SEQUENCE: 167
aatgatacgg cgaccaccga gatctacac 29

<210> SEQ ID NO 168
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(32)
<223> OTHER INFORMATION: n is a, c, g, or t

<400> SEQUENCE: 168
caagcagaag acggcatacg agatnnnnnn nngtgactgg agttccttgg cacccgagaa 60
ttcca 65

<210> SEQ ID NO 169
<211> LENGTH: 97
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t
<220> FEATURE:
<221> NAME/KEY: misc_feature
<222> LOCATION: (67)..(94)
<223> OTHER INFORMATION: n is a, c, g, or t

<400> SEQUENCE: 169
aatgatacgg cgaccaccga gatctacacn nnnnnnntct ttccctacac gacgctcttc 60
cgatctnnnn nnnnnnnnnn nnnnnnnnnn nnnnttt 97

<210> SEQ ID NO 170
<211> LENGTH: 45
<212> TYPE: DNA
<213> ORGANISM: Artificial Sequence
<220> FEATURE:
<223> OTHER INFORMATION: Synthetic

<400> SEQUENCE: 170
cgccaagcgg ctcatgttgg agacgtcagt tggaattctc gggtg 45

<210> SEQ ID NO 171
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(32)
<223> OTHER INFORMATION: n is a, c, g, or t

<400> SEQUENCE: 171
caagcagaag acggcatacg agatnnnnnn nngtgactgg agttccttgg cacccgagaa 60
ttccaactga cgtctccaac atgagccgct tggcg 95

<210> SEQ ID NO 172
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(31)
<223> OTHER INFORMATION: n is a, c, g, or t
<220> FEATURE:
<221> NAME/KEY: misc_feature
<222> LOCATION: (61)..(68)
<223> OTHER INFORMATION: n is a, c, g, or t

<400> SEQUENCE: 172
aaannnnnnn nnnnnnnnnn nnnnnnnnnn nagatcggaa gagcgtcgtg tagggaaaga 60
nnnnnnnngt gtagatctcg gtggtcgccg tatcatt 97

<210> SEQ ID NO 173
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: misc_feature -continued

```
<222> LOCATION: (30)..(37)
<223> OTHER INFORMATION: n is a, c, g, or t
<220> FEATURE:
<221> NAME/KEY: misc_feature
<222> LOCATION: (67)..(94)
<223> OTHER INFORMATION: n is a, c, g, or t

<400> SEQUENCE: 173

aatgatacgg cgaccaccga gatctacacn nnnnnnntct ttccctacac gacgctcttc     60

cgatctnnnn nnnnnnnnnn nnnnnnnnnn nnnnttt                               97


<210> SEQ ID NO 174
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (64)..(71)
<223> OTHER INFORMATION: n is a, c, g, or t

<400> SEQUENCE: 174

cgccaagcgg ctcatgttgg agacgtcagt tggaattctc gggtgccaag gaactccagt     60

cacnnnnnnn natctcgtat gccgtcttct gcttg                                 95
```

LINEAGE INFERENCE FROM SINGLE-CELL TRANSCRIPTOMES

CROSS-REFERENCE TO RELATED APPLICATIONS

This application claims the benefit of U.S. Provisional Application Nos. 62/881,148, filed Jul. 31, 2019 and 63/002,147, filed Mar. 30, 2020. The entire contents of the above-identified applications are hereby fully incorporated herein by reference.

STATEMENT REGARDING FEDERALLY SPONSORED RESEARCH

This invention was made with government support under Grant Nos. CA218832 and CA216873 awarded by the National Institutes of Health. The government has certain rights in the invention.

REFERENCE TO AN ELECTRONIC SEQUENCE LISTING

The contents of the electronic sequence listing (BROD_4600US_ST25.txt"; Size is 35 Kilobytes and it was created on Jul. 24, 2020) is herein incorporated by reference in its entirety.

TECHNICAL FIELD

The subject matter disclosed herein is generally directed to inferring cell lineages in native contexts and measuring clonal dynamics in complex cellular populations by detection of somatic mitochondrial mutations, somatic nuclear mutations, and transcriptomes from a single cell high throughput RNA-seq library.

BACKGROUND

All cells in the human body are derived from the zygote, but we lack a detailed map integrating cell division (lineage) and differentiation (fate) and their dynamics from stem cells to their differentiated progeny. Such a map would significantly expand our understanding of cellular processes underlying human development, tissue homeostasis, and disease.

In human tissues in vivo, where such genetic manipulations are not readily possible (L. Biasco et al., In Vivo Tracking of Human Hematopoiesis Reveals Patterns of Clonal Dynamics during Early and Steady-State Reconstitution Phases. *Cell Stem Cell* 19, 107-119 (2016)), we must rely on naturally occurring somatic mutations, including single nucleotide variants (SNVs), copy number variants (CNVs), and variation in short tandem repeat sequences (microsatellites or STRs), which are stably propagated to daughter cells, but absent in distantly related cells (M. A. Lodato et al., Somatic mutation in single human neurons tracks developmental and transcriptional history. *Science* 350, 94-98 (2015); and Y. S. Ju et al., Somatic mutations reveal asymmetric cellular dynamics in the early human embryo. Nature 543, 714-718 (2017)).

Although single cell approaches have been developed to detect somatic mutations in the nuclear genome in human cells, they are costly, difficult to apply at scale, have substantial error rates, and do not provide information on cell state. In particular, reliable mutation detection from a single genomic copy remains technically challenging (T. Biezuner et al., A generic, cost-effective, and scalable cell lineage analysis platform. *Genome Res* 26, 1588-1599 (2016); K. Naxerova et al., Origins of lymphatic and distant metastases in human colorectal cancer. *Science* 357, 55-60 (2017); and L. Tao et al., A duplex MIPs-based biological-computational cell lineage discovery platform. *BioRxiv*, (Oct. 14, 2017)), with high error rates during whole genome amplification of single cells, leading to allelic dropout, false positive artifacts, and non-uniform coverage (H. Zafar, A. Tzen, N. Navin, K. Chen, L. Nakhleh, SiFit: inferring tumor trees from single-cell sequencing data under finite-sites models. *Genome Biol* 18, 178 (2017); T. Biezuner, O. Raz, S. Amir, L. Milo, R. Adar, Comparison of seven single cell Whole Genome Amplification commercial kits using targeted sequencing. *BioRxiv*, (Sep. 11, 2017); and W. K. Chu et al., Ultraaccurate genome sequencing and haplotyping of single human cells. *Proc Natl Acad Sci USA* , (2017)). Moreover, single-cell sequencing of the entire human genome is cost-prohibitive and currently has limited throughput. Finally, most methods have not been or cannot be readily combined with methods that would report on the cell type and state based on RNA profiles or chromatin organization.

The impact of high-throughput single-cell RNA-seq technologies is increasingly appreciated by the scientific community, and commercialized platforms are now available that massively parallelize the generation of single cell RNA-seq libraries, enabling the creation of RNA-seq libraries for $10^4$-$10^5$ cells. All the highly parallelized tools fuse the same cellular DNA barcode to all transcripts isolated from a cell during reverse transcription, creating so-called 3'-barcoded single cell RNA-seq libraries derived from random sequencing reads. However, it remains challenging to sequence defined portions of a transcript while maintaining the barcode for single cell identification of the transcript, particularly when the sequence is on the 5' side of the transcripts.

One major application of single-cell RNA-seq is the ability for unbiased detection of different cell types in complex tissues. For example, when applied to a cancer patient's tumor, single-cell RNA-seq can unravel the different cell types, including tumor cells with different transcriptional states, stromal cells and immune cells. However, in addition to transcription states, it would also be valuable to determine a clonal structure of tumor cells. A method that can leverage high throughput single cell RNA sequencing to determine cell state, somatic mutations, and clonal structure is needed.

SUMMARY

In one aspect, the present invention provides for a method of determining a lineage and/or clonal structure of single cells in a multicellular eukaryotic organism comprising enriching mitochondrial cDNA from a barcoded single cell cDNA library derived from transcripts obtained from single cells from a subject, wherein the cDNA comprises a cell barcode that identifies the cell of origin for the transcripts and a UMI that identifies each individual transcript; detecting somatic mutations in sequencing reads of the enriched mitochondrial cDNA; and clustering the single cells based on the presence of the mutations in mitochondria in the single cells, whereby a lineage and/or clonal structure for the single cells is retrospectively inferred. In certain embodiments, the cDNA library is generated by whole transcriptome amplification (WTA). In certain embodiments, the method further comprises enriching nuclear cDNA from the barcoded single cell cDNA library; and determining somatic nuclear mutations in the clustered cells, thereby determining somatic nuclear mutations in the lineage and/or clonal structure. In certain embodiments, the method further comprises generating an RNA-seq library from the barcoded single cell cDNA library and determining the transcriptome of the clustered cells, thereby determining cell transcriptional states in the lineage and/or clonal structure. In certain embodiments, somatic nuclear mutations and cell transcriptional states are determined in the lineage and/or clonal structure.

In certain embodiments, enriching cDNA comprises PCR amplification. In certain embodiments, enriching mitochondrial cDNA comprises amplification with one or more primers selected from Table 1 or Table 2. In certain embodiments, the PCR primers comprise a binding moiety and the method further comprises enriching for the target cDNA with a solid support specific for the binding moiety. In certain embodiments, the binding moiety is biotin and solid support comprises streptavidin.

In certain embodiments, the cDNA is flanked by sequencing adaptors at the 5' and 3' ends.

In certain embodiments, enriching and detecting mutations comprises: amplifying each cDNA in the library to create a first PCR product using a tagged 5' primer comprising a binding site for a second PCR product and a sequence complementary to a specific gene of interest and a 3' primer complementary to the adapter sequence at the 3' end of the cDNA, thereby generating a first PCR product; selectively enriching the first PCR product by binding to the tag introduced by the 5' primer or a targeted 3' capture with a bifunctional bead or targeted capture bead; amplifying the tag-enriched first PCR product with a 5' primer comprising the binding site for the second PCR product and a 3' primer complementary to the adapter sequence at the 3' end of the cDNA, thereby generating a second PCR product; optionally amplifying the second PCR product with a 5' primer comprising the binding site for a third PCR product and a 3' primer complementary to the adapter sequence at the 3' end of the cDNA, thereby generating the third PCR product; and detecting somatic mutations, barcodes and UMIs in single sequencing reads of the enriched cDNA. In certain embodiments, the tagged 5' primer comprises a biotin tag.

In certain embodiments, the tagged 5' primer and the 3' primer further comprise USER sequences, thereby generating a first PCR product comprising USER sequences, and the method further comprises treating the first PCR product with a uracil-specific excision reagent ("USER®") enzyme, circularizing the first PCR product by sticky end ligation, and amplifying the tag-enriched circularized PCR product with a 5' primer complementary to gene of interest and having a sequence adapter and a 3' primer having a polyA tail and another sequence adapter thereby generating the second PCR product. In certain embodiments, wherein the 5' primer for the first PCR is selected from Table 1 or Table 2.

In certain embodiments, enriching comprises hybridization of cDNA molecules to oligonucleotides specific for target transcript sequences and separating the oligonucleotides hybridized to the target transcript sequences from the library.

In certain embodiments, heritable cell states are identified. In certain embodiments, the establishment of a cell state along a lineage is identified. In certain embodiments, the single cells comprise related cell types. In certain embodiments, the related cell types are from a tissue. In certain embodiments, the tissue is associated with a disease state, thereby determining the lineage of the tissue associated with the disease and/or phylogeny of cell lineages for the tissue. In certain embodiments, the disease is a degenerative disease. In certain embodiments, the tissue is healthy tissue. In certain embodiments, the tissue is diseased tissue.

In certain embodiments, the cells obtained from a subject are selected for a cell type. In certain embodiments, stem and progenitor cells are selected. In certain embodiments, CD34+ hematopoietic stem and progenitor cells are selected. In certain embodiments, the method further comprises determining a lineage and/or clonal structure for single cells from two or more tissues. In certain embodiments, the related cell types are from a tumor sample, thereby determining clonal populations of cells in a tumor sample. In certain embodiments, the clonal structure of tumor cells is determined. In certain embodiments, the clonal structure of tumor infiltrating immune cells is determined. In certain embodiments, the immune cells are selected from the group consisting of T cells, B cells, macrophages, neutrophils, dendritic cells, megakaryocytes, monocytes, basophils, and eosinophils. In certain embodiments, the tumor sample is obtained before cancer treatment. In certain embodiments, the method further comprises obtaining a tumor sample after treatment and comparing the presence of clonal populations before and after treatment, wherein clonal populations of cells sensitive and resistant to the treatment are identified. In certain embodiments, the cancer treatment comprises chemotherapy, radiation therapy, immunotherapy, targeted therapy, or a combination thereof.

In another aspect, the present invention provides for a method of identifying a cancer therapeutic target comprising detecting clonal populations of cells in a tumor sample according to any embodiment herein; identifying differential cell states between the clonal populations; identifying a cell state present in resistant clonal populations, thereby identifying a therapeutic target. In certain embodiments, the cell state is a differentially expressed gene, differentially expressed gene signature, or a differentially accessible chromatin loci. In another aspect, the present invention provides for a method of treatment comprising administering a treatment targeting a differentially expressed gene, differentially expressed gene signature, or a differentially accessible chromatin loci.

In another aspect, the present invention provides for a method of screening for a cancer treatment comprising growing a tumor sample obtained from a subject in need thereof; determining clonal populations in the tumor sample according to any embodiment herein; treating the tumor sample with one or more agents; and determining the effect of the one or more agents on the clonal populations. In certain embodiments, the tumor cells are grown in vitro. In certain embodiments, the tumor cells are grown in vivo. In certain embodiments, the tumor cells are grown as a patient derived xenograft (PDX). In certain embodiments, the method further comprises identifying differential cell states between sensitive and resistant clonal populations. In certain embodiments, peripheral blood mononuclear cells (PBMCs) and/or bone marrow mononuclear cells (BMMCs) are selected. In certain embodiments, PBMCs and/or bone marrow mononuclear cells are selected before and after stem cell transplantation in a subject.

In another aspect, the present invention provides for a method of identifying changes in clonal populations having a cell state between healthy and diseased tissue comprising determining clonal populations of cells having a cell state in healthy and diseased cells according to any embodiment herein; and comparing the clonal populations.

In certain embodiments, the related cell types are immune cells, thereby determining the clonal relatedness of immune cells. In certain embodiments, the immune cells are of the myeloid or lymphoid lineage. In certain embodiments, mitochondrial mutations associated with the bone marrow or tissue are detected in the myeloid cells, thereby determining whether the myeloid cells are derived from the bone marrow or are tissue-resident. In certain embodiments, a lineage and/or clonal structure is determined for T cells, thereby determining the clonal relatedness of the T cells. In certain embodiments, the T cells are obtained from a subject undergoing an immune response. Thus, a specific application of the present invention is determining the clonal relatedness of immune cells, either of the myeloid or lymphoid lineage. The method can be used to determine if myeloid cells are derived from the bone marrow or are tissue-resident. The information can also be used to determine the clonal relatedness of T-cells mounting an immune response. The method can be used to determine both at the same time.

In certain embodiments, a lineage and/or clonal structure is determined for cells obtained from an in vivo model of cancer before, during, or after induction of cancer. In certain embodiments, the cells comprise pre-malignant stem cells.

In certain embodiments, the somatic mutations detected are detected in at least 5 sequencing reads and have at least 0.5% heteroplasmy in the single cells obtained from the subject. In certain embodiments, the mutations have at least 5% heteroplasmy in the single cells obtained from the subject.

In certain embodiments, the method further comprises sequencing mitochondrial genomes in a bulk sample obtained from the subject. Detecting mutations in a bulk sample may be used to select mutations used to determine a lineage or clonal structure. In certain embodiments, the somatic mutations detected are detected in at least 5 sequencing reads and have at least 0.5% heteroplasmy in a bulk sample obtained from the subject. In certain embodiments, the bulk sequencing comprises ATAC-seq, DNA-seq, RNA-seq, or RCA-seq. In certain embodiments, DNA-seq comprises whole genome, whole exome or targeted sequencing.

In certain embodiments, the mutations are detected in the D loop of the mitochondrial genomes. In certain embodiments, the detected mitochondrial mutations have a Phred quality score greater than 20. In certain embodiments, the clustering is hierarchical clustering. In certain embodiments, the method further comprises generating a lineage map.

In certain embodiments, nuclei isolated from the single cells are used. In certain embodiments, nuclei are isolated from frozen tissue samples. In certain embodiments, nuclei are isolated under conditions that enhance recovery of mitochondria.

In certain embodiments, single cells are lysed under conditions that release mitochondrial transcripts. In certain embodiments, the lysing conditions comprise one or more of NP-40, Triton X-100, SDS, guanidine isothiocyanate, guanidine hydrochloride or guanidine thiocyanate.

In certain embodiments, the method further comprises excluding RNA modifications, RNA transcription errors and/or RNA sequencing errors from the mutations detected. In certain embodiments, the RNA modifications comprise previously identified RNA modifications. In certain embodiments, RNA modifications, RNA transcription errors and/or RNA sequencing errors are determined by comparing the mutations detected in the cDNA library to mutations detected by DNA-seq, ATAC-seq or RCA-seq in a bulk sample from the subject.

In certain embodiments, the subject is a mammal.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 16A. Schematic depicts experimental overview for enriching mitochondrial transcripts from a single cell WTA library and identifying variants. FIG. 16B. Schematic of the mitochondrial genome with primer design locations indicated on the outside.

FIG. 19A. Heatmap showing the variant allele frequency between single cells in the mixing experiment depicted in FIG. 17. FIG. 19B. Clustering of the cells sequenced in FIG. 17 by RNA expression and mitochondrial DNA variants.

Figure 1:
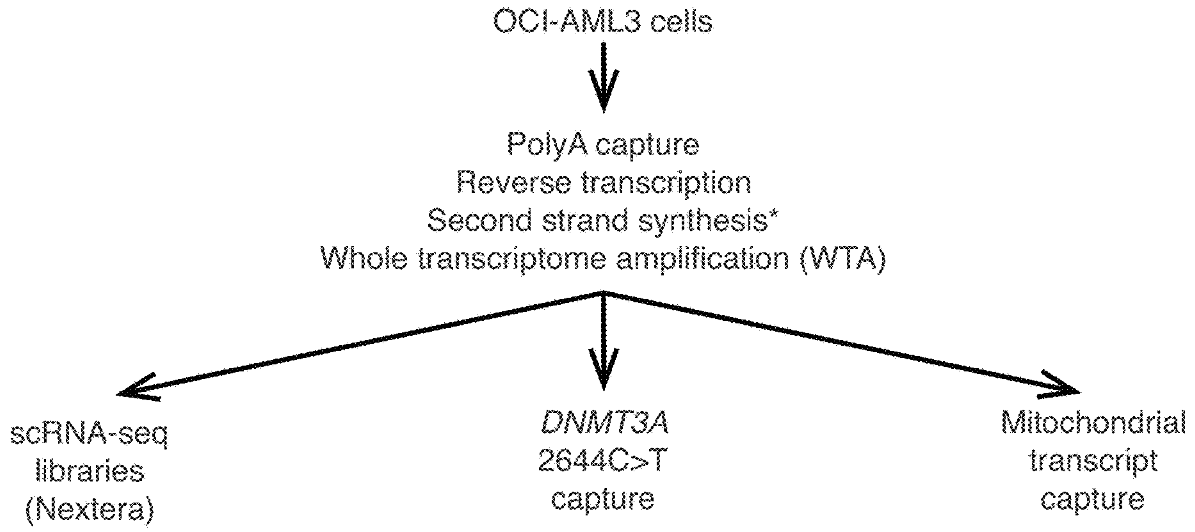
FIG. 1—Schematic depicts experimental overview for acquiring transcriptional, genotypic, and lineage and/or clonal structure information from high-throughput single cell RNA-seq libraries. An improved Seq-well protocol (Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273) is used to generate whole transcriptome amplification (WTA) products for single cells obtained from an AML patient, wherein each transcript cDNA is appended to a unique molecular identifier (UMI), a cell-specific barcode (CB), and a primer binding site (SMART). This WTA product is then split and used as starting material for transposase (Tn5)-mediated scRNA-seq library generation (left), readout of nuclear genome driver mutations (center), and readout of mitochondrial genome mutations (right). Nano-well plates and beads with barcoded adaptors are used to generate whole transcriptome amplification (WTA) products.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to Ludwig, et al., Lineage Tracing in Humans Enabled by Mitochondrial Mutations and Single-Cell Genomics, Cell. 2019 Mar. 7; 176 (6): 1325-1339.e22. doi: 10.1016/j.cell.2019.01.022. Epub 2019 Feb. 28; and van Galen, et al., Single-Cell RNA-Seq Reveals AML Hierarchies Relevant to Disease Progression and Immunity, Cell. 2019 Mar. 7; 176 (6): 1265-1281.e24. doi: 10.1016/j.cell.2019.01.031. Epub 2019 Feb. 28. Reference is also made to International Patent Application Nos. PCT/US2018/057170, filed Oct. 23, 2018 and published as WO2019/084055; PCT/US2018/057161, filed Oct. 23, 2018 and published as WO2019/084046; and PCT/US2019/036583, filed Jun. 11, 2019 and published as WO2019241273A1. All publications, published patent documents, and patent applications cited herein are hereby incorporated by reference to the same extent as though each individual publication, published patent document, or patent application was specifically and individually indicated as being incorporated by reference.

Overview

Prior studies have shown the utility of using mitochondrial mutations to generate a cell lineage (Ludwig, et al., Lineage Tracing in Humans Enabled by Mitochondrial Mutations and Single-Cell Genomics, Cell. 2019 Mar. 7; 176 (6): 1325-1339.e22). However, efficient methods are required to detect the mutations in high throughput single cell libraries. Embodiments disclosed herein provide methods of using somatic mitochondrial mutations detected in high throughput single cell RNA sequencing libraries to retrospectively infer cell lineages in native contexts and to serve as genetic barcodes to measure clonal dynamics in complex cellular populations. Further, embodiments disclosed herein provide methods to detect mitochondrial mutations, nuclear genome mutations, and transcriptomes all from the WTA product generated during single cell RNA-seq. Applicants provide improved methods to use the WTA product from high throughput single cell RNA sequencing. The method advantageously enriches mitochondrial transcripts from the WTA product for detection of mutations that can be used to infer a lineage or clonal structure for single cells. With a minimum of two reads per transcript, mitochondrial coverage is increased from 1.18 to 26.2-fold on average for every single cell. Disclosed methods provide for enrichment by amplification with primers specific to the mitochondrial genome. The methods are for the first time compatible with high-throughput single-cell RNA-sequencing protocols (droplet or microwells, i.e. Seq-Well, Drop-Seq, 10×).

Lineage tracing provides unprecedented insights into the fate of individual cells and their progeny in complex organisms. While effective genetic approaches have been developed in vitro and in animal models, these cannot be used to interrogate human physiology in vivo. Instead, naturally occurring somatic mutations have been utilized to infer clonality and lineal relationships between cells in human tissues, but current approaches are limited by high error rates and scale, and provide little information about the state or function of the cells. Here, Applicants show how somatic mutations in mitochondrial DNA (mtDNA) detected in high throughput single cell RNA-seq libraries can be tracked for simultaneous analysis of single cell lineage and state.

Mitochondrial Genomes

Mitochondria are dynamic organelles that are present in almost all eukaryotic cells and play a crucial role in several cellular pathways (see, e.g., Taanman, Biochimica et Biophysica Acta (BBA)-Bioenergetics, Volume 1410, Issue 2, 9 Feb. 1999, Pages 103-123). The human mitochondrial DNA (mtDNA) is a double-stranded, circular molecule of 16,569 bp and contains 37 genes coding for two rRNAs, 22 tRNAs and 13 polypeptides. These mRNAs are transcribed and then translated within the mitochondrial matrix by a dedicated, unique, and highly specialized machinery. Mitochondrial mRNAs are polyadenylated by a mitochondrial poly (A) polymerase during or immediately after cleavage, whereas the 3'-ends of the two rRNAs are post-transcriptionally modified by the addition of only short adenyl stretches. Somatic mutations in the mitochondrial genome (mtDNA) provide a compelling alternative for determining lineages and clonal structure (R. W. Taylor et al., Mitochondrial DNA mutations in human colonic crypt stem cells. *J Clin Invest* 112, 1351-1360 (2003); and V. H. Teixeira et al., Stochastic homeostasis in human airway epithelium is achieved by neutral competition of basal cell progenitors. Elife 2, e00966 (2013)), as multiple studies have shown that each human cell contains hundreds-to-thousands of mitochondrial genomes with diverse and often manifold mutations at detectable levels of heteroplasmy (Y. G. Yao et al., Accumulation of mtDNA variations in human single CD34+ cells from maternally related individuals: effects of aging and family genetic background. *Stem Cell Res* 10, 361-370 (2013); E. Kang et al., Age-Related Accumulation of Somatic Mitochondrial DNA Mutations in Adult-Derived Human iPSCs. *Cell Stem Cell* 18, 625-636 (2016); M. Li, R. Schroder, S. Ni, B. Madea, M. Stoneking, Extensive tissue-related and allele-related mtDNA heteroplasmy suggests positive selection for somatic mutations. *Proc Natl Acad Sci USA* 112, 2491-2496 (2015); and K. Ye, J. Lu, F. Ma, A. Keinan, Z. Gu, Extensive pathogenicity of mitochondrial heteroplasmy in healthy human individuals. *Proc Natl Acad Sci* U SA 111, 10654-10659 (2014)).

Sequencing

In certain embodiments, sequencing comprises high-throughput (formerly "next-generation") technologies to generate sequencing reads. In DNA sequencing, a read is an inferred sequence of base pairs (or base pair probabilities) corresponding to all or part of a single DNA fragment. A typical sequencing experiment involves fragmentation of the genome into millions of molecules or generating complementary DNA (cDNA) fragments, which are size-selected and ligated to adapters. The set of fragments is referred to as a sequencing library, which is sequenced to produce a set of reads. Methods for constructing sequencing libraries are known in the art (see, e.g., Head et al., Library construction for next-generation sequencing: Overviews and challenges. *Biotechniques.* 2014; 56 (2): 61-77; and Trombetta, J. J., Gennert, D., Lu, D., Satija, R., Shalek, A. K. & Regev, A. Preparation of Single-Cell RNA-Seq Libraries for Next Generation Sequencing. *Curr Protoc Mol Biol.* 107, 4 22 21-24 22 17, doi: 10.1002/0471142727.mb0422s107 (2014). PMCID: 4338574). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., genomic DNA, cDNA) may include sequencing adaptors that are compatible with use in, e.g., Illumina's reversible terminator method, long read nanopore sequencing, Roche's pyrosequencing method (454), Life Technologies' sequencing by ligation (the SOLID platform) or Life Technologies' Ion Torrent platform. Examples of such methods are described in the following references: Margulies et al (Nature 2005 437:376-80); Schneider and Dekker (Nat Biotechnol. 2012 Apr. 10; 30 (4): 326-8); Ronaghi et al (Analytical Biochemistry 1996 242:84-9); Shendure et al (Science 2005 309:1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92: 25S-64), which are incorporated by reference for the general descriptions of the methods and the particular steps of the methods, including all starting products, reagents, and final products for each of the steps.

In certain embodiments, the present invention includes whole genome sequencing. Whole genome sequencing (also known as WGS, full genome sequencing, complete genome sequencing, or entire genome sequencing) is the process of determining the complete DNA sequence of an organism's genome at a single time. This entails sequencing all of an organism's chromosomal DNA as well as DNA contained in the mitochondria and, for plants, in the chloroplast. "Whole genome amplification" ("WGA") refers to any amplification method that aims to produce an amplification product that is representative of the genome from which it was amplified. Non-limiting WGA methods include Primer extension PCR (PEP) and improved PEP (I-PEP), Degenerated oligonucleotide primed PCR (DOP-PCR), Ligation-mediated PCR (LMP), T7-based linear amplification of DNA (TLAD), and Multiple displacement amplification (MDA).

In certain embodiments, the present invention includes whole exome sequencing. Exome sequencing, also known as whole exome sequencing (WES), is a genomic technique for sequencing all of the protein-coding genes in a genome (known as the exome) (see, e.g., Ng et al., 2009, Nature volume 461, pages 272-276). It consists of two steps: the first step is to select only the subset of DNA that encodes proteins. These regions are known as exons-humans have about 180,000 exons, constituting about 1% of the human genome, or approximately 30 million base pairs. The second step is to sequence the exonic DNA using any high-throughput DNA sequencing technology. In certain embodiments, whole exome sequencing is used to determine somatic mutations in genes associated with disease (e.g., cancer mutations).

In certain embodiments, targeted sequencing is used in the present invention (see, e.g., Mantere et al., PLoS Genet 12 e1005816 2016; and Carneiro et al. BMC Genomics, 2012 13:375). Targeted gene sequencing panels are useful tools for analyzing specific mutations in a given sample. Focused panels contain a select set of genes or gene regions that have known or suspected associations with the disease or phenotype under study. In certain embodiments, targeted sequencing is used to detect mutations associated with a disease in a subject in need thereof. Targeted sequencing can increase the cost-effectiveness of variant discovery and detection.

Figure 10:
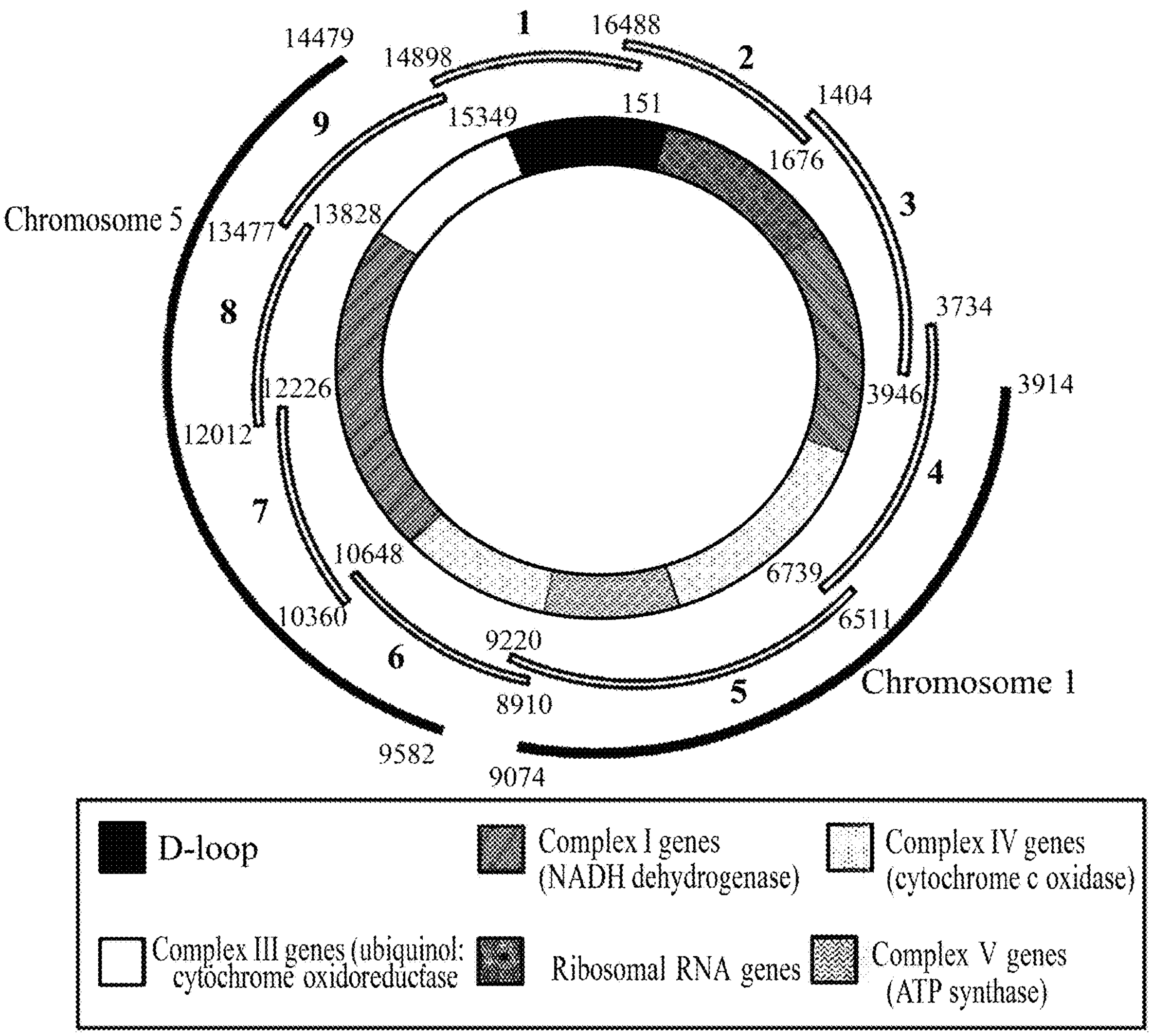
FIG. 10—Bulk mtDNA amplification by amplicon approach. Schematic representation of mtDNA. The nine overlapping fragments defined to PCR amplify the complete mtDNA genome are represented as well as the two nuclear regions with high homology with mtDNA (see, Electrophoresis 2009, 30, 1587-1593).
Figure 11:
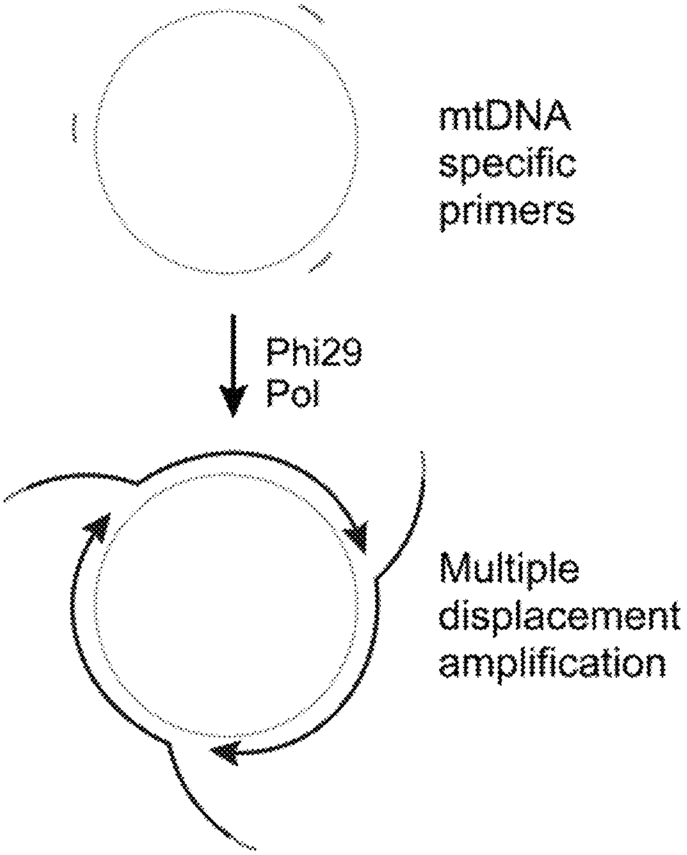
FIG. 11—Bulk mtDNA amplification by rolling circle (RCA) approach. Schematic showing mtDNA specific primers and multiple displacement amplification.

In certain embodiments, the mitochondrial genome is specifically sequenced in a bulk sample using MitoRCA-seq (see e.g., Ni et al., MitoRCA-seq reveals unbalanced cytosine to thymine transition in Polg mutant mice. Sci Rep. 2015 Jul. 27; 5:12049. doi: 10.1038/srep12049). The method employs rolling circle amplification, which enriches the full-length circular mtDNA by either custom mtDNA-specific primers or a commercial kit, and minimizes the contamination of nuclear encoded mitochondrial DNA (Numts). In certain embodiments, RCA-seq is used to detect low-frequency mtDNA point mutations starting with as little as 1 ng of total DNA. In certain embodiments, mitochondrial DNA is sequenced using amplification by the amplicon approach (FIG. 10). In certain embodiments, mitochondrial DNA is sequenced using amplification by the rolling circle (RCA) approach (FIG. 11).

In certain embodiments, single cell Mito-seq (scMito-seq) is used to sequence the mitochondrial genome in single cells. The method is based on performing rolling circle amplification of mitochondrial genomes in single cells.

In certain embodiments, multiple displacement amplification (MDA) is used to generate a sequencing library (e.g., single cell genome sequencing). Multiple displacement amplification (MDA), is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

In certain embodiments, the invention involves the Assay for Transposase Accessible Chromatin sequencing (ATAC-seq) or single cell ATAC-seq as described (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science.* 2015 May 22; 348 (6237): 910-4. doi: 10.1126/science.aab1601. Epub 2015 May 7; US20160208323A1; US20160060691A1; and WO2017156336A1). The term "tagmentation" refers to a step in the Assay for Transposase Accessible Chromatin using sequencing (ATAC-seq) as described. Specifically, a hyperactive Tn5 transposase loaded in vitro with adapters for high-throughput DNA sequencing, can simultaneously fragment and tag a genome with sequencing adapters. In certain embodiments, ATAC-seq is used on a bulk DNA sample to determine mitochondrial mutations.

In certain embodiments, a transcriptome is sequenced. The transcriptome may be used to genotype nuclear and mitochondrial genomes in addition to determining gene expression. As used herein the term "transcriptome" refers to the set of transcripts molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the present invention involves single cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International Patent Application No. PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International Patent Application No. PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12 (1): 44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14 (3): 302-308, 2017; Cao, et al., Comprehensive single-cell transcriptional profiling of a multicellular organism. Science, 357 (6352): 661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the method of measuring mitochondrial mutations, nuclear genome mutations, and gene expression are all performed using a high-throughput single cell RNA sequencing library (e.g., scRNA-seq, Seq-well). The methods described herein are specifically designed for compatibility with high-throughput single-cell RNA-sequencing protocols (droplet or microwells, i.e. Seq-Well, Drop-Seq, 10×). In some embodiments, the library comprises transcripts from a plurality of cells. In some embodiments, a plurality of cells comprises about 100, 500, 1,000, 10,000, 20,000. 30,000, 40,000, 50,000, 60,000, 70,000, 80,000, 90,000, 100,000, 200,000, 300,000, 400,000, 500, 000, 600,000, 700,000, 800,000, 900,000 or 1,000,000 or more cells. In some embodiments, the library is prepared using any method described herein, e.g., the Seq-Well, InDrop, Drop-Seq, or 10× Genomics methods and a plurality of cells comprises between 10,000 and 1,000,000 cells, e.g., 20,000-100,000 cells.

Figure 19A:
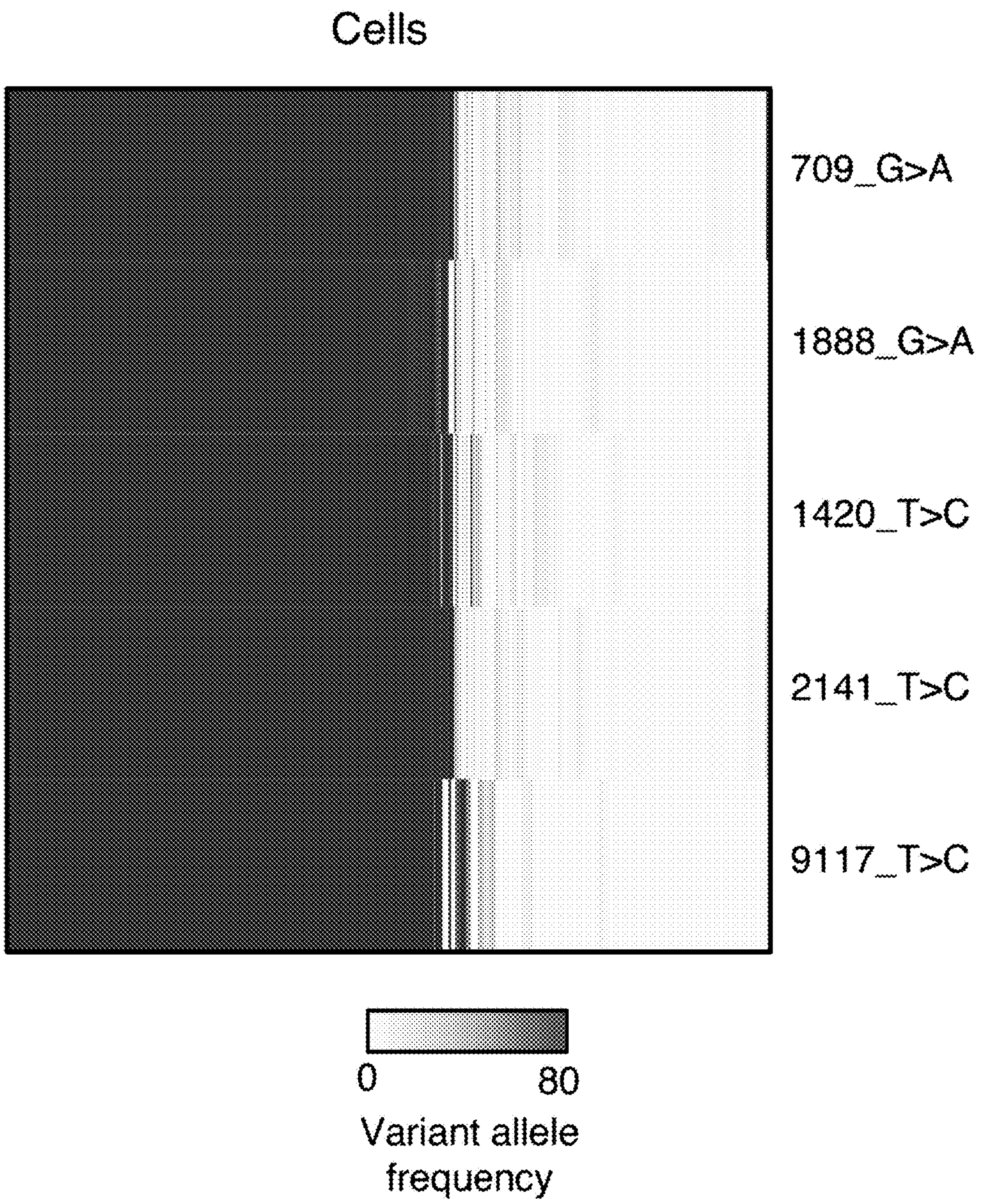
FIG. 19A-FIG. 19B—Cell identity from mitochondrial variants.
Figure 19B:
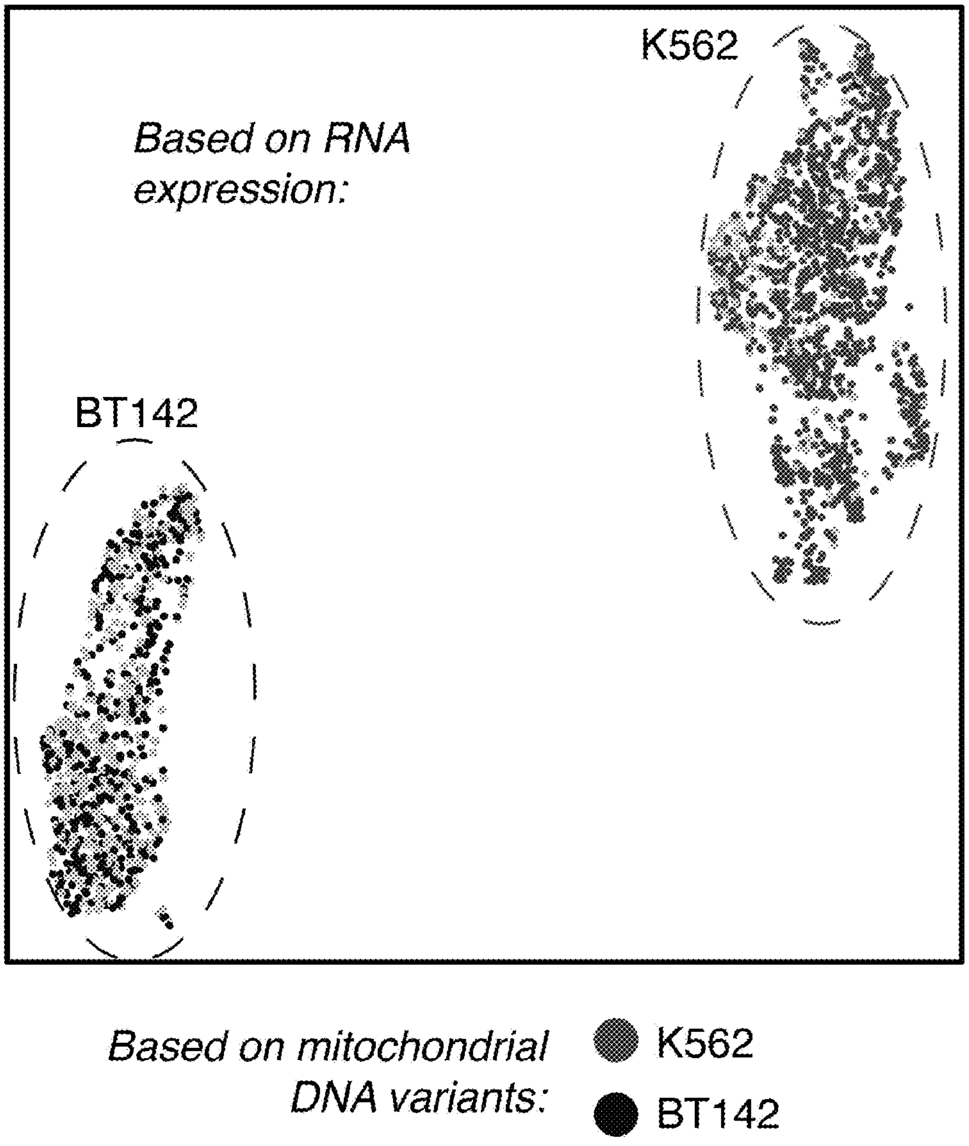

In certain embodiments, the invention involves RNA sequencing. In certain embodiments, the RNA sequencing is single cell RNA-sequencing. In certain embodiments, a cDNA library is generated. The cDNA library may be used to generate sequencing libraries for determining mutations in the mitochondrial genome (genotyping), the nuclear genome (genotyping), or for determining gene expression (RNA-seq) (see, e.g., WO 2019/084055 FIG. 19A). For example, the RNA-seq library is generated using tagmentation and the sequencing reads are 3' biased for identification of the gene only. For genotyping, the target sequence containing a site of interest is enriched and the sequencing reads include the target region. In the case of genotyping the mitochondrial genome, enrichment of all sites in the mitochondrial genome can be enriched by performing PCR enrichment using the primers disclosed herein (see, Table 1).

In certain embodiments, whole transcriptome amplification (WTA) is used to generate the cDNA library. The cDNA library may also be referred to as the whole transcriptome amplification (WTA) library. The library may include "WTA products". "Whole transcriptome amplification" ("WTA") refers to any amplification method that aims to produce an amplification product that is representative of a population of RNA from the cell from which it was prepared. An illustrative WTA method entails production of cDNA bearing linkers on either end that facilitate unbiased amplification. In many implementations, WTA is carried out to analyze messenger (poly-A) RNA (this is also referred to as "RNAseq"). WTA may include reverse transcription (RT) to generate first strand cDNA. First strand synthesis may be followed by second strand synthesis. First strand synthesis may include priming of the RT on a 3' adaptor linked to the RNA molecules. In certain embodiments, each RNA in a library may be amplified to create a whole transcriptome amplified (WTA) RNA by reverse transcription with a primer comprising a sequence adapter. The reverse transcribed product may be amplified by PCR amplification with primers that bind both 5' and 3' sequence adapters. In certain embodiments, the amplified RNA comprises the orientation: 5'-sequencing adapter-cell barcode-UMI-UUUUUUU-mRNA-3'. In some embodiments, PCR amplification is conducted on the reverse transcribed products with primers that bind both sequence adapters and adding a library barcode and optionally additional sequence adapters.

In certain embodiments, the invention involves single nucleus RNA sequencing. In this regard, reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14 (10): 955-958; International patent application number PCT/US2016/059239, published as WO2017164936 on Sep. 28, 2017; International patent application number PCT/US2018/060860, published as WO/2019/094984 on May 16, 2019; International patent application number PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In certain embodiments, any suitable RNA or DNA amplification technique may be used. In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

In certain embodiments, cells to be sequenced according to any of the methods herein are lysed under conditions specific to sequencing mitochondrial genomes. In certain embodiments, lysis using mild conditions does not result in sequencing of all of the mitochondrial genomes. In certain embodiments, use of harsher lysing conditions allows for increase sequencing of mitochondrial genomes due to improved lysis of mitochondria. In certain embodiments, lysis buffers include one or more of NP-40, Triton X-100, SDS, guanidine isothiocyante, guanidine hydrochloride or guanidine thiocyanate. The use of more stringent lysis may not affect the nuclear genome transcripts.

In certain embodiments, the sequencing cost is lower in sequencing mitochondrial genomes because of the size of the mitochondrial genome. The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell).

The term "ultra-deep" as used herein refers to higher coverage (>100-fold), which allows for detection of sequence variants in mixed populations.

Barcodes and Unique Molecular Identifiers

The present invention may encompass incorporation of a unique molecular identifier (UMI) (see, e.g., Kivioja et al., 2012, Nat. Methods. 9 (1): 72-4 and Islam et al., 2014, Nat. Methods. 11 (2): 163-6) a unique cell barcode (cell BC) into the library, or both. The cell barcode as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment.

Barcoding may be performed based on any of the compositions or methods disclosed in International Patent Publication No. WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. Unique Molecular Identifiers may be short (usually 4-10 bp) random barcodes added to transcripts during reverse-transcription. They enable sequencing reads to be assigned to individual transcript molecules and thus the removal of amplification noise and biases from RNA-seq data. The UMI may also be used to determine the number of transcripts that gave rise to an amplified product.

Enrichment of cDNA for Genotyping

In certain embodiments, transcripts of interest may be enriched for determining genotypes (e.g., somatic mutations). A transcript of interest may also be interchangeably referred to as a gene of interest or target sequence. Target sequence can refer to any polynucleotide, such as DNA or RNA polynucleotides. In some embodiments, a target sequence is derived from the nucleus or cytoplasm of a cell, and may include nucleic acids in or from mitochondrial, organelles, vesicles, liposomes or particles present within the cell. Nucleic acid enrichment reduces the complexity of a large nucleic acid sample, such as a genomic DNA sample, cDNA library or mRNA library, to facilitate further processing and genetic analysis. Nucleic acid enrichment may also provide a means for obtaining size selected sequencing library molecules that include barcode sequences and the target sequence. Nucleic acid enrichment may also provide for a sequencing library with reduced complexity such that the sequencing reads allow identification of somatic mutations. In some embodiments, enrichment of the gene, region or mutation of interest is required to efficiently and confidently call genetic mutations. The present invention provides for enrichment of mitochondrial genome transcripts from high throughput RNA sequencing libraries such that mutations are efficiently and confidently called.

A gene of interest may comprise, for example, a mutation, deletion, insertion, translocation, single nucleotide polymorphism (SNP), splice variant or any combination thereof associated with a particular attribute in a gene of interest. In another embodiment, the gene of interest may be a cancer gene. In another embodiment, the gene of interest is a mutated cancer gene, such as a somatic mutation. In another embodiment, the gene of interest is a mitochondrial gene. In another embodiment, the gene of interest is a mitochondrial gene having a somatic mutation used to obtain a lineage and/or clonal structure for single cells.

Any gene, region or mutation of interest can be included in the enriched libraries. The enriched libraries can be used to identify cells containing specific genes, regions or mutations, deletions, insertions, indels, or translocations of interest. A gene of interest may be, for example, a cancer gene, in particular a mutation in a cancer gene. The mutation may be one or more somatic mutations found in cancer and may be listed, for example, in the Catalogue of Somatic Mutations in Cancer (COSMIC) database (see, e.g., cancer-.sanger.ac.uk/cosmic/).

In some instances, the mutation is located anywhere in the gene. In some instances, the desired transcript can be greater than about 1 kb away from the cell barcode of the nucleic acid of the libraries as described herein. The gene of interest may comprise a SNP.

As the methods herein can be designed to distinguish SNPs within a population, the methods may be used to distinguish pathogenic strains that differ by a single SNP or detect certain disease specific SNPs, such as but not limited to, disease associated SNPs, such as without limitation cancer associated SNPs.

The gene of interest, transcript of interest, in some instances comprises a mutation. The mutation may be within 1 kilobase of the polyA tail of an mRNA in the library. A library of enriched single cell RNA transcripts is provided and may comprise a plurality of nucleic acids comprising a cell barcode and unique molecular identifier in close proximity to a desired transcript of interest, the plurality of nucleic acids derived from a 3'barcoded single cell RNA library, wherein at least a subset of the plurality of nucleic acids in the library comprise transcripts of interest that were within 1 kilobase or greater than 1 kb away from the cell barcode in the 3' barcoded single cell RNA library.

Figure 4:
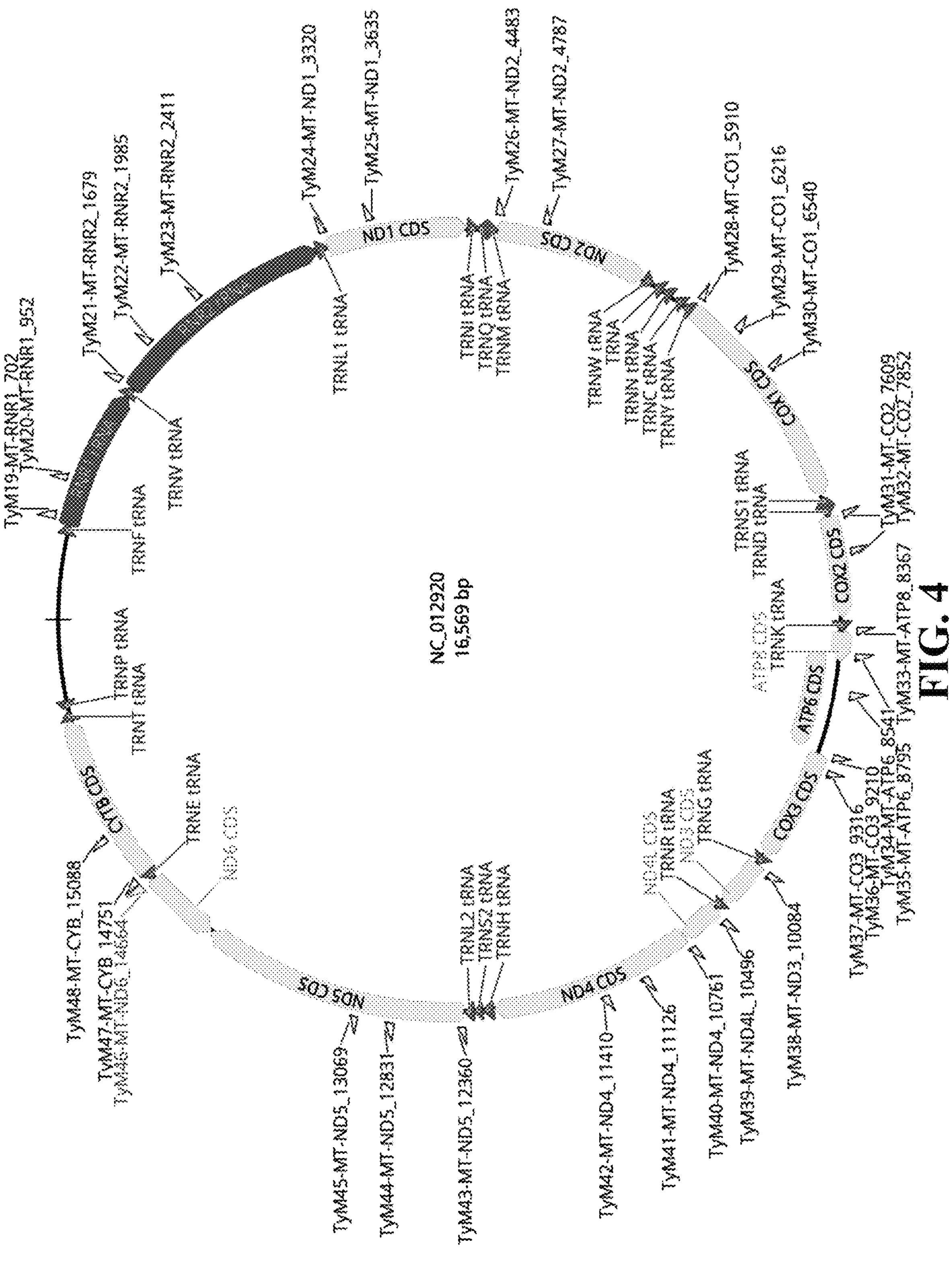
FIG. 4—Primer design for mitochondrial transcript capture. Schematic of the mitochondrial genome with primer design locations indicated on the outside.

In the case of genotyping the mitochondrial genome, all sites in the mitochondrial genome can be enriched by performing PCR enrichment. Example forward primers are disclosed in Table 1. Enrichment can be performed with primers in Table 1 and a universal reverse primer specific for an adaptor sequence (e.g., SMART sequences added during Seq-well) (Table 1 and FIG. 4). Example primers for enrichment of mitochondrial transcripts from single cell libraries are also disclosed in Table 2 (Table 2). The primers may be separated into mixes to be used for different enrichment reactions, as discussed further in the examples.

TABLE 1

Primers for enriching mitochondrial transcripts and primer characteristics.

| SEQ ID NO | Sequence (5'→3') | Gene | Description | Template strand | Length | Start | Stop |
|---|---|---|---|---|---|---|---|
| 1 | TGGTCCTAGCCTTTCTATTAGCTC | MT-RNR1 | 12s rRNA | Plus | 24 | 656 | 679 |
| 2 | GCGGTCACACGATTAACCCA | MT-RNR1 | 12s rRNA | Plus | 20 | 899 | 918 |
| 3 | ACTGCTCGCCAGAACACTAC | MT-RNR1 | 12s rRNA | Plus | 20 | 1127 | 1146 |
| 4 | GGTGGCAAGAAATGGGCTACA | MT-RNR1 | 12s rRNA | Plus | 21 | 1347 | 1367 |
| 5 | TAGCCCCAAACCCACTCCAC | MT-RNR2 | 16S rRNA | Plus | 20 | 1679 | 1698 |
| 6 | CTAAGACCCCCGAAACCAGA | MT-RNR2 | 16S rRNA | Plus | 20 | 1895 | 1914 |
| 7 | ACAGCTCTTTGGACACTAGGAA | MT-RNR2 | 16S rRNA | Plus | 22 | 2110 | 2131 |
| 8 | ATTCTCCTCCGCATAAGCCTG | MT-RNR2 | 16S rRNA | Plus | 21 | 2323 | 2343 |
| 9 | ACCAGTATTAGAGGCACCGC | MT-RNR2 | 16S rRNA | Plus | 20 | 2524 | 2543 |
| 10 | AGTACCTAACAAACCCACAGGTC | MT-RNR2 | 16S rRNA | Plus | 23 | 2757 | 2779 |
| 11 | CCTCGATGTTGGATCAGGAC | MT-RNR2 | 16S rRNA | Plus | 20 | 2985 | 3004 |
| 12 | ACCTCCTACTCCTCATTGTACCC | MT-ND1 | NADH dehydrogenase, subunit 1 | Plus | 23 | 3320 | 3342 |
| 13 | AGCTCTCACCATCGCTCTTC | MT-ND1 | NADH dehydrogenase, subunit 1 | Plus | 20 | 3537 | 3556 |
| 14 | TGGCTCCTTTAACCTCTCCAC | MT-ND1 | NADH dehydrogenase, subunit 1 | Plus | 21 | 3777 | 3797 |
| 15 | AACACCCTCACCACTACAATCT | MT-ND1 | NADH dehydrogenase, subunit 1 | Plus | 22 | 4009 | 4030 |
| 16 | CCCAACCCGTCATCTACTCTAC | MT-ND2 | NADH dehydrogenase, subunit 2 | Plus | 22 | 4483 | 4504 |
| 17 | CCGGACAATGAACCATAACCAA | MT-ND2 | NADH dehydrogenase, subunit 2 | Plus | 22 | 4711 | 4732 |
| 18 | AGCCTTCTCCTCACTCTCTCAA | MT-ND2 | NADH dehydrogenase, subunit 2 | Plus | 22 | 4923 | 4944 |
| 19 | ACGACCCTACTACTATCTCGCA | MT-ND2 | NADH dehydrogenase, subunit 2 | Plus | 22 | 5145 | 5166 |
| 20 | CTCCACCTCAATCACACTACTCC | MT-ND2 | NADH dehydrogenase, subunit 2 | Plus | 23 | 5363 | 5385 |
| 21 | GCCGACCGTTGACTATTCTCT | MT-CO1 | Cytochrome C Oxidase I | Plus | 21 | 5910 | 5930 |
| 22 | TAATCGGAGGCTTTGGCAACT | MT-CO1 | Cytochrome C Oxidase I | Plus | 21 | 6124 | 6144 |
| 23 | GCCTCCGTAGACCTAACCATC | MT-CO1 | Cytochrome C Oxidase I | Plus | 21 | 6324 | 6344 |
| 24 | TCAACACCACCTTCTTCGACC | MT-CO1 | Cytochrome C Oxidase I | Plus | 21 | 6547 | 6567 |
| 25 | TTGGCTTCCTAGGGTTTATCGTG | MT-CO1 | Cytochrome C Oxidase I | Plus | 23 | 6742 | 6764 |
| 26 | GGCCTGACTGGCATTGTATT | MT-CO1 | Cytochrome C Oxidase I | Plus | 20 | 6957 | 6976 |
| 27 | ACAACACTTTCTCGGCCTATCC | MT-CO1 | Cytochrome C Oxidase I | Plus | 22 | 7184 | 7205 |
| 28 | TCTACAAGACGCTACTTCCCC | MT-CO2 | Cytochrome C Oxidase II | Plus | 21 | 7609 | 7629 |

TABLE 1-continued

| Primers for enriching mitochondrial transcripts and primer characteristics. | | | | | | | |
|---|---|---|---|---|---|---|---|
| 29 | ACATAACAGACGAGGTCAACGA | MT-CO2 | Cytochrome C Oxidase II | Plus | 22 | 7839 | 7860 |
| 30 | ATGAGCTGTCCCCACATTAGG | MT-CO2 | Cytochrome C Oxidase II | Plus | 21 | 8071 | 8091 |
| 31 | TGCCCCAACTAAATACTACCG | MT-ATP8 | ATP synthase 8 | Plus | 21 | 8367 | 8387 |
| 32 | GTTCGCTTCATTCATTGCCCC | MT-ATP6 | ATP synthase 6 | Plus | 21 | 8541 | 8561 |
| 33 | CACAACTAACCTCCTCGGACT | MT-ATP6 | ATP synthase 6 | Plus | 21 | 8766 | 8786 |
| 34 | CTGGCCGTACGCCTAACC | MT-ATP6 | ATP synthase 6 | Plus | 18 | 8992 | 9009 |
| 35 | ACCCACCAATCACATGCCTATC | MT-CO3 | Cytochrome C Oxidase III | Plus | 22 | 9210 | 9231 |
| 36 | TCCACTCCATAACGCTCCTC | MT-CO3 | Cytochrome C Oxidase III | Plus | 20 | 9316 | 9335 |
| 37 | CCCAATTAGGAGGGCACTGG | MT-CO3 | Cytochrome C Oxidase III | Plus | 20 | 9535 | 9554 |
| 38 | TCTCCCTTCACCATTTCCGAC | MT-CO3 | Cytochrome C Oxidase III | Plus | 21 | 9756 | 9776 |
| 39 | TCAACACCCTCCTAGCCTTAC | MT-ND3 | NADH dehydrogenase, subunit 3 | Plus | 21 | 10084 | 10104 |
| 40 | TTGCCCTCCTTTTACCCCTAC | MT-ND3 | NADH dehydrogenase, subunit 3 | Plus | 21 | 10264 | 10284 |
| 41 | ACTAGCATTTACCATCTCACTTCT | MT-ND4L | NADH dehydrogenase, subunit 4L | Plus | 24 | 10496 | 10519 |
| 42 | TGCTAAAACTAATCGTCCCAACAA | MT-ND4 | NADH dehydrogenase, subunit 4 | Plus | 24 | 10761 | 10784 |
| 43 | GCAAGCCAACGCCACTTATC | MT-ND4 | NADH dehydrogenase, subunit 4 | Plus | 20 | 10994 | 11013 |
| 44 | TAGGCTCCCTTCCCCTACTC | MT-ND4 | NADH dehydrogenase, subunit 4 | Plus | 20 | 11223 | 11242 |
| 45 | TAAAGCCCATGTCGAAGCCC | MT-ND4 | NADH dehydrogenase, subunit 4 | Plus | 20 | 11410 | 11429 |
| 46 | ACGCCTCACACTCATTCTCAA | MT-ND4 | NADH dehydrogenase, subunit 4 | Plus | 21 | 11491 | 11511 |
| 47 | TTCACCGGCGCAGTCATT | MT-ND4 | NADH dehydrogenase, subunit 4 | Plus | 18 | 11684 | 11701 |
| 48 | GTGCTAGTAACCACGTTCTCCT | MT-ND4 | NADH dehydrogenase, subunit 4 | Plus | 22 | 11900 | 11921 |
| 49 | CACCCTAACCCTGACTTCCC | MT-ND5 | NADH dehydrogenase, subunit 5 | Plus | 20 | 12360 | 12379 |
| 50 | TTCATCCCTGTAGCATTGTTCGT | MT-ND5 | NADH dehydrogenase, subunit 5 | Plus | 23 | 12601 | 12623 |
| 51 | CACAGCAGCCATTCAAGCAA | MT-ND5 | NADH dehydrogenase, subunit 5 | Plus | 20 | 12831 | 12850 |
| 52 | GCCCTACTCCACTCAAGCAC | MT-ND5 | NADH dehydrogenase, subunit 5 | Plus | 20 | 13069 | 13088 |
| 53 | GGCATCAACCAACCACACCT | MT-ND5 | NADH dehydrogenase, subunit 5 | Plus | 20 | 13288 | 13307 |
| 54 | CCACATCATCGAAACCGCAAA | MT-ND5 | NADH dehydrogenase, subunit 5 | Plus | 21 | 13515 | 13535 |
| 55 | ACTAACAACATTTCCCCCGCA | MT-ND5 | NADH dehydrogenase, subunit 5 | Plus | 21 | 13741 | 13761 |
| 56 | TAGCATCACACACCGCACAA | MT-ND5 | NADH dehydrogenase, subunit 5 | Plus | 20 | 13926 | 13945 |
| 57 | GCTTTGTTTCTGTTGAGTGTGG | MT-ND6 | NADH dehydrogenase, subunit 6 | Minus | 22 | 14664 | 14643 |
| 58 | GGGGAATGATGGTTGTCTTTGG | MT-ND6 | NADH dehydrogenase, subunit 6 | Minus | 22 | 14492 | 14471 |
| 59 | GTCAGGGTTGATTCGGGAGG | MT-ND6 | NADH dehydrogenase, subunit 6 | Minus | 20 | 14281 | 14262 |
| 60 | CCCCAATACGCAAAACTAACCC | MT-CYB | cytochrome B | Plus | 22 | 14751 | 14772 |
| 61 | CATCAATCGCCCACATCACTC | MT-CYB | cytochrome B | Plus | 21 | 14937 | 14957 |
| 62 | CATCGGCATTATCCTCCTGCT | MT-CYB | cytochrome B | Plus | 21 | 15088 | 15108 |
| 63 | AGTCCCACCCTCACACGAT | MT-CYB | cytochrome B | Plus | 19 | 15260 | 15278 |
| 64 | CCCTCGGCTTACTTCTCTTCC | MT-CYB | cytochrome B | Plus | 21 | 15432 | 15452 |
| 65 | CATCCTAGCAATAATCCCCATCCT | MT-CYB | cytochrome B | Plus | 24 | 15643 | 15666 |
| 66 | CATCCCCGTTCCAGTGAGTT | MT-RNR1 | 12s rRNA | Plus | 20 | 702 | 721 |
| 67 | ATCACCCCCTCCCCAATAAAG | MT-RNR1 | 12s rRNA | Plus | 21 | 952 | 972 |

TABLE 1-continued

Primers for enriching mitochondrial transcripts and primer characteristics.

| | | | | | | | |
|---|---|---|---|---|---|---|---|
| 68 | GAGGCGACAAACCTACCGA | MT-RNR2 | 16S rRNA | Plus | 19 | 1985 | 2003 |
| 69 | TACCCTCACTGTCAACCCAAC | MT-RNR2 | 16S rRNA | Plus | 21 | 2411 | 2431 |
| 70 | GCCTAGCCGTTTACTCAATCCT | MT-ND1 | NADH dehydrogenase, subunit 1 | Plus | 22 | 3635 | 3656 |
| 71 | AGGAATAGCCCCCTTTCACTTC | MT-ND2 | NADH dehydrogenase, subunit 2 | Plus | 22 | 4787 | 4808 |
| 72 | TTACCTCCCTCTCTCCTACTCC | MT-CO1 | Cytochrome C Oxidase I | Plus | 22 | 6216 | 6237 |
| 73 | CGCAACCTCAACACCACCTT | MT-CO1 | Cytochrome C Oxidase I | Plus | 20 | 6540 | 6559 |
| 74 | GGTCAACGATCCCTCCCTTAC | MT-CO2 | Cytochrome C Oxidase 11 | Plus | 21 | 7852 | 7872 |
| 75 | ACTCATTTACACCAACCACCCA | MT-ATP6 | ATP synthase 6 | Plus | 22 | 8795 | 8816 |
| 76 | GAAACCACACTTATCCCCACCT | MT-ND4 | NADH dehydrogenase, subunit 4 | Plus | 22 | 11126 | 11147 |

| SEQ ID NO | Tm | GC % | Self complementarity | Self 3' complementarity | Expected transcript size (WTA) | mtTranscript Start | mtTranscript Stop | Transcript Size |
|---|---|---|---|---|---|---|---|---|
| 1 | 59.41 | 45.83 | 5 | 2 | 965 | 648 | 1601 | 953 |
| 2 | 60.67 | 55 | 4 | 1 | 722 | 648 | 1601 | 953 |
| 3 | 60.04 | 55 | 4 | 0 | 494 | 648 | 1601 | 953 |
| 4 | 60.89 | 52.38 | 3 | 0 | 274 | 648 | 1601 | 953 |
| 5 | 61.79 | 60 | 2 | 0 | 1570 | 1671 | 3229 | 1558 |
| 6 | 58.73 | 55 | 3 | 0 | 1354 | 1671 | 3229 | 1558 |
| 7 | 59.03 | 45.45 | 4 | 0 | 1139 | 1671 | 3229 | 1558 |
| 8 | 59.93 | 52.38 | 4 | 1 | 926 | 1671 | 3229 | 1558 |
| 9 | 59.54 | 55 | 3 | 2 | 725 | 1671 | 3229 | 1558 |
| 10 | 59.93 | 47.83 | 4 | 1 | 492 | 1671 | 3229 | 1558 |
| 11 | 57.77 | 55 | 4 | 1 | 264 | 1671 | 3229 | 1558 |
| 12 | 60.63 | 52.17 | 4 | 0 | 962 | 3307 | 4262 | 955 |
| 13 | 59.54 | 55 | 4 | 0 | 745 | 3307 | 4262 | 955 |
| 14 | 59.37 | 52.38 | 4 | 0 | 505 | 3307 | 4262 | 955 |
| 15 | 59.02 | 45.45 | 2 | 1 | 273 | 3307 | 4262 | 955 |
| 16 | 59.64 | 54.55 | 2 | 0 | 1048 | 4470 | 5511 | 1041 |
| 17 | 58.91 | 45.45 | 4 | 0 | 820 | 4470 | 5511 | 1041 |
| 18 | 60.23 | 50 | 3 | 0 | 608 | 4470 | 5511 | 1041 |
| 19 | 59.9 | 50 | 4 | 0 | 386 | 4470 | 5511 | 1041 |
| 20 | 60.12 | 52.17 | 2 | 0 | 168 | 4470 | 5511 | 1041 |
| 21 | 59.87 | 52.38 | 4 | 0 | 1555 | 5904 | 7445 | 1541 |
| 22 | 60 | 47.62 | 5 | 1 | 1341 | 5904 | 7445 | 1541 |
| 23 | 59.66 | 57.14 | 4 | 0 | 1141 | 5904 | 7445 | 1541 |
| 24 | 60.2 | 52.38 | 4 | 0 | 918 | 5904 | 7445 | 1541 |
| 25 | 60.37 | 47.83 | 6 | 0 | 723 | 5904 | 7445 | 1541 |
| 26 | 58.23 | 50 | 5 | 1 | 508 | 5904 | 7445 | 1541 |
| 27 | 60.35 | 50 | 4 | 0 | 281 | 5904 | 7445 | 1541 |
| 28 | 58.9 | 52.38 | 4 | 0 | 680 | 7586 | 8269 | 683 |

TABLE 1-continued

Primers for enriching mitochondrial transcripts and primer characteristics.

| | | | | | | | | |
|---|---|---|---|---|---|---|---|---|
| 29 | 59.44 | 45.45 | 3 | 1 | 450 | 7586 | 8269 | 683 |
| 30 | 59.51 | 52.38 | 4 | 2 | 218 | 7586 | 8269 | 683 |
| 31 | 57.45 | 47.62 | 3 | 2 | 225 | 8366 | 8572 | 206 |
| 32 | 60.47 | 52.38 | 3 | 0 | 686 | 8527 | 9207 | 680 |
| 33 | 59.11 | 52.38 | 4 | 1 | 461 | 8527 | 9207 | 680 |
| 34 | 60.2 | 66.67 | 6 | 0 | 235 | 8527 | 9207 | 680 |
| 35 | 60.42 | 50 | 4 | 0 | 800 | 9207 | 9990 | 783 |
| 36 | 58.89 | 55 | 2 | 0 | 694 | 9207 | 9990 | 783 |
| 37 | 60.11 | 60 | 6 | 1 | 475 | 9207 | 9990 | 783 |
| 38 | 59.72 | 52.38 | 3 | 1 | 254 | 9207 | 9990 | 783 |
| 39 | 58.81 | 52.38 | 4 | 0 | 340 | 10059 | 10404 | 345 |
| 40 | 59.36 | 52.38 | 2 | 0 | 160 | 10059 | 10404 | 345 |
| 41 | 57.45 | 37.5 | 4 | 0 | 290 | 10470 | 10766 | 296 |
| 42 | 58.94 | 37.5 | 3 | 0 | 1396 | 10760 | 12137 | 1377 |
| 43 | 60.18 | 55 | 3 | 0 | 1163 | 10760 | 12137 | 1377 |
| 44 | 59.44 | 60 | 4 | 0 | 934 | 10760 | 12137 | 1377 |
| 45 | 60.39 | 55 | 4 | 0 | 747 | 10760 | 12137 | 1377 |
| 46 | 59.66 | 47.62 | 2 | 1 | 666 | 10760 | 12137 | 1377 |
| 47 | 59.97 | 55.56 | 4 | 1 | 473 | 10760 | 12137 | 1377 |
| 48 | 59.77 | 50 | 4 | 0 | 257 | 10760 | 12137 | 1377 |
| 49 | 59.38 | 60 | 2 | 0 | 1808 | 12337 | 14148 | 1811 |
| 50 | 60.31 | 43.48 | 3 | 0 | 1567 | 12337 | 14148 | 1811 |
| 51 | 59.68 | 50 | 3 | 0 | 1337 | 12337 | 14148 | 1811 |
| 52 | 60.39 | 60 | 2 | 0 | 1099 | 12337 | 14148 | 1811 |
| 53 | 60.83 | 55 | 2 | 0 | 880 | 12337 | 14148 | 1811 |
| 54 | 59.8 | 47.62 | 4 | 0 | 653 | 12337 | 14148 | 1811 |
| 55 | 60.2 | 47.62 | 2 | 0 | 427 | 12337 | 14148 | 1811 |
| 56 | 60.25 | 50 | 2 | 0 | 242 | 12337 | 14148 | 1811 |
| 57 | 58.56 | 45.45 | 2 | 0 | 514 | 14149 | 14673 | 524 |
| 58 | 59.5 | 50 | 3 | 0 | 342 | 14149 | 14673 | 524 |
| 59 | 60.11 | 60 | 3 | 0 | 152 | 14149 | 14673 | 524 |
| 60 | 59.84 | 50 | 2 | 0 | 1156 | 14747 | 15887 | 1140 |
| 61 | 59.4 | 52.38 | 2 | 0 | 970 | 14747 | 15887 | 1140 |
| 62 | 60 | 52.38 | 3 | 0 | 819 | 14747 | 15887 | 1140 |
| 63 | 60.23 | 57.89 | 2 | 2 | 647 | 14747 | 15887 | 1140 |
| 64 | 59.86 | 57.14 | 2 | 0 | 475 | 14747 | 15887 | 1140 |
| 65 | 59.77 | 45.83 | 4 | 0 | 264 | 14747 | 15887 | 1140 |
| 66 | 59.68 | 55 | 3 | 0 | 919 | 648 | 1601 | 953 |
| 67 | 59.14 | 52.38 | 2 | 0 | 669 | 648 | 1601 | 953 |

TABLE 1-continued

Primers for enriching mitochondrial transcripts and primer characteristics.

| | | | | | | | | |
|---|---|---|---|---|---|---|---|---|
| 68 | 59.41 | 57.89 | 3 | 0 | 1264 | 1671 | 3229 | 1558 |
| 69 | 59.58 | 52.38 | 3 | 0 | 838 | 1671 | 3229 | 1558 |
| 70 | 60.16 | 50 | 4 | 0 | 647 | 3307 | 4262 | 955 |
| 71 | 59.76 | 50 | 3 | 0 | 744 | 4470 | 5511 | 1041 |
| 72 | 59.22 | 54.55 | 2 | 0 | 1249 | 5904 | 7445 | 1541 |
| 73 | 61.1 | 55 | 2 | 0 | 925 | 5904 | 7445 | 1541 |
| 74 | 59.86 | 57.14 | 4 | 0 | 437 | 7586 | 8269 | 683 |
| 75 | 59.82 | 45.45 | 2 | 0 | 432 | 8527 | 9207 | 680 |
| 76 | 59.96 | 50 | 2 | 0 | 1031 | 10760 | 12137 | 1377 |

TABLE 2

Primers for enriching mitochondrial transcripts.

| Mix | Tran-script | Distance from 3' end | Starting base | Transcript binding sequence | Primer name | Complete sequence |
|---|---|---|---|---|---|---|
| 1 | MT-ND1 | 254 | 4009 | AACACCCTCACCACTACAATCT SEQ ID NO: 15 | PvG1218_MT-ND1_4009 | CACCCGAGAATTCCAAACACCCTCACCACTACAATCT SEQ ID NO: 77 |
| 1 | MT-ND2 | 149 | 5363 | CTCCACCTCAATCACACTACTCC SEQ ID NO: 20 | PvG1223_MT-ND2_5363 | CACCCGAGAATTCCACTCCACCTCAATCACACTACTCC SEQ ID NO: 78 |
| 1 | MT-CO1 | 262 | 7184 | ACAACACTTTCTCGGCCTATCC SEQ ID NO: 27 | PvG1230_MT-CO1_7184 | CACCCGAGAATTCCAACAACACTTTCTCGGCCTATCC SEQ ID NO: 79 |
| 1 | MT-ATP8 | 206 | 8367 | TGCCCCAACTAAATACTACCG SEQ ID NO: 31 | PvG1234_MT-ATP8_8367 | CACCCGAGAATTCCATGCCCCAACTAAATACTACCG SEQ ID NO: 80 |
| 1 | MT-CO3 | 235 | 9756 | TCTCCCTTCACCATTTCCGAC SEQ ID NO: 38 | PvG1241_MT-CO3_9756 | CACCCGAGAATTCCATCTCCCTTCACCATTTCCGAC SEQ ID NO: 81 |
| 1 | MT-ND3 | 141 | 10264 | TTGCCCTCCTTTTACCCCTAC SEQ ID NO: 40 | PvG1243_MT-ND3_10264 | CACCCGAGAATTCCATTGCCCTCCTTTTACCCCTAC SEQ ID NO: 82 |
| 1 | MT-ND4L | 271 | 10496 | ACTAGCATTTACCATCTCACTTCT SEQ ID NO: 41 | PvG1244_MT-ND4L_10496 | CACCCGAGAATTCCAACTAGCATTTACCATCTCACTTCT SEQ ID NO: 83 |
| 1 | MT-ND4 | 238 | 11900 | GTGCTAGTAACCACGTTCTCCT SEQ ID NO: 48 | PvG1251_MT-ND4_11900 | CACCCGAGAATTCCAGTGCTAGTAACCACGTTCTCCT SEQ ID NO: 84 |
| 1 | MT-ND5 | 223 | 13926 | TAGCATCACACACCGCACAA SEQ ID NO: 56 | PvG1259_MT-ND5_13926 | CACCCGAGAATTCCATAGCATCACACACCGCACAA SEQ ID NO: 85 |
| 1 | MT-ND6 | 115 | 14263 | GGATCCTATTGGTGCGGGG SEQ ID NO: 86 | PvG1260_MT-ND6_14263 | CACCCGAGAATTCCAGGATCCTATTGGTGCGGGG SEQ ID NO: 87 |
| 1 | MT-CYB | 245 | 15643 | CATCCTAGCAATAATCCCCATCCT SEQ ID NO: 65 | PvG1268_MT-CYB_15643 | CACCCGAGAATTCCACATCCTAGCAATAATCCCCATCCT SEQ ID NO: 88 |
| 2 | MT-ND1 | 486 | 3777 | TGGCTCCTTTAACCTCTCCAC SEQ ID NO: 14 | PvG1217_MT-ND1_3777 | CACCCGAGAATTCCATGGCTCCTTTAACCTCTCCAC SEQ ID NO: 89 |
| 2 | MT-ND2 | 367 | 5145 | ACGACCCTACTACTATCTCGCA SEQ ID NO: 19 | PvG1222_MT-ND2_5145 | CACCCGAGAATTCCAACGACCCTACTACTATCTCGCA SEQ ID NO: 90 |
| 2 | MT-CO1 | 489 | 6957 | GGCCTGACTGGCATTGTATT SEQ ID NO: 26 | PvG1229_MT-CO1_6957 | CACCCGAGAATTCCAGGCCTGACTGGCATTGTATT SEQ ID NO: 91 |
| 2 | MT-CO2 | 418 | 7852 | GGTCAACGATCCCTCCCTTAC SEQ ID NO: 74 | PvG1232_MT-CO2_7852 | CACCCGAGAATTCCAGGTCAACGATCCCTCCCTTAC SEQ ID NO: 92 |
| 2 | MT-ATP6 | 442 | 8766 | CACAACTAACCTCCTCGGACT SEQ ID NO: 33 | PvG1236_MT-ATP6_8766 | CACCCGAGAATTCCACACAACTAACCTCCTCGGACT SEQ ID NO: 93 |

TABLE 2-continued

Primers for enriching mitochondrial transcripts.

| Mix | Tran-script | Distance from 3' end | Starting base | Transcript binding sequence | Primer name | Complete sequence |
|---|---|---|---|---|---|---|
| 2 | MT-CO3 | 456 | 9535 | CCCAATTAGGAGGGCACTGG SEQ ID NO: 37 | PvG1240_MT-CO3_9535 | CACCCGAGAATTCCACCCAATTAGG AGGGCACTGG SEQ ID NO: 94 |
| 2 | MT-ND3 | 278 | 10127 | ACTACCACAACTCAACGGCTAC SEQ ID NO: 95 | PvG1242_MT-ND3_10127 | CACCCGAGAATTCCAACTACCACAA CTCAACGGCTAC SEQ ID NO: 96 |
| 2 | MT-ND4 | 454 | 11684 | TTCACCGGCGCAGTCATT SEQ ID NO: 47 | PvG1250_MT-ND4_11684 | CACCCGAGAATTCCATTCACCGGCG CAGTCATT SEQ ID NO: 97 |
| 2 | MT-NDS | 391 | 13758 | CGCATCCCCCTTCCAAACA SEQ ID NO: 98 | PvG1258_MT-NDS_13758 | CACCCGAGAATTCCACGCATCCCCCT TCCAAACA SEQ ID NO: 99 |
| 2 | MT-ND6 | 344 | 14492 | GGGGAATGATGGTTGTCTTTGG SEQ ID NO: 58 | PvG1261_MT-ND6_14492 | CACCCGAGAATTCCAGGGGAATGAT GGTTGTCTTTGG SEQ ID NO: 100 |
| 2 | MT-CYB | 456 | 15432 | CCCTCGGCTTACTTCTCTTCC SEQ ID NO: 64 | PvG1267_MT-CYB_15432 | CACCCGAGAATTCCACCCTCGGCTTA CTTCTCTTCC SEQ ID NO: 101 |
| 3 | MT-ND1 | 726 | 3537 | AGCTCTCACCATCGCTCTTC SEQ ID NO: 13 | PvG1216_MT-ND1_3537 | CACCCGAGAATTCCAAGCTCTCACCA TCGCTCTTC SEQ ID NO: 102 |
| 3 | MT-ND2 | 589 | 4923 | AGCCTTCTCCTCACTCTCTCAA SEQ ID NO: 18 | PvG1221_MT-ND2_4923 | CACCCGAGAATTCCAAGCCTTCTCCT CACTCTCTCAA SEQ ID NO: 103 |
| 3 | MT-CO1 | 704 | 6742 | TTGGCTTCCTAGGGTTTATCGTG SEQ ID NO: 25 | PvG1228_MT-CO1_6742 | CACCCGAGAATTCCATTGGCTTCCTA GGGTTTATCGTG SEQ ID NO: 104 |
| 3 | MT-CO2 | 661 | 7609 | TCTACAAGACGCTACTTCCCC SEQ ID NO: 28 | PvG1231_MT-CO2_7609 | CACCCGAGAATTCCATCTACAAGAC GCTACTTCCCC SEQ ID NO: 105 |
| 3 | MT-ATP6 | 667 | 8541 | GTTCGCTTCATTCATTGCCCC SEQ ID NO: 32 | PvG1235_MT-ATP6_8541 | CACCCGAGAATTCCAGTTCGCTTCAT TCATTGCCCC SEQ ID NO: 106 |
| 3 | MT-CO3 | 675 | 9316 | TCCACTCCATAACGCTCCTC SEQ ID NO: 36 | PvG1239_MT-CO3_9316 | CACCCGAGAATTCCATCCACTCCATA ACGCTCCTC SEQ ID NO: 107 |
| 3 | MT-ND4 | 647 | 11491 | ACGCCTCACACTCATTCTCAA SEQ ID NO: 46 | PvG1249_MT-ND4_11491 | CACCCGAGAATTCCAACGCCTCACA CTCATTCTCAA SEQ ID NO: 108 |
| 3 | MT-NDS | 634 | 13515 | CCACATCATCGAAACCGCAAA SEQ ID NO: 54 | PvG1257_MT-NDS_13515 | CACCCGAGAATTCCACCACATCATCG AAACCGCAAA SEQ ID NO: 109 |
| 3 | MT-ND6 | 516 | 14664 | GCTTTGTTTCTGTTGAGTGTGG SEQ ID NO: 57 | PvG1262_MT-ND6_14664 | CACCCGAGAATTCCAGCTTTGTTTCT GTTGAGTGTGG SEQ ID NO: 110 |
| 3 | MT-CYB | 628 | 15260 | AGTCCCACCCTCACACGAT SEQ ID NO: 63 | PvG1266_MT-CYB_15260 | CACCCGAGAATTCCAAGTCCCACCCT CACACGAT SEQ ID NO: 111 |
| 4 | MT-RNR1 | 946 | 656 | TGGTCCTAGCCTTTCTATTAGCT C SEQ ID NO: 1 | PvG1204_MT-RNR1_656 | CACCCGAGAATTCCATGGTCCTAGC CTTTCTATTAGCTC SEQ ID NO: 112 |
| 4 | MT-ND1 | 865 | 3398 | TACAACTACGCAAAGGCCCC SEQ ID NO: 113 | PvG1215_MT-ND1_3398 | CACCCGAGAATTCCATACAACTACG CAAAGGCCCC SEQ ID NO: 114 |
| 4 | MT-ND2 | 801 | 4711 | CCGGACAATGAACCATAACCAA SEQ ID NO: 17 | PvG1220_MT-ND2_4711 | CACCCGAGAATTCCACCGGACAATG AACCATAACCAA SEQ ID NO: 115 |
| 4 | MT-CO1 | 899 | 6547 | TCAACACCACCTTCTTCGACC SEQ ID NO: 24 | PvG1227_MT-CO1_6547 | CACCCGAGAATTCCATCAACACCACC TTCTTCGACC SEQ ID NO: 116 |
| 4 | MT-CO3 | 781 | 9210 | ACCCACCAATCACATGCCTATC SEQ ID NO: 35 | PvG1238_MT-CO3_9210 | CACCCGAGAATTCCAACCCACCAATC ACATGCCTATC SEQ ID NO: 117 |
| 4 | MT-ND4 | 728 | 11410 | TAAAGCCCATGTCGAAGCCC SEQ ID NO: 45 | PvG1248_MT-ND4_11410 | CACCCGAGAATTCCATAAAGCCCAT GTCGAAGCCC SEQ ID NO: 118 |
| 4 | MT-ND5 | 861 | 13288 | GGCATCAACCAACCACACCT SEQ ID NO: 53 | PvG1256_MT-ND5_13288 | CACCCGAGAATTCCAGGCATCAACC AACCACACCT SEQ ID NO: 119 |
| 4 | MT-CYB | 800 | 15088 | CATCGGCATTATCCTCCTGCT SEQ ID NO: 62 | PvG1265_MT-CYB_15088 | CACCCGAGAATTCCACATCGGCATT ATCCTCCTGCT SEQ ID NO: 120 |
| 5 | MT-ND2 | 1029 | 4483 | CCCAACCCGTCATCTACTCTAC SEQ ID NO: 16 | PvG1219_MT-ND2_4483 | CACCCGAGAATTCCACCCAACCCGTC ATCTACTCTAC SEQ ID NO: 121 |

TABLE 2-continued

Primers for enriching mitochondrial transcripts.

| Mix | Transcript | Distance from 3' end | Starting base | Transcript binding sequence | Primer name | Complete sequence |
|---|---|---|---|---|---|---|
| 5 | MT-CO1 | 1122 | 6324 | GCCTCCGTAGACCTAACCATC SEQ ID NO: 23 | PvG1226_MT-CO1_6324 | CACCCGAGAATTCCAGCCTCCGTAGACCTAACCATC SEQ ID NO: 122 |
| 5 | MT-ND4 | 915 | 11223 | TAGGCTCCCTTCCCCTACTC SEQ ID NO: 44 | PvG1247_MT-ND4_11223 | CACCCGAGAATTCCATAGGCTCCCTTCCCCTACTC SEQ ID NO: 123 |
| 5 | MT-NDS | 1080 | 13069 | GCCCTACTCCACTCAAGCAC SEQ ID NO: 52 | PvG1255_MT-NDS_13069 | CACCCGAGAATTCCAGCCCTACTCCACTCAAGCAC SEQ ID NO: 124 |
| 5 | MT-CYB | 951 | 14937 | CATCAATCGCCCACATCACTC SEQ ID NO: 61 | PvG1264_MT-CYB_14937 | CACCCGAGAATTCCACATCAATCGCCCACATCACTC SEQ ID NO: 125 |
| 6 | MT-RNR2 | 706 | 2524 | ACCAGTATTAGAGGCACCGC SEQ ID NO: 9 | PvG1212_MT-RNR2_2524 | CACCCGAGAATTCCAACCAGTATTAGAGGCACCGC SEQ ID NO: 126 |
| 6 | MT-CO1 | 1322 | 6124 | TAATCGGAGGCTTTGGCAACT SEQ ID NO: 22 | PvG1225_MT-CO1_6124 | CACCCGAGAATTCCATAATCGGAGGCTTTGGCAACT SEQ ID NO: 127 |
| 6 | MT-ND4 | 1144 | 10994 | GCAAGCCAACGCCACTTATC SEQ ID NO: 43 | PvG1246_MT-ND4_10994 | CACCCGAGAATTCCAGCAAGCCAACGCCACTTATC SEQ ID NO: 128 |
| 6 | MT-NDS | 1318 | 12831 | CACAGCAGCCATTCAAGCAA SEQ ID NO: 51 | PvG1254_MT-NDS_12831 | CACCCGAGAATTCCACACAGCAGCCATTCAAGCAA SEQ ID NO: 129 |
| 6 | MT-CYB | 1099 | 14789 | AACCACTCATTCATCGACCTCC SEQ ID NO: 130 | PvG1263_MT-CYB_14789 | CACCCGAGAATTCCAAACCACTCATTCATCGACCTCC SEQ ID NO: 131 |
| 7 | MT-RNR2 | 1120 | 2110 | ACAGCTCTTTGGACACTAGGAA SEQ ID NO: 7 | PvG1210_MT-RNR2_2110 | CACCCGAGAATTCCAACAGCTCTTTGGACACTAGGAA SEQ ID NO: 132 |
| 7 | MT-CO1 | 1536 | 5910 | GCCGACCGTTGACTATTCTCT SEQ ID NO: 21 | PvG1224_MT-CO1_5910 | CACCCGAGAATTCCAGCCGACCGTTGACTATTCTCT SEQ ID NO: 133 |
| 7 | MT-ND4 | 1377 | 10761 | TGCTAAAACTAATCGTCCCAACAA SEQ ID NO: 42 | PvG1245_MT-ND4_10761 | CACCCGAGAATTCCATGCTAAAACTAATCGTCCCAACAA SEQ ID NO: 134 |
| 7 | MT-NDS | 1548 | 12601 | TTCATCCCTGTAGCATTGTTCGT SEQ ID NO: 50 | PvG1253_MT-NDS_12601 | CACCCGAGAATTCCATTCATCCCTGTAGCATTGTTCGT SEQ ID NO: 135 |
| 8 | MT-RNR2 | 1551 | 1679 | TAGCCCCAAACCCACTCCAC SEQ ID NO: 5 | PvG1208_MT-RNR2_1679 | CACCCGAGAATTCCATAGCCCCAAACCCACTCCAC SEQ ID NO: 136 |
| 8 | MT-NDS | 1789 | 12360 | CACCCTAACCCTGACTTCCC SEQ ID NO: 49 | PvG1252_MT-NDS_12360 | CACCCGAGAATTCCACACCCTAACCCTGACTTCCC SEQ ID NO: 137 |
| R1 | MT-RNR1 | 255 | 1347 | GGTGGCAAGAAATGGGCTACA SEQ ID NO: 4 | PvG1207_MT-RNR1_1347 | CACCCGAGAATTCCAGGTGGCAAGAAATGGGCTACA SEQ ID NO: 138 |
| R1 | MT-RNR2 | 245 | 2985 | CCTCGATGTTGGATCAGGAC SEQ ID NO: 11 | PvG1214_MT-RNR2_2985 | CACCCGAGAATTCCACCTCGATGTTGGATCAGGAC SEQ ID NO: 139 |
| R1 | MT-ATP6 | 216 | 8992 | CTGGCCGTACGCCTAACC SEQ ID NO: 34 | PvG1237_MT-ATP6_8992 | CACCCGAGAATTCCACTGGCCGTACGCCTAACC SEQ ID NO: 140 |
| R2 | MT-RNR1 | 475 | 1127 | ACTGCTCGCCAGAACACTAC SEQ ID NO: 3 | PvG1206_MT-RNR1_1127 | CACCCGAGAATTCCAACTGCTCGCCAGAACACTAC SEQ ID NO: 141 |
| R2 | MT-RNR2 | 473 | 2757 | AGTACCTAACAAACCCACAGGTC SEQ ID NO: 10 | PvG1213_MT-RNR2_2757 | CACCCGAGAATTCCAAGTACCTAACAAACCCACAGGTC SEQ ID NO: 142 |
| R3 | MT-RNR1 | 703 | 899 | GCGGTCACACGATTAACCCA SEQ ID NO: 2 | PvG1205_MT-RNR1_899 | CACCCGAGAATTCCAGCGGTCACACGATTAACCCA SEQ ID NO: 143 |
| R3 | MT-RNR2 | 907 | 2323 | ATTCTCCTCCGCATAAGCCTG SEQ ID NO: 8 | PvG1211_MT-RNR2_2323 | CACCCGAGAATTCCAATTCTCCTCCGCATAAGCCTG SEQ ID NO: 144 |
| R4 | MT-RNR2 | 1335 | 1895 | CTAAGACCCCCGAAACCAGA SEQ ID NO: 6 | PvG1209_MT-RNR2_1895 | CACCCGAGAATTCCACTAAGACCCCCGAAACCAGA SEQ ID NO: 145 |
| R4 | MT-CO2 | 199 | 8071 | ATGAGCTGTCCCCACATTAGG SEQ ID NO: 30 | PvG1233_MT-CO2_8071 | CACCCGAGAATTCCAATGAGCTGTCCCCACATTAGG SEQ ID NO: 146 |

In certain embodiments, PCR may be used to enrich for target sites close to the poly A sequence (i.e., close to the UMI and cell barcode). In certain embodiments, the site is less than 1 kb from the cell barcode. In certain embodiments, PCR may be used to enrich for target sites greater than 1 kb away from the cell barcode. In certain embodiments, long read sequencing can be used to identify the barcode, UMI and target sites (e.g., nanopore sequencing).

In certain embodiments, the primers may include a binding moiety that can be captured using a bead or solid support. The binding moiety may be a biotin molecule that can captured using a streptavidin bead or solid support. In certain embodiments, enrichment may be by PCR using a biotin labeled primer (see, e.g., FIG. 16A; and WO 2019/084055 FIG. 19A). Thus, the method also provides for biotin enrichment of the first PCR product. Biotinylation of the primer to amplify the gene, region or mutation of interest from the library allows for the purification of the PCR product of interest. In certain embodiments, the libraries are flanked with SMART sequences on both ends, such that the vast majority of the first PCR product would be amplification of the entire library. In some embodiments, without the biotinylated primer, enrichment of the gene, region or mutation of interest would be insufficient to efficiently and confidently call genetic mutations. Biotin enrichment may be accomplished by streptavidin binding of the biotinylated first PCR product. The streptavidin bead kilobaseBINDER kit (Thermo Fisher Cat #60101) allows for isolation of large biotinylated DNA fragments. However, as described herein, other embodiments of the methods disclosed herein do not require an enrichment step and may advantageously be used without biotinylated primers.

In certain embodiments, circularization-PCR is used to enrich for target sites anywhere in the transcript (see, e.g., International Patent Publication No. WO 2019/084055 FIG. 1). Circularization-PCR works particularly well for libraries where a subset of the transcripts of interest are more than 1 kb away from the cell barcode. The primers may also include a binding moiety as described herein.

In some embodiments, the primers for amplifying in a first PCR amplification comprise USER sequences, and the method further comprises treating the first PCR product with USER enzyme, thereby generating a circularized product.

The steps include cleaving the dU residue by addition of a uracil-specific excision reagent ("USER®") enzyme/T4 ligase to generate long complementary sticky ends to mediate efficient circularization and ligation, which now places the barcode and the 5' edge of the transcript sequence set in the primer extension in close proximity, thereby bringing the cell barcode within 100 bases of any desired sequence in the transcript.

Following treating with USER enzyme, the step of amplifying the circularized product in a second polymerase chain reaction with one or more primers, wherein the one or primers comprise a library barcode and/or additional sequencing adapters can be conducted.

In some embodiments, the method can then include more than one PCR steps with transcript specific primers, that can include adaptor sequences, and preferably uses nested PCR reactions where the final PCR reaction sets the 3' edge of the transcript sequence of the final sequencing construct. The final sequencing library can be utilized in several ways, including sequencing of the transcript sequence, or at some desired location in the transcript sequence.

In one embodiment, the methods disclosed herein provide a protocol that eliminates need for enrichment in a scalable process. An exemplary embodiment can provide for amplification of all variable regions of a T-cell receptor. The methods described herein can advantageously be used for the amplification of regions not well characterized in RNA-seq libraries. The steps include providing an RNA-seq library, in some preferred embodiments, a Seq-Well library. The starting library comprises a plurality of nucleic acids with each nucleic acid comprising a gene, a unique molecular identifier (UMI) and a cell barcode (cell BC) flanked by universal sequences.

In an embodiment, the method comprises conducting primer extension on a nucleic acid in the library with one or more 5' primers with each primer comprising a sequence complementary to a desired transcript and the universal sequence of the nucleic acid, thereby replicating one or more desired transcripts and setting a 5' edge of one or more desired transcript sequences in one or more final sequencing constructs; amplifying the replicated one or more desired transcript sequences with universal primers having complementary sequences on 5' ends of the universal primers followed by a deoxy-uracil residue to form an amplicon; and ligating the amplicons by reacting the amplicons with a uracil-specific excision reagent enzyme, thereby cleaving the amplicon at the deoxy-uracil residues resulting in sticky ends that mediate circularization.

Additional steps of amplifying by PCR may be performed. In these instances, primers complementary to a transcript of interest. In some preferred embodiments, at least two PCR steps are performed in a nested PCR using two sets of transcript specific primers complementary to a transcript of interest. As described previously, the primers may comprise adaptor sequences. In one embodiment, at least one set of the two sets of transcript specific primers comprise adaptor sequences, thereby yielding a final sequencing library of final sequencing constructs. In an embodiment, the last PCR step sets a 3' edge of the transcript sequence of the final construct. In some embodiments, the sequencing step utilizes primers complementary to the 3' set and 5' set edges of the final sequencing construct. The sequencing step can utilize a primer binding to a desired location in the final sequencing construct to drive a sequencing read at the desired location in the final sequencing construct, as described elsewhere herein.

In an embodiment, the present invention provides a library of enriched single cell RNA transcripts comprising a plurality of nucleic acids comprising a cell barcode in close proximity to a desired transcript sequence of interest, the plurality of nucleic acids derived from a 3'barcoded single cell RNA library, wherein at least a subset of the plurality of nucleic acids in the library comprise transcripts of interest that are greater than 1 kb away from the cell barcode in the 3' barcoded single cell RNA library.

In some embodiments, the subset comprises transcript of interest wherein at least 1%, at least 5%, at least 10%, at least 20%, at least 25%, at least 30%, at least 35%, at least 40%, at least 45%, at least 50%, at least 55%, at least 60%, at least 65%, at least 70%, at least at least 80%, at least 90%, substantially all, or all of the transcripts in the 3' barcoded single cell RNA library are greater than 1 kb away from the cell barcode.

In one aspect, a new library of desired transcripts is provided, particularly from the 5' side of transcripts, or portions of transcript distant from the 3' cell barcode of 3' barcoded single cell libraries such as, for example, a Seq-Well library. The generated library contains desired transcripts, often enriched from low copy single cell sequencing, or from portions of a transcript that may be difficult to obtain in typical single-cell sequencing methods, while maintaining single cell identity. In some embodiments, the library contains transcripts that are distant from the 3' cell barcode, in some instances the library contains transcripts greater than about 1 kb away from the 3' end of the transcript. The enriched libraries can be comprised of enrichment of transcripts containing gene mutations located anywhere in the genome.

In certain embodiments, transcripts are enriched from a cDNA library by hybridizing a probe specific to target transcripts and isolating the hybridized transcripts. In exemplary embodiments, enrichment is performed by solution phase capture (Gnirke A, et al. 2009; and US Patent Publication No. 20100029498) or microarray capture (e.g. modified NimbleGen platform). The probes may include binding moieties, such as biotin. Methods for isolating target single stranded DNA with biotinylated RNA probes are also known in the art (e.g., SureSelect Target Enrichment, Agilent Technologies). In certain embodiments, biotinylated RNA probes may be used to enrich cDNA molecules.

Selecting Mutations

In certain embodiments, the most informative mitochondrial mutations are selected. Orthogonal detection of informative variants from the mitochondrial genome is advantageous for the present invention. Because each cell has hundreds of mitochondrial genomes, mitochondrial mutations can be at a low frequency in a single cell (unlike nuclear genomic DNA mutations). High frequency mutations are easier to detect in the single-cell data and are the most informative. The most informative mutations are also different between clones of interest.

In certain embodiments, somatic mutations occur over time in long lived organisms. In certain embodiments, somatic mutations occur and are propagated over years. Thus, in preferred embodiments, the subjects according to the present invention include higher eukaryotes (e.g., mammals, humans, livestock, cats, dogs, rodents).

As used herein, the term "homoplasmic" refers to a eukaryotic cell whose copies of mitochondrial DNA are all identical or alleles that are identical in all mitochondria. As used herein, the term "homoplasmic" also refers to identical sequencing reads for a specific genomic region.

In certain embodiments, heteroplasmic mitochondrial mutations are selected and used to cluster single cells. As used herein, the term "heteroplasmic" refers to the presence of more than one type of organellar genome (mitochondrial DNA or plastid DNA) within a cell or individual or mutations only occurring in some copies of mitochondrial DNA. Because most eukaryotic cells contain many hundreds of mitochondria with hundreds of copies of mitochondrial DNA, it is common for mutations to affect only some mitochondria, leaving most unaffected. For example, 5% heteroplasmy refers to a mutation being present in 5% of all mitochondrial genomes. As used herein, "heteroplasmic" also refers to the percentage of mutations in terms of number of reads spanning a specific genomic region. For example, if there are 100 sequencing reads across a region, 5% means that this mutation is in 5 out of 100 reads.

In certain embodiments, mitochondrial mutations used for clustering are selected. In certain embodiments, mutations having a certain heteroplasmy are selected. In certain embodiments, heteroplasmy above a threshold is used because these mutations have a higher probability of being passed onto progeny during multiple generations. In certain embodiments, the mutations are 0.1, 0.25, 0.5, 1, 2, 3, 4, 5, 10, 20 or 25% heteroplasmic.

In certain embodiments, mutations are selected in terms of number of reads spanning a specific genomic region. In certain embodiments, mutations are observed in more than 5 reads. For example, if there is only 1 read with the mutation out of 20 reads spanning this region, this mutation may be eliminated as a low confidence mutation. The low confidence mutations may not be "real". Therefore, in certain embodiments, mutations are selected based on the heteroplasmy in sequencing reads and the number of reads is above a minimum threshold greater than 1 sequencing read having a mutation.

In certain embodiments, heteroplasmy is determined in terms of sequencing reads in all of the single cells analyzed. In certain embodiments, mutations are selected that have greater than 0.5% heteroplasmy. In certain embodiments, mutations are selected based on a conservative threshold and have greater than 5% heteroplasmy.

In certain embodiments, mutations are selected based on mutations detected in mitochondrial genome sequencing reads of a bulk sample obtained from the subject. The bulk sample may be sequenced according to any of the methods for sequencing the mitochondrial genome described above (e.g., DNA-seq, RNA-seq, ATAC-seq or RCA-seq). In certain embodiments, the mitochondrial genome is sequenced directly to determine somatic mutations and not mutations detected due to RNA modifications or reverse transcription errors. In certain embodiments, mutations are selected independently based on detection in the bulk samples and are not further selected based on heteroplasmy. In certain embodiments, the mutations are further selected based on heteroplasmy and mutations are selected from the bulk sample that are greater than 0.5% heteroplasmy. In certain embodiments, the mutations detected in the bulk sample are observed in greater than 1 sequencing read. Applicants can also use ATAC-seq or another set of primers to detect mitochondrial mutations from bulk DNA (not cDNA) of the same sample.

In certain embodiments, mutations are selected based on a base quality score. In certain embodiments, the detected mutations have a Phred quality score greater than 20. A Phred quality score is a measure of the quality of the identification of the nucleobases generated by automated DNA sequencing (see, e.g., Ewing et al., (1998). "Base-calling of automated sequencer traces using phred. I. Accuracy assessment". *Genome Research.* 8 (3): 175-185; and Ewing and Green (1998). "Base-calling of automated sequencer traces using phred. II. Error probabilities". *Genome Research.* 8 (3): 186-194). It was originally developed for Phred base calling to help in the automation of DNA sequencing in the Human Genome Project. Phred quality scores are assigned to each nucleotide base call in automated sequencer traces. Phred quality scores have become widely accepted to characterize the quality of DNA sequences, and can be used to compare the efficacy of different sequencing methods. Perhaps the most important use of Phred quality scores is the automatic determination of accurate, quality-based consensus sequences.

The method may further comprise excluding RNA modifications, RNA transcription errors and/or RNA sequencing errors from the mutations detected. The RNA modifications may comprise previously identified RNA modifications. These include RNA modifications known in the art and modifications identified by sequencing mitochondrial genomes and comparing the sequences to mitochondrial transcripts. In certain embodiments, RNA modifications, RNA transcription errors and/or RNA sequencing errors are determined by comparing the mutations detected by scRNA-seq to mutations detected by DNA-seq, ATAC-seq or RCA-seq in a bulk sample from the subject.

Determining a Lineage or Clonal Structure

In certain embodiments, a lineage or clonal structure is determined. As used herein the terms “lineage” or “clonal structure” refer to the relationship between any two or more cells. As used herein, the term “cell lineage” refers to the developmental path by which a fertilized egg gives rise to the cells of a multicellular organism or the developmental history of a tissue or organ.

As used herein the terms “lineage map” refer to a diagram showing a cell lineage.

As used herein, the term “clone” is a group of cells that share a common ancestry, meaning they are derived from the same cell. In certain embodiments, new mutations arise over time in a clonal population giving rise to sub-clonal populations of cells. As used herein, the term “clonal structure” allows to assess clonal contributions of clones and subclones, for example in a tumor. In certain embodiments, the clonal structure is determined before and after a treatment.

In certain embodiments, such as in multicellular organisms, the progeny of single dividing cells cannot be followed and a cell lineage or clonal structure is inferred retrospectively (e.g., after cell division has already occurred). The present invention provides for improved methods of inferring a cell lineage or clonal structure by detecting somatic mutations, specifically somatic mutations that occur in the mitochondrial genome.

Determination of somatic mutations (e.g., including mitochondrial mutations) allows cells derived from a tissue or tumor to be clustered based on the mutations. In certain embodiments, the method further comprises detecting mutations in the nuclear genome and clustering the cells based on the presence of the mitochondrial and nuclear genome mutations in the single cells. In certain embodiments, the method comprises sequencing the nuclear genome in single cells obtained from the subject according to a sequencing method described herein (e.g., whole genome, whole exome sequencing). The clustering provides for related cells.

As used herein, the term “clustering” or “cluster analysis” refers to the task of grouping a set of objects (e.g., cells) in such a way that objects in the same group (called a cluster) are more similar (in some sense) to each other than to those in other groups (clusters). It is a main task of exploratory data mining, and a common technique for statistical data analysis, used in many fields, including machine learning, pattern recognition, image analysis, information retrieval, bioinformatics, data compression, and computer graphics.

Cluster analysis itself is not one specific algorithm, but the general task to be solved. It can be achieved by various algorithms that differ significantly in their understanding of what constitutes a cluster and how to efficiently find them. Popular notions of clusters include groups with small distances between cluster members, dense areas of the data space, intervals or particular statistical distributions. Clustering can therefore be formulated as a multi-objective optimization problem. The appropriate clustering algorithm and parameter settings (including parameters such as the distance function to use, a density threshold or the number of expected clusters) depend on the individual data set and intended use of the results. Cluster analysis as such is not an automatic task, but an iterative process of knowledge discovery or interactive multi-objective optimization that involves trial and failure. It is often necessary to modify data preprocessing and model parameters until the result achieves the desired properties. In certain embodiments, clustering is performed based on somatic mutations present in single cells. In certain embodiments, clustering is performed based on the transcriptomes of single cells.

Clustering can employ different algorithms to generate cluster models. Typical cluster models include:

Connectivity models, for example, hierarchical clustering builds models based on distance connectivity.

Centroid models: for example, the k-means algorithm represents each cluster by a single mean vector.

Distribution models: clusters are modeled using statistical distributions, such as multivariate normal distributions used by the expectation-maximization algorithm.

Density models: for example, DBSCAN and OPTICS defines clusters as connected dense regions in the data space.

Subspace models: in biclustering (also known as co-clustering or two-mode-clustering), clusters are modeled with both cluster members and relevant attributes.

Group models: some algorithms do not provide a refined model for their results and just provide the grouping information.

Graph-based models: a clique, that is, a subset of nodes in a graph such that every two nodes in the subset are connected by an edge can be considered as a prototypical form of cluster. Relaxations of the complete connectivity requirement (a fraction of the edges can be missing) are known as quasi-cliques, as in the HCS clustering algorithm.

Neural models: the most well-known unsupervised neural network is the self-organizing map and these models can usually be characterized as similar to one or more of the above models, and including subspace models when neural networks implement a form of Principal Component Analysis or Independent Component Analysis.

A “clustering” is essentially a set of such clusters, usually containing all objects in the data set. Additionally, it may specify the relationship of the clusters to each other, for example, a hierarchy of clusters embedded in each other. Clusterings can be roughly distinguished as: Hard clustering: each object belongs to a cluster or not.

Soft clustering (also: fuzzy clustering): each object belongs to each cluster to a certain degree (for example, a likelihood of belonging to the cluster).

There are also finer distinctions possible, for example:

Strict partitioning clustering: each object belongs to exactly one cluster.

Strict partitioning clustering with outliers: objects can also belong to no cluster, and are considered outliers.

Overlapping clustering (also: alternative clustering, multi-view clustering): objects may belong to more than one cluster; usually involving hard clusters.

Hierarchical clustering: objects that belong to a child cluster also belong to the parent cluster.

Subspace clustering: while an overlapping clustering, within a uniquely defined subspace, clusters are not expected to overlap.

In certain embodiments, single cells are clustered by hierarchical clustering using somatic mutations.

Cell States

In certain embodiments, the cell states of the clusters are determined. Thus, cell states can be mapped to specific lineage or clonal structures. As used herein, the term “cell state” includes, but is not limited to the gene expression, epigenetic configuration, and/or nuclear structure of single cells. The cell state may be a differentially expressed gene, differentially expressed gene signature, or a differentially accessible chromatin loci.

In certain embodiments, the cell state is determined by analyzing the sequencing data generated for determining somatic mutations (e.g., scRNA-seq, scATAC-seq). Single cell RNA sequencing allows for detecting mitochondrial genome mutations in the transcribed mitochondrial RNA.

Mitochondrial RNA is polyadenylated and can be captured by methods that use poly T to reverse transcribe and/or capture mRNA. Single cell ATAC-seq a high-throughput sequencing technique that identifies open chromatin. Depending on the cell type, ATAC-seq samples may contain ~20-80% of mitochondrial sequencing reads and is normally removed as it increases the cost of sequencing. In certain embodiments, single cells are analyzed in separate reaction vessels to preserve the ability to analyze the single cells. Analysis may include proteomic and genomic analysis on the single cells.

In certain embodiments, heritable cell states are identified. Heritable cell states may be cell states that are passed down through a lineage (e.g., specific gene signatures shared by cells in a lineage). In certain embodiments, the establishment of a cell state along a lineage is identified (e.g., when a cell state is established).

Use of Signature Genes

In certain embodiments, gene signatures are identified that are shared by cells in a lineage. As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub) populations. Increased or decreased expression or activity or prevalence of signature genes may be compared between different cells in order to characterize or identify for instance specific cell (sub) populations. The detection of a signature in single cells may be used to identify and quantitate for instance specific cell (sub) populations. A signature may include a gene or genes, protein or proteins, or epigenetic element(s) whose expression or occurrence is specific to a cell (sub) population, such that expression or occurrence is exclusive to the cell (sub) population. A gene signature as used herein, may thus refer to any set of up- and down-regulated genes that are representative of a cell type or subtype. A gene signature as used herein, may also refer to any set of up- and down-regulated genes between different cells or cell (sub) populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub) population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub) types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular tumor cell or tumor cell (sub) population if it is upregulated or only present, detected or detectable in that particular tumor cell or tumor cell (sub) population, or alternatively is downregulated or only absent, or undetectable in that particular tumor cell or tumor cell (sub) population. In this context, a signature consists of one or more differentially expressed genes/proteins or differential epigenetic elements when comparing different cells or cell (sub) populations, including comparing different tumor cells or tumor cell (sub) populations, as well as comparing tumor cells or tumor cell (sub) populations with non-tumor cells or non-tumor cell (sub) populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of tumor cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized and is preferably characterized by the signature as discussed herein. A cell (sub) population as referred to herein may constitute of a (sub) population of cells of a particular cell type characterized by a specific cell state.

When referring to induction, or alternatively suppression of a particular signature, preferably, induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature is meant.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein, as well as methods to obtain such cell (sub) populations and screening methods to identify agents capable of inducing or suppressing particular tumor cell (sub) populations.

The invention further relates to various uses of the gene signatures, protein signature, and/or other genetic or epigenetic signature as defined herein, as well as various uses of the tumor cells or tumor cell (sub) populations as defined herein. Particular advantageous uses include methods for identifying agents capable of inducing or suppressing particular tumor cell (sub) populations based on the gene signatures, protein signature, and/or other genetic or epigenetic signature as defined herein. The invention further relates to agents capable of inducing or suppressing particular tumor cell (sub) populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall tumor composition, such as tumor cell composition, such as tumor cell subpopulation composition or distribution, or functionality.

The signature genes of the present invention may be discovered by analysis of expression profiles of single-cells within a population of cells from freshly isolated tumors, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient tumor. Not being bound by a theory, a tumor is a conglomeration of many cells that make up a tumor microenvironment, whereby the cells communicate and affect each other in specific ways. As such, specific cell types within this microenvironment may express signature genes specific for this microenvironment. Not being bound by a theory, the signature genes of the present invention may be microenvironment specific, such as their expression in a tumor. Not being bound by a theory, signature genes determined in single cells that originated in a tumor are specific to other tumors. Not being bound by a theory, a combination of cell subtypes in a tumor may indicate an outcome. Not being bound by a theory, the signature genes can be used to deconvolute the network of cells present in a tumor based on comparing them to data from bulk analysis of a tumor sample. Not being bound by a theory, the presence of specific cells and cell subtypes may be indicative of tumor growth, invasiveness and resistance to treatment. The signature gene may indicate the presence of one particular cell type. In one embodiment, the signature genes may indicate that tumor infiltrating T-cells are present. The presence of cell types within a tumor may indicate that the tumor will be resistant to a treatment. In one embodiment, the signature genes of the present invention are applied to bulk sequencing data from a tumor sample obtained from a subject, such that information relating to disease outcome and personalized treatments is determined. In one embodiment, the novel signature genes are used to detect multiple cell states that occur in a subpopulation of tumor cells that are linked to resistance to targeted therapies and progressive tumor growth.

In one embodiment, the signature genes are detected by immunofluorescence, immunohistochemistry, fluorescence activated cell sorting (FACS), mass cytometry (CyTOF), Drop-seq, RNA-seq, scRNA-seq, InDrop, single cell qPCR, MERFISH (multiplex (in situ) RNA FISH) and/or by in situ hybridization (e.g., FISH). Other methods including absorbance assays and colorimetric assays are known in the art and may be used herein.

In one embodiment, tumor cells are stained for sub-clonal cell type specific signature genes. In one embodiment, the cells are fixed. In another embodiment, the cells are formalin fixed and paraffin embedded. Not being bound by a theory, the presence of the cell subtypes in a tumor indicate outcome and personalized treatments. Not being bound by a theory, the cell subtypes may be quantitated in a section of a tumor and the number of cells indicates an outcome and personalized treatment.

Lineages and Clonal Populations in Tissues

In certain embodiments, the single cells comprise related cell types. The related cell types may be from a tissue. In certain embodiments, lineage or clonal structures are determined for specific tissues. The tissue may be associated with a disease state. The disease may be a degenerative disease. The tissue may be healthy tissue. Thus, healthy tissue may be studied to understand a disease state. The tissue may be diseased tissue. Thus, diseased tissue may be studied to understand a disease state.

The present invention provides for a method of identifying changes in clonal populations having a cell state between healthy and diseased tissue comprising determining clonal populations of cells having a cell state in healthy and diseased cells and comparing the clonal populations. Thus, clonal populations are determined in healthy and diseased tissues. The cell states in the clonal populations can be determined. The tissues may be obtained from the same subject. The cell states are then determined for the clonal populations. Clonal populations shared between the diseased and healthy tissues, as well as clonal populations differentially present or absent between the diseased and healthy tissues can be determined. The present invention allows for improved determination of clonal populations and thus can provide for novel therapeutic targets present in specific populations.

The disease may be selected from the group consisting of autoimmune disease, bone marrow failure, hematological conditions, aplastic anemia, beta-thalassemia, diabetes, motor neuron disease, Parkinson's disease, spinal cord injury, muscular dystrophy, kidney disease, liver disease, multiple sclerosis, congestive heart failure, head trauma, lung disease, psoriasis, liver cirrhosis, vision loss, cystic fibrosis, hepatitis C virus, human immunodeficiency virus, inflammatory bowel disease (IBD), and any disorder associated with tissue degeneration.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barré syndrome (GBS); Hashimoto's disease; idiopathic thrombocytopenia purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

In certain embodiments, tissue specific mitochondrial mutations are determined for a subject. The tissue specific mitochondrial mutations may be used to better characterize tissues in healthy tissues and diseased tissue. In certain embodiments, tissue specific mutations may be used to determine the cell origin of metastatic cancer of unknown primary origin.

Clonal Populations in Tumors

In another aspect, the present invention provides for a method of detecting clonal populations of cells in a tumor sample obtained from a subject in need thereof. In certain embodiments, clonal populations of cells are identified based on the presence of the mitochondrial mutations and somatic mutations associated with the cancer in the single cells.

Somatic mutations associated with cancer may include mutations associated with prognosis, treatment or resistance to treatment. Mutations associated across the spectrum of human cancer types have been identified (e.g., Hodis E. et al., Cell. (2012) July 20; 150 (2): 251-63; and Vogelstein, et al., Science (2013) Mar. 29: Vol. 339, Issue 6127, pp. 1546-1558). A directory of cancer mutations, including gene specific mutations may be found at cancer.sanger.ac.uk/cosmic, the Catalogue of Somatic Mutations in Cancer (COSMIC) (Forbes, et al.; COSMIC: somatic cancer genetics at high-resolution. Nucleic Acids Res 2017; 45 (D1): D777-D783. doi: 10.1093/nar/gkw1121) and .mycancergenome.org. In certain embodiments, any of these known mutations may be detected depending on the cancer type.

The tumor sample may be obtained before a cancer treatment. The method may further comprise obtaining a sample after treatment and comparing the presence of clonal populations before and after treatment, wherein clonal populations of cells sensitive and resistant to the treatment are identified. The method may comprise determining mutations and subclonal populations on at least one time point after administration of the therapy. The at least one time point may be a week, a month, a year, two years, three years, or five years after initiation of a therapy. The time point may be after a relapse in the disease is detected. Relapse may be any recurrence of symptoms of a disease after a period of improvement. Time points may be taken at any point after the initial treatment of the disease and includes time points following a change to the treatment or after the treatment has been completed.

The cancer treatment may be selected from the group consisting of chemotherapy, radiation therapy, immunotherapy, targeted therapy and a combination thereof.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to an angiogenesis inhibitor, such as angiostatin Kl-3, DL-a-Difluoromethyl-ornithine, endostatin, fumagillin, genistein, minocycline, staurosporine, and thalidomide; a DNA intercalator/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (+)-Amethopterin (Methotrexate), 3-Amino-1,2,4-benzotriazine 1,4-di oxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S (+)-Camptothecin, Curcumin, (−)-Deguelin, 5,6-Dichlorobenzimidazole I-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-a, Rapamycin, Sex hormone-binding globulin, Thapsigargin, Vismodegib (Erivedge™), and Urinary trypsin inhibitor fragment (Bikunin). The antitumor agent may be a monoclonal antibody or antibody drug conjugate, such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Tositumomab and 1311-tositumomab (Bexxar®), ibritumomab tiuxetan (Zevalin®), brentuximab vedotin (Adcetris®), siltuximab (Sylvant™), pembrolizumab (Keytruda®), ofatumumab (Arzerra®), obinutuzumab (Gazyva™), 90Y-ibritumomab tiuxetan, 1311-tositumomab, pertuzumab (Perjeta™), ado-trastuzumab emtansine (Kadcyla™), Denosumab (Xgeva®), and Ramucirumab (Cyramza™). The antitumor agent may be a small molecule kinase inhibitor, such as Vemurafenib (Zelboraf®), imatinib mesylate (Gleevec®), erlotinib (Tarceva®), gefitinib (Iressa®), lapatinib (Tykerb®), regorafenib (Stivarga®), sunitinib (Sutent®), sorafenib (Nexavar®), pazopanib (Votrient®), axitinib (Inlyta®), dasatinib (Sprycel®), nilotinib (Tasigna®), bosutinib (Bosulif®), ibrutinib (Imbruvica™), idelalisib (Zydelig®), crizotinib (Xalkori®), afatinib dimaleate (Gilotrif®), ceritinib (LDK378/Zykadia), trametinib (Mekinist®), dabrafenib (Tafinlar®), Cabozantinib (Cometriq™), vandetanib (Caprelsa®). The antitumor agent may be a proteasome inhibitor, such as bortezomib (Velcade®) and carfilzomib (Kyprolis®). The antitumor agent may be a cytokine such as interferons (INFs), interleukins (ILs), or hematopoietic growth factors. The antitumor agent may be INF-a, IL-2, Aldesleukin IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenalidomide (Revlimid®), belinostat (Beleodaq™), lenalidomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD 137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The immunotherapy may be adoptive cell transfer therapy. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314 (5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis. Additionally, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

The immunotherapy may be an inhibitor of check point protein. Specific check point inhibitors include, but are not limited to anti-CTLA4 antibodies (e.g., Ipilimumab), anti-PD-1 antibodies (e.g., Nivolumab, Pembrolizumab), and anti-PD-L1 antibodies (e.g., Atezolizumab).

Screening

In another aspect, the present invention provides for a method of identifying a cancer therapeutic target. In certain embodiments, clonal populations of cells in a tumor sample are detected. Differential cell states may be identified (e.g., transcriptional or chromatin) between the clonal populations. Cell states present in resistant clonal populations as determined by determining clonal populations after treatment, preferably before and after treatment. The cell states identified between clonal populations can be used to identify a therapeutic target. The cell state may be a differentially expressed gene, differentially expressed gene signature, or a differentially accessible chromatin loci. The current method provides for improved determination of clonal populations of cells, thus differential expression or cell states between clonal populations can be determined. Previous methods may not identify a therapeutic target.

In another aspect, the present invention provides for a method of screening for a cancer treatment. A tumor sample may be obtained from a subject in need thereof. The tumor sample may be grown ex vivo. The tumor sample may be used to generate a patient derived xenograft. Patient derived xenografts (PDX) are models of cancer, where tissue or cells from a patient's tumor are implanted into an immunodeficient mouse. PDX models are used to create an environment that resembles the natural growth of cancer, for the study of cancer progression and treatment. Humanized-xenograft models are created by co-engrafting the patient tumor fragment and peripheral blood or bone marrow cells into a NOD/SCID mouse (Siolas D, Hannon GJ (September 2013). "Patient-derived tumor xenografts: transforming clinical samples into mouse models". Cancer Research (Perspective). 73 (17): 5315-9). The co-engraftment allows for reconstitution of the murine immune system enabling researchers to study the interactions between xenogenic human stroma and tumor environments in cancer progression and metastasis (Talmadge J E, Singh R K, Fidler I J, Raz A (March 2007). "Murine models to evaluate novel and conventional therapeutic strategies for cancer". The American Journal of Pathology (Review). 170 (3): 793-804). Clonal populations may be detected in the tumor sample. The tumor sample or mouse model can be treated according to the standard of care for the cancer (e.g., targeting BCR-ABL in CML). The effect of the treatment on the clonal populations can be determined. In one embodiment, it can be determined that the treatment will be effective for the subject's tumor. The effect of the treatment on the clonal populations can be determined and differentially expressed genes between resistant and sensitive clonal populations can be used to determine therapeutic targets. Determining the effects on clonal populations may be determined by measuring expression of a gene signature associated with the clonal populations.

In certain embodiments, tumor clonal structures are measured, cancer therapeutic targets are identified, and/or therapeutics are screened for a specific cancer. In certain embodiments, cancer development is determined by determining clonal structures that lead to cancer. In certain embodiments, clonal structure is determined using an in vivo cancer model.

The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumor including serous tumor, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilms' tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medulloblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Selecting Cell Types

In certain embodiments, the cells obtained from a subject are selected for a cell type. In certain embodiments, stem and progenitor cells are selected. In certain embodiments, progenitor cells specific for generating a specific tissue are identified. In certain embodiments, cells along a lineage specific for generating a specific tissue are identified. In certain embodiments, CD34+ hematopoietic stem and progenitor cells may be selected (e.g., to study blood diseases).

In certain embodiments, the method further comprises determining a lineage and/or clonal structure for single cells from two or more tissues and identifying tissue specific mitochondrial mutations for the subject. In certain embodiments, the related cell types are from a tumor sample. In certain embodiments, peripheral blood mononuclear cells (PBMCs) and/or bone marrow mononuclear cells (BMMCs) are selected. The PBMCs and/or BMMCs may be selected before and after stem cell transplantation in a subject.

In certain embodiments, lineages or clonal structures for populations of immune cells may be determined (e.g., T cells specific for an antigen).

The term "immune cell" generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes such as natural killer cells, T-cells (including, e.g., thymocytes, Th or Tc; Th1, Th2, Th17, Thαβ, CD4+, CD8+, effector Th, memory Th, regulatory Th, CD4+/CD8+ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

The present invention provides a novel analytic framework, methods and systems that are widely applicable across diseases, and specifically different types of cancer. The present invention provides for the detection and grouping of subclonal populations of cells or disease causing entities based upon mitochondrial mutations present in each cell or disease causing entity. The subclones may be present in less than 10%, less than 5%, less than 1%, less than 0.1%, less than 0.01%, less than 0.001% or less than 0.0001% of the diseased cells or malignant cells. The disease can be any disease where drug resistance mutations occur or where clonal evolution occurs.

In one aspect, the present invention provides a method of individualized or personalized treatment for a disease undergoing clonal evolution and for preventing relapse after treatment in a patient in need thereof comprising: determining mutations present in a disease cell fraction from the patient before and/or after administration of a therapy; determining subclonal populations within the disease cell fraction; and selecting at least one subclonal population to treat.

The invention is further described in the following examples, which do not limit the scope of the invention described in the claims.

EXAMPLES

Figure 22:
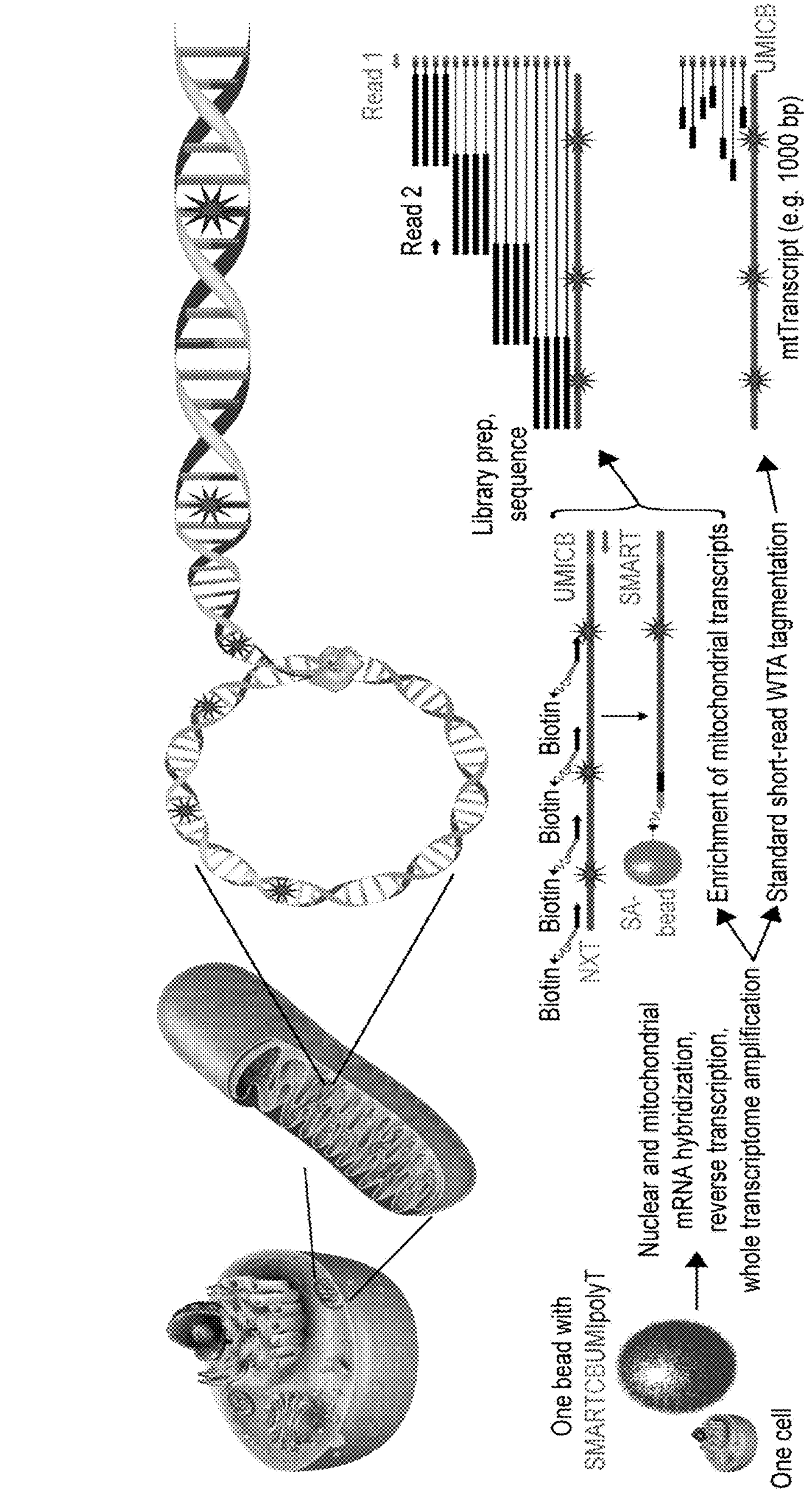
FIG. 22—Diagram shows the procedures for lineage inference from single-cell transcriptomes. The top depicts how cells contain mitochondria which contain circular mitochondrial genomes. Somatic mutations that occur in these mitochondrial genomes can serve as heritable barcodes to reconstruct cellular ancestry. Most of the mitochondrial genome is transcribed into RNA and can therefore be captured with RNA-seq technologies. The bottom depicts how individual cells are physically isolated with beads that are coated with oligonucleotides. In this case, the oligonucleotides contain a SMART PCR handle, cell barcode (CB) to identify the originating cell, unique molecular identifier (UMI) to identify unique transcripts and a polyT sequence to capture RNA molecules by their polyA sequences. The bead and oligonucleotide can vary between single-cell RNA-seq technologies. RNA hybridization, reverse transcription (RT) and whole transcriptome amplification (WTA) results in a library of complementary DNA (cDNA) molecules tagged with the CB and UMI. Mitochondrial transcripts are enriched using primers that are specifically designed to amplify RNAs that were transcribed from the mitochondrial genome. Next-generation or long-read sequencing can be used to link variants in the mitochondrial transcripts (and genome) to cell lineages. In parallel, the WTA product can be used for single-cell RNA-seq using standard procedures such as Seq-Well or 10× Genomics single-cell gene expression assays.

Example 1—Enriching Mitochondrial Transcripts from High-Throughput Single Cell RNA-Seq WTA Products and Lineage Tracing Applicants have determined improved methods to use the WTA product from high throughput single cell RNA sequencing, Mitochondrial Alteration Enrichment from Single-cell Transcriptomes to Establish Relatedness (Maester) (FIG. 22). The method advantageously provides for enrichment of mitochondrial transcripts from the WTA product. The specific enrichment steps disclosed (e.g., amplification with primers specific to the mitochondrial genome) is required to be compatible with high-throughput single-cell RNA-sequencing protocols (droplet or microwells, i.e. Seq-Well, Drop-Seq, 10×).

FIG. 1 shows experimental overview for acquiring transcriptional, genotypic, and lineage and/or clonal structure information from high-throughput single cell RNA-seq libraries. A single WTA product can be used for determining gene expression, mitochondrial genotypes and nuclear genotypes. Mitochondrial transcripts from patient OCI-AML3 were enriched from a single cell WTA library by PCR using the primers from Table 1 (see, also FIG. 4) and a universal reverse primer in the following PCR reactions:

TABLE 3

| PCR Reactions for enriching mtDNA transcripts | |
|---|---|
| PCR1-10 | 10 ng WTA with primer mix 1 |
| PCR1-100 | 100 ng WTA with primer mix 1 |
| PCR2 | 10 ng WTA with primer mix 2 |
| PCR3 | 10 ng WTA with primer mix 3 |

TABLE 4

Primer Mix compositions for PCR Reactions

| | To detect mutations in | | | Primers | | | Stock (µM) | Use (µl) | Final (µM) | H2O (µl) |
|---|---|---|---|---|---|---|---|---|---|---|
| Mix 1 | | | | SMART | _ | Rev | 100 | 15 | 3 | |
| | MT-RNR1 | Transcript start at | 702 | MT-RNR1 | _ | 702 | 100 | 1 | 0.2 | |
| | MT-RNR2 | Transcript start at | 1679 | MT-RNR2 | _ | 1679 | 100 | 1 | 0.2 | |
| | MT-ND1 | Transcript start at | 3320 | MT-ND1 | _ | 3320 | 100 | 1 | 0.2 | |
| | MT-ND2 | Transcript start at | 4483 | MT-ND2 | _ | 4483 | 100 | 1 | 0.2 | |
| | MT-CO1 | Transcript start at | 5910 | MT-CO1 | _ | 5910 | 100 | 1 | 0.2 | |
| | MT-CO2 | Transcript start at | 7609 | MT-CO2 | _ | 7609 | 100 | 1 | 0.2 | |
| | MT-ATP8 | Transcript start at | 8367 | MT-ATP8 | _ | 8367 | 100 | 1 | 0.2 | |
| | MT-ATP6 | Transcript start at | 8541 | MT-ATP6 | _ | 8541 | 100 | 1 | 0.2 | |
| | MT-CO3 | Transcript start at | 9210 | MT-CO3 | _ | 9210 | 100 | 1 | 0.2 | |
| | MT-ND3 | Transcript start at | 10084 | MT-ND3 | _ | 10084 | 100 | 1 | 0.2 | |
| | MT-ND4L | Transcript start at | 10496 | MT-ND4L | _ | 10496 | 100 | 1 | 0.2 | |
| | MT-ND4 | Transcript start at | 10761 | MT-ND4 | _ | 10761 | 100 | 1 | 0.2 | |
| | MT-NDS | Transcript start at | 12360 | MT-NDS | _ | 12360 | 100 | 1 | 0.2 | |
| | MT-ND6 | Transcript start at | 14664 | MT-ND6 | _ | 14664 | 100 | 1 | 0.2 | |
| | MT-CYB | Transcript start at | 14751 | MT-CYB | _ | 14751 | 100 | 1 | 0.2 | 470 |
| Mix 2 | | | | SMART | _ | Rev | 100 | 15 | 3 | |
| | MT-RNR1 | Transcript start at | 952 | MT-RNR1 | _ | 952 | 100 | 1.36 | 0.27 | |
| | MT-RNR2 | Transcript start at | 1985 | MT-RNR2 | _ | 1985 | 100 | 1.36 | 0.27 | |

TABLE 4-continued

Primer Mix compositions for PCR Reactions

| | To detect mutations in | | | Primers | | | Stock (μM) | Use (μl) | Final (μM) | H2O (μl) |
|---|---|---|---|---|---|---|---|---|---|---|
| | MT-ND1 | Transcript start at | 3635 | MT-ND1 | _ | 3635 | 100 | 1.36 | 0.27 | |
| | MT-ND2 | Transcript start at | 4787 | MT-ND2 | _ | 4787 | 100 | 1.36 | 0.27 | |
| | MT-CO1 | Transcript start at | 6216 | MT-CO1 | _ | 6216 | 100 | 1.36 | 0.27 | |
| | MT-CO2 | Transcript start at | 7852 | MT-CO2 | _ | 7852 | 100 | 1.36 | 0.27 | |
| | MT-ATP6 | Transcript start at | 8795 | MT-ATP6 | _ | 8795 | 100 | 1.36 | 0.27 | |
| | MT-CO3 | Transcript start at | 9316 | MT-CO3 | _ | 9316 | 100 | 1.36 | 0.27 | |
| | MT-ND4 | Transcript start at | 11126 | MT-ND4 | _ | 11126 | 100 | 1.36 | 0.27 | |
| | MT-ND5 | Transcript start at | 12831 | MT-ND5 | _ | 12831 | 100 | 1.36 | 0.27 | |
| | MT-CYB | Transcript start at | 15088 | MT-CYB | _ | 15088 | 100 | 1.36 | 0.27 | 470 |
| Mix 3 | | | | SMART | _ | Rev | 100 | 3 | 3 | |
| | MT-RNR2 | Transcript start at | 2411 | MT-RNR2 | _ | 2411 | 100 | 0.75 | 0.75 | |
| | MT-CO1 | Transcript start at | 6540 | MT-CO1 | _ | 6540 | 100 | 0.75 | 0.75 | |
| | MT-ND4 | Transcript start at | 11410 | MT-ND4 | _ | 11410 | 100 | 0.75 | 0.75 | |
| | MT-ND5 | Transcript start at | 13069 | MT-ND5 | _ | 13069 | 100 | 0.75 | 0.75 | 94 |

Figure 2:
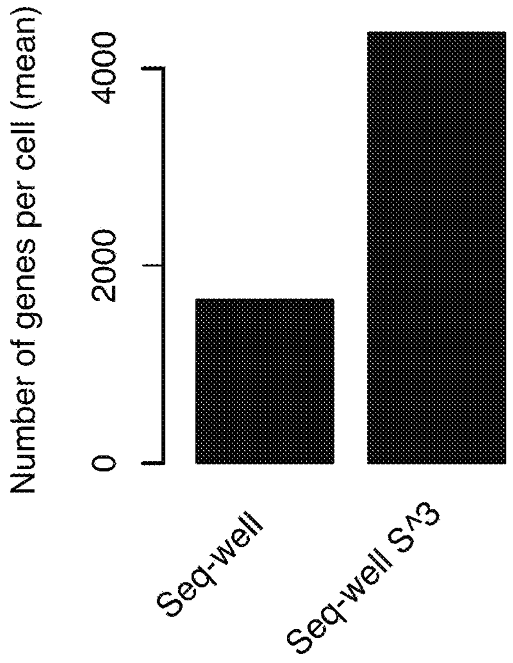
FIG. 2—Single cell RNA-seq libraries obtained using Seq-well and improved Seq-well. Graph showing the mean number of genes read per cell.
Figure 3:
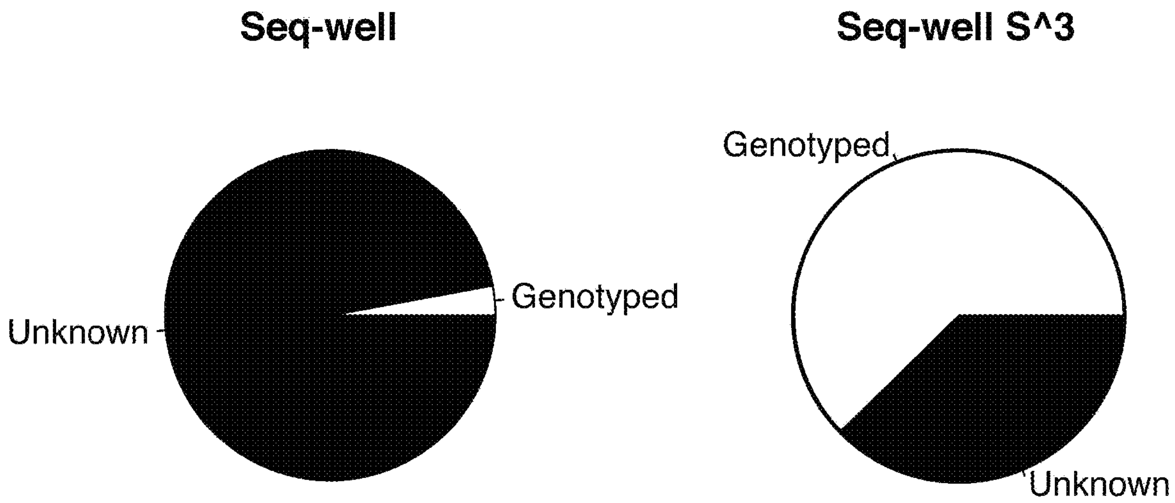
FIG. 3—Improved DNMT3A 2644C>T capture. Pie charts show fraction of genotyped cells in AML samples with the original Seq-well protocol and in OCI-AML3 cells with Seq-well S^3.

FIG. 2 shows that an improved Seq-well protocol (Hughes et al., 2019) provides increased detection of genes per cell than previous methods. From one array, Applicants obtained 3,641 OCI-AML3 cells with at least 2,000 UMIs and 1,000 genes. FIG. 3 shows that the improved Seq-well protocol allows genotyping of low expressed genes (e.g., DNMT3A). The percent of cells in which Applicants captured 0 transcripts went from 97.1% to 37.7%.

Figure 5:
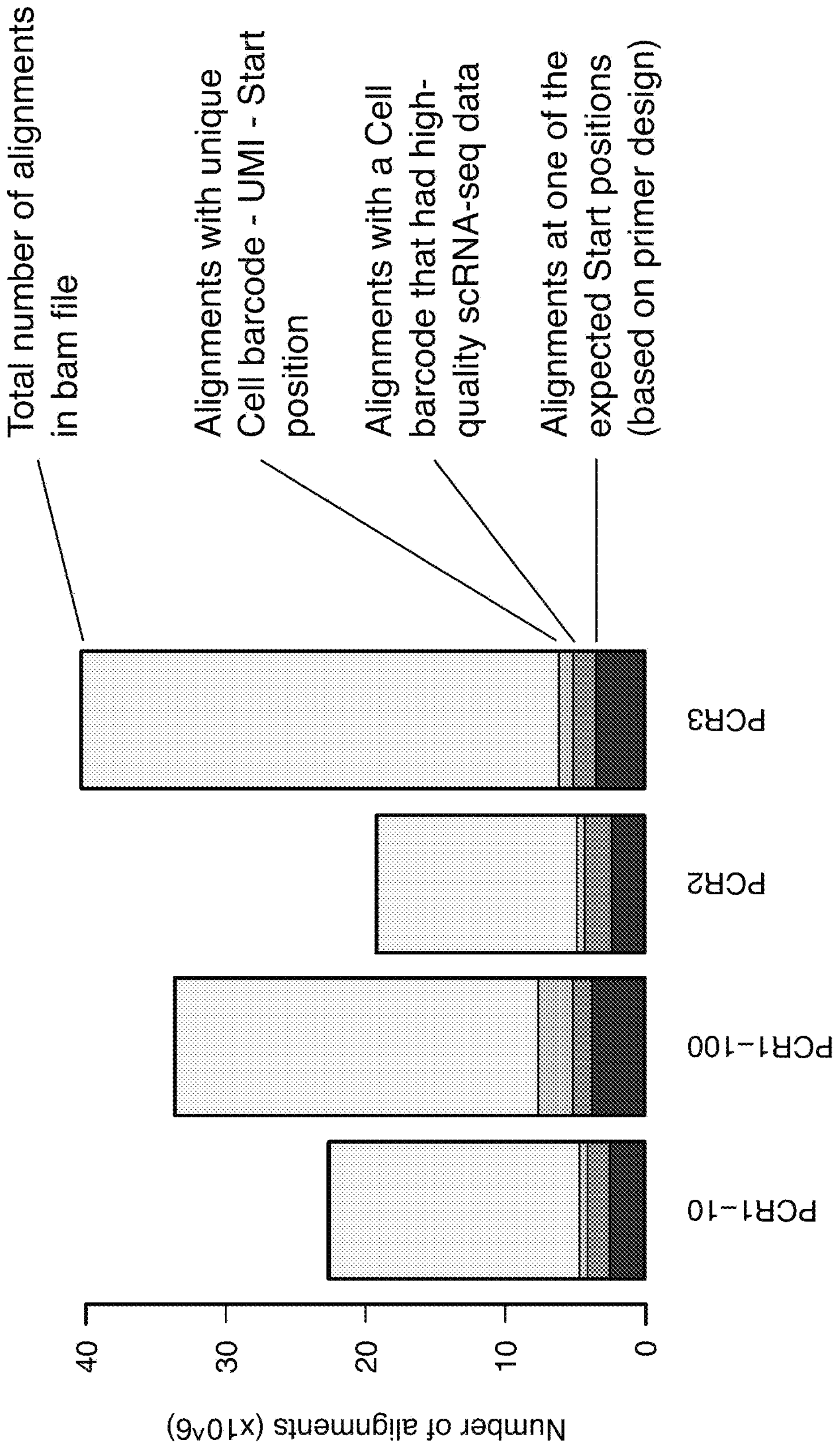
FIG. 5—Filtering mitochondrial alignments. Graph showing the number of alignments for the indicated PCR enrichment reaction after each filtering parameter (see, Table 2 and 3). Filtering is preceded by aligning fastq reads to the mitochondrial genome.
Figure 6:
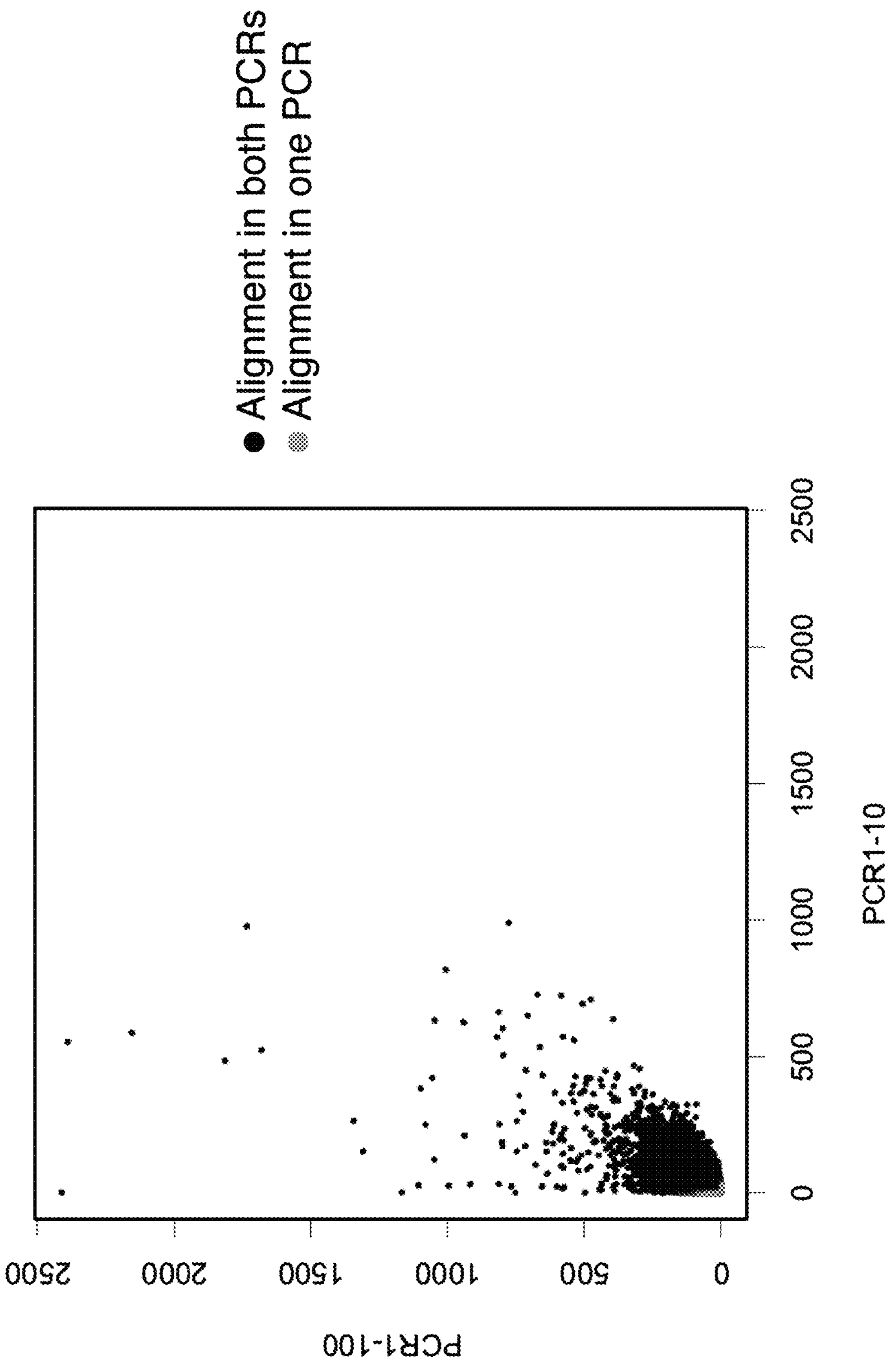
FIG. 6—Correlating libraries to assess PCR bias. Plot showing the number of reads for each alignment. Alignment equals unique combination of Cell barcode+UMI+Start position.
Figure 7:
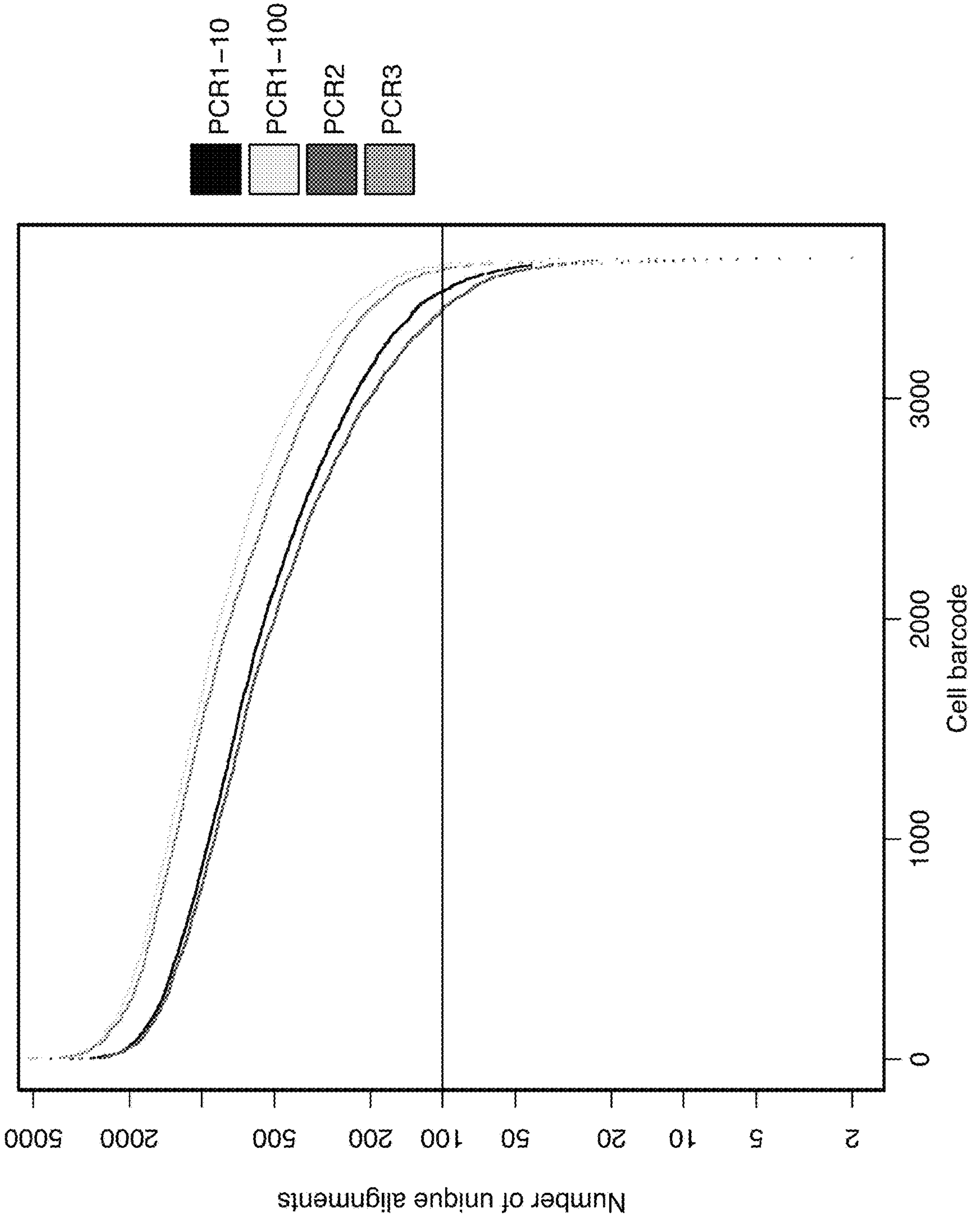
FIG. 7—Number of alignments per cell. Plot showing the number of alignments to the mitochondrial genome from each PCR reaction. Each cell barcode indicates a single cell.
Figure 8:
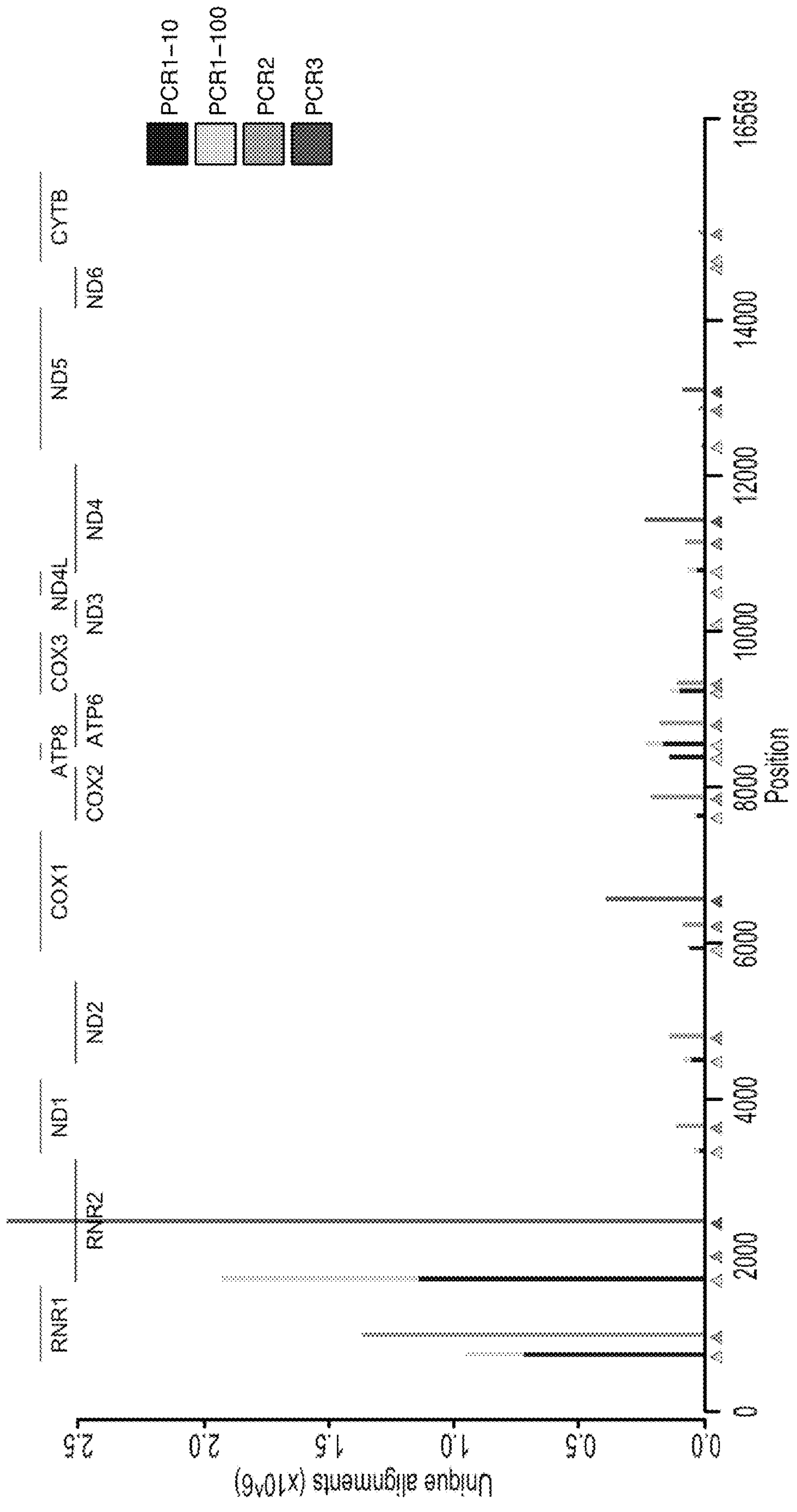
FIG. 8—Number of alignments along the mitochondrial genome. Graph showing the position along the mitochondrial genome vs. the number of alignments. Gene locations are shown on top. Primer binding sites for the different PCR reactions are indicated by arrows on the bottom.
Figure 9:
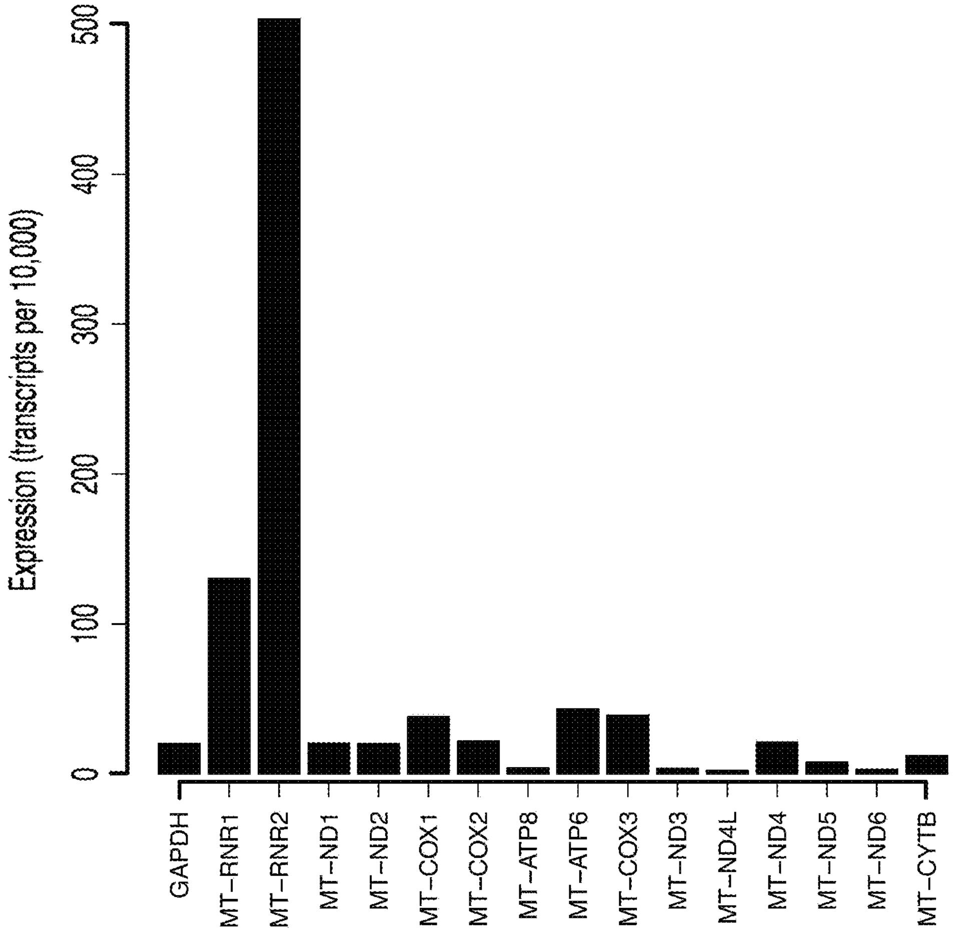
FIG. 9—Expression of mitochondrial genes (from scRNA-seq) correlates to diversity of captured transcripts. Graph showing the expression of mitochondrial genes. Expression is calculated by the number of UMIs from the scRNA-seq that aligns to the gene.
Figure 12:
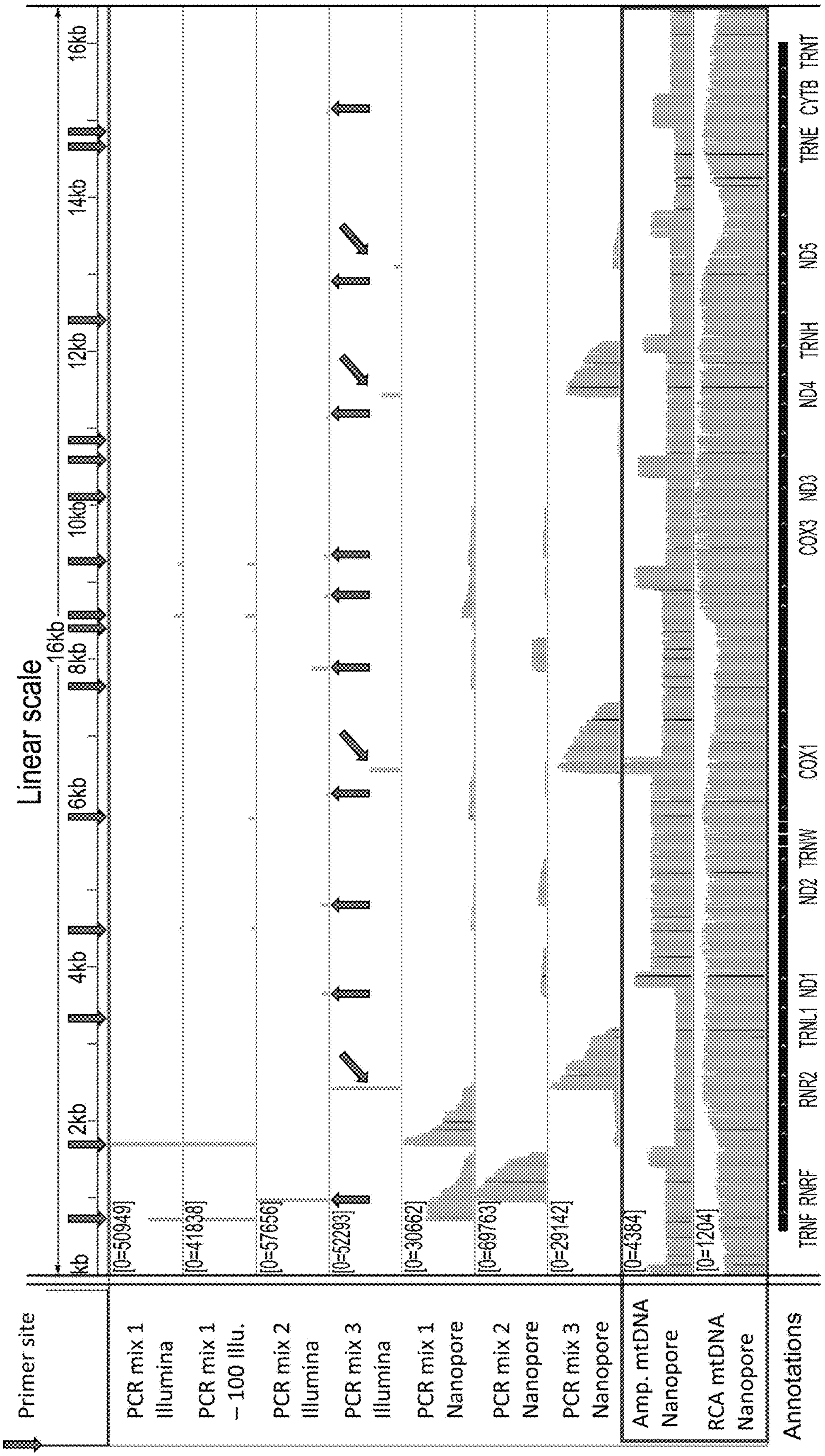
FIG. 12—Identification of informative mtDNA variants using enriched single cell transcripts and bulk sequencing. Plots showing variants along the mitochondrial genome identified using the PCR reactions from single cell WTA product and bulk sequencing of mtDNA (linear scale). The sequencing was Illumina sequencing or nanopore long read sequencing.
Figure 13:
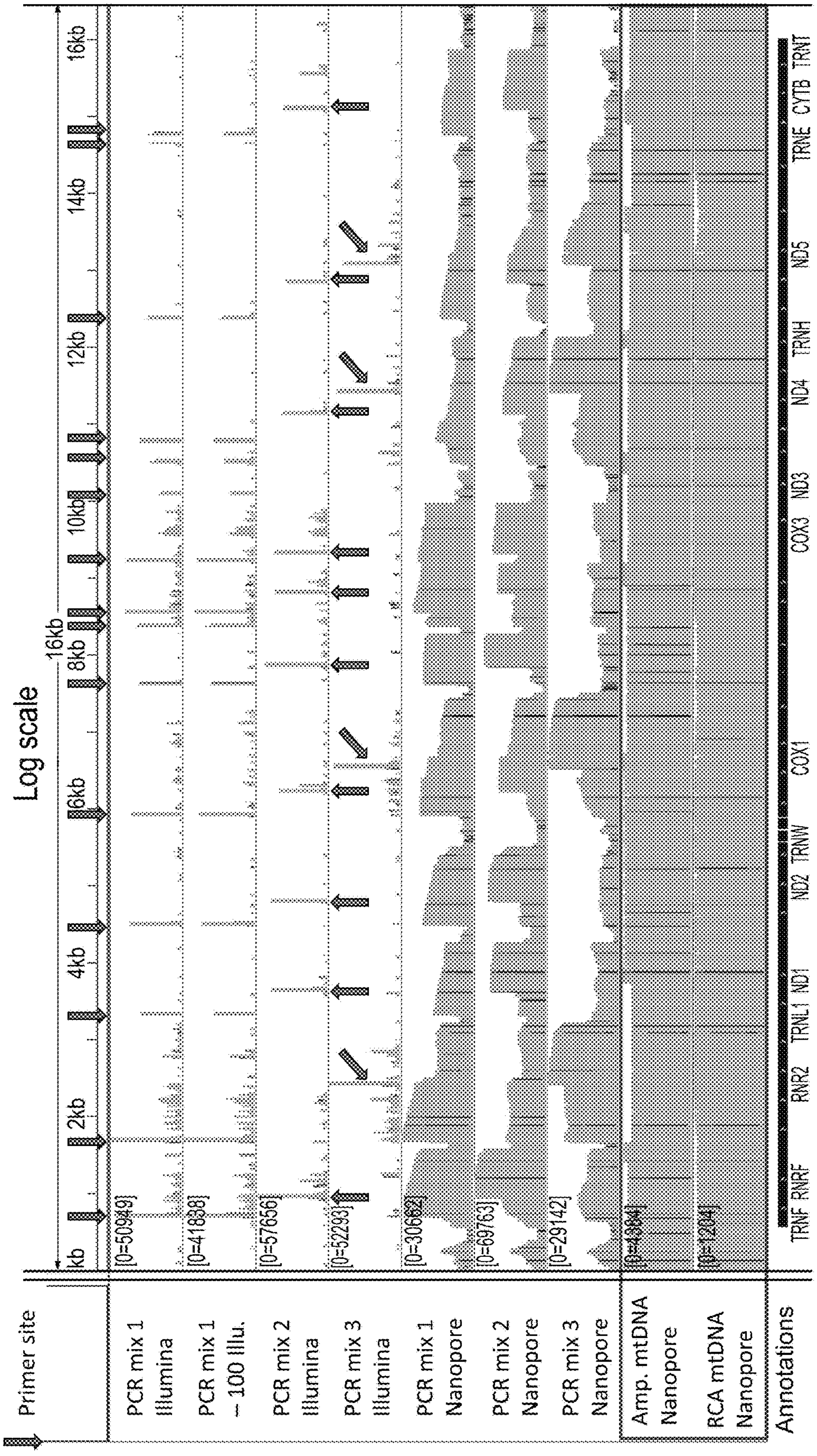
FIG. 13—Identification of informative mtDNA variants using enriched single cell transcripts and bulk sequencing. Plots showing variants along the mitochondrial genome identified using the PCR reactions from single cell WTA product and bulk sequencing of mtDNA (log scale). The sequencing was Illumina sequencing or nanopore long read sequencing.
Figure 14:
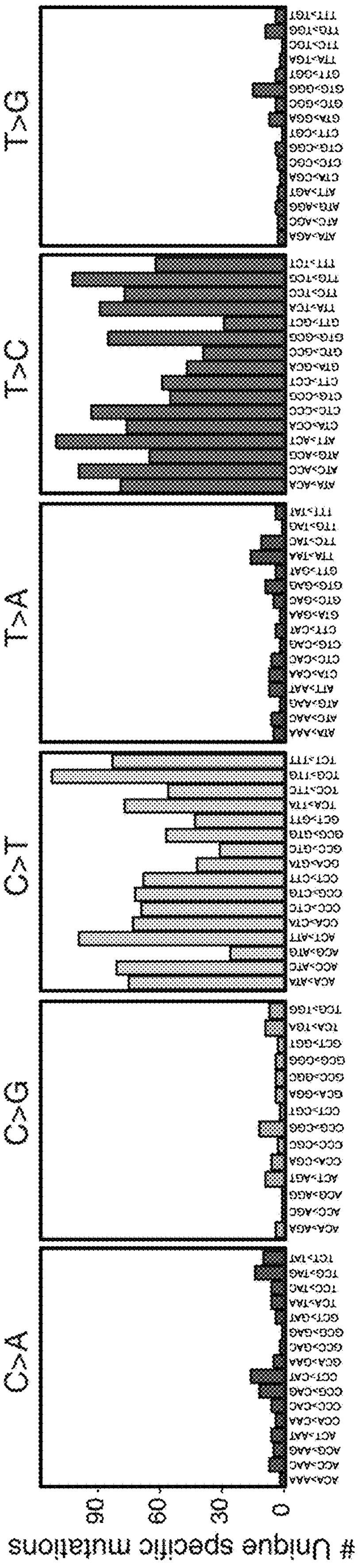
FIG. 14—Coverage and informative variants. Plots showing the number of unique specific mutations for each variant type.

FIG. 5 shows the number of alignments after filtering according to each parameter. Applicants filter the samples in all experiments based on: an alignment=unique combination of Cell barcode+UMI+Start position. Applicants determined the correlation between sequencing libraries (FIG. 6). Correlation between libraries indicates that PCR bias is reproducible, suggesting it could be preexisting in the WTA libraries. However, some reads for each alignment are very different, such as the top left alignment that was read 2× and 2,411×. The average number of reads per alignment is 7.1 for PCR1-10 and 6.7 for PCR1-100. The method provides that the vast majority of cells has >100 alignments to the mitochondrial genome from each PCR reaction (FIG. 7). Applicants also determined that the expression of mitochondrial genes correlates to diversity of captured transcripts, such that the mitochondrial genes having the most alignments are also the most highly expressed (FIGS. 8 and 9). GAPDH is shown for comparison (highly expressed housekeeping gene). 500 of every 10,000 UMIs from the scRNA-seq aligns to MT-RNR2. Applicants were able to identify informative variants using the mitochondrial enrichment and the variants were also present in bulk mitochondrial DNA sequencing (FIGS. 11 and 12). The enriched sequencing libraries were compatible with Illumina and Nanopore sequencing. Applicants also determined the type of variants detected (FIG. 14).

Overall, Applicants detected wide variation in coverage for WTA with the primers. About 30 informative variants were detected. The informative variants had greater than 5% variant allele frequency (VAF) (e.g., heteroplasmy). The majority of variants were C>T mutations, but A>T mutations were also detected. Not all of the variants were the same between bulk mtDNA prepared by the amplicon and RCA methods (FIGS. 10 and 11). For example, some variants found in WTA were not found in bulk mtDNA. This could be due to PCR or sequencing, or editing of RNA. For examples, Applicants observed 2617 A>G, A>T and there is a known 2,619 A>G (see, e.g., Bar-Yaacov, et al., Genome Res. 2013 November; 23 (11): 1789-96).

Figure 15:
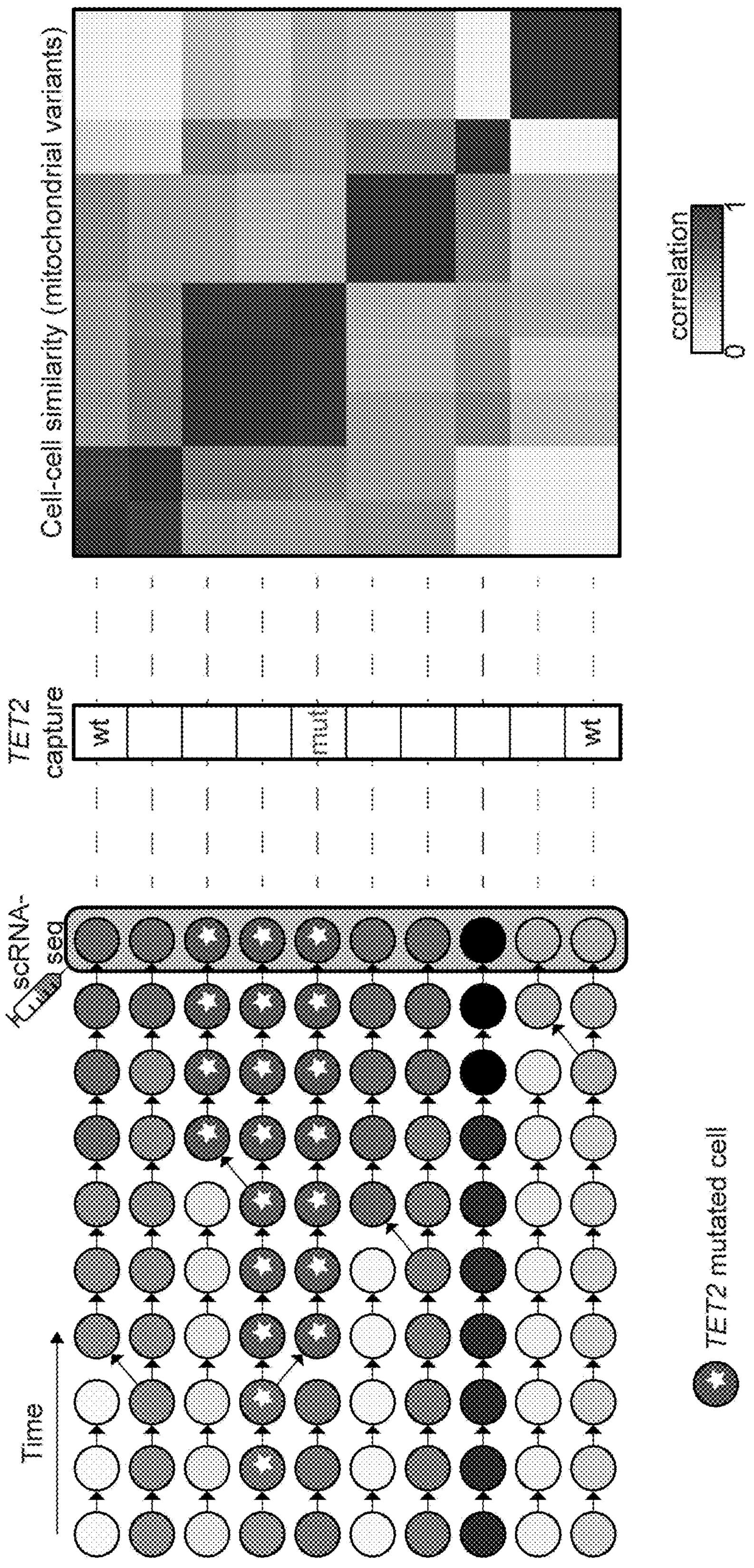
FIG. 15—Lineage tracing in humans to assign cells to subclones. (left) Schematic showing detection of wildtype and TET2 mutation subclones using scRNA-seq. (right) Heatmap showing correlation of subclones based on mitochondrial variants.

FIG. 15 shows that lineage tracing using mitochondrial variants in cells having TET2 mutations can be used to assign cells to subclones. The heatmap shows that the subclones having TET2 mutations show cell-cell similarity based on mitochondrial variants. The mitochondrial variants also identify subclones not having a TET2 mutation.

Figure 16A:
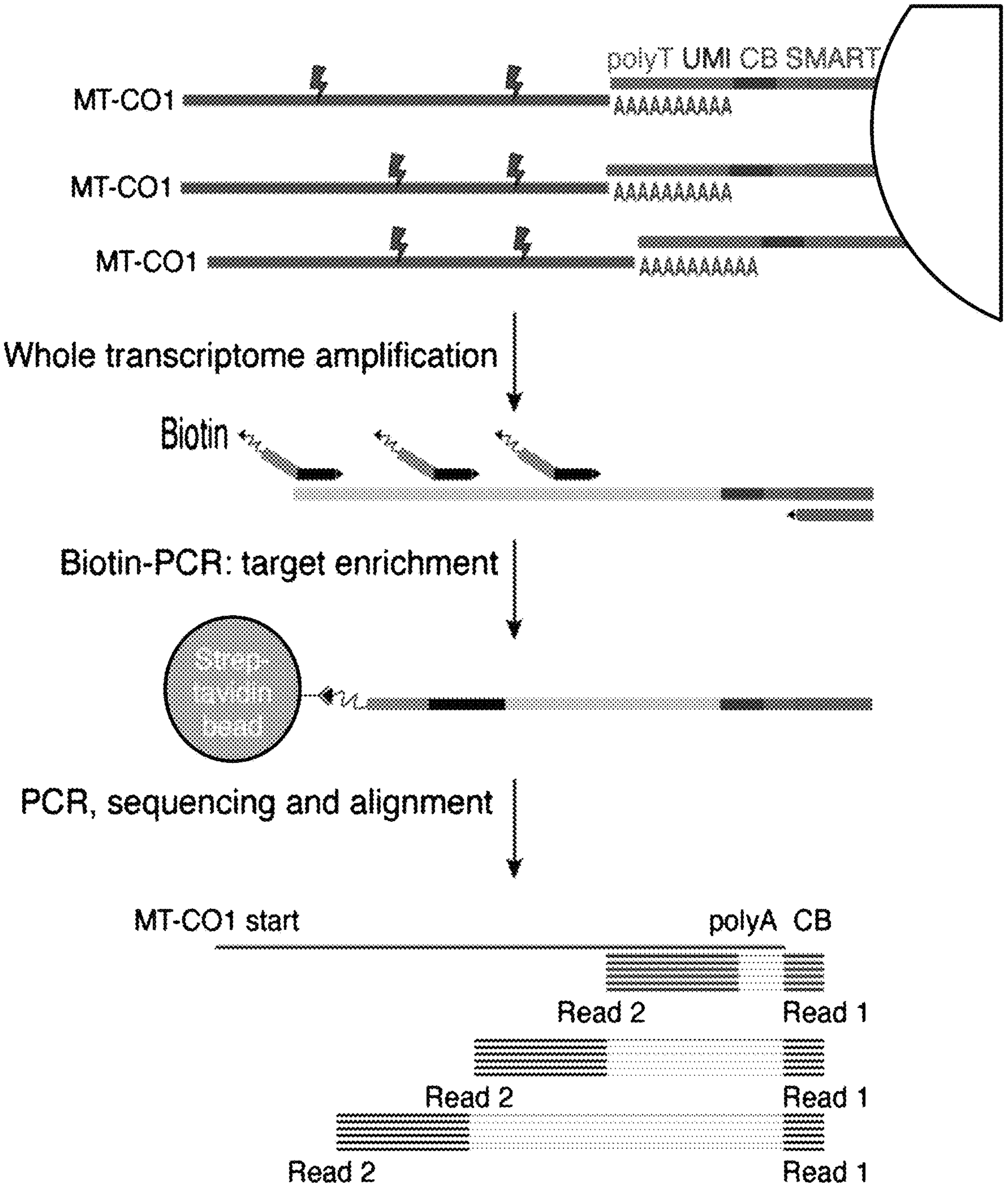
FIG. 16A-FIG. 16B—Enrichment of mitochondrial transcripts to cover informative variants.
Figure 16B:
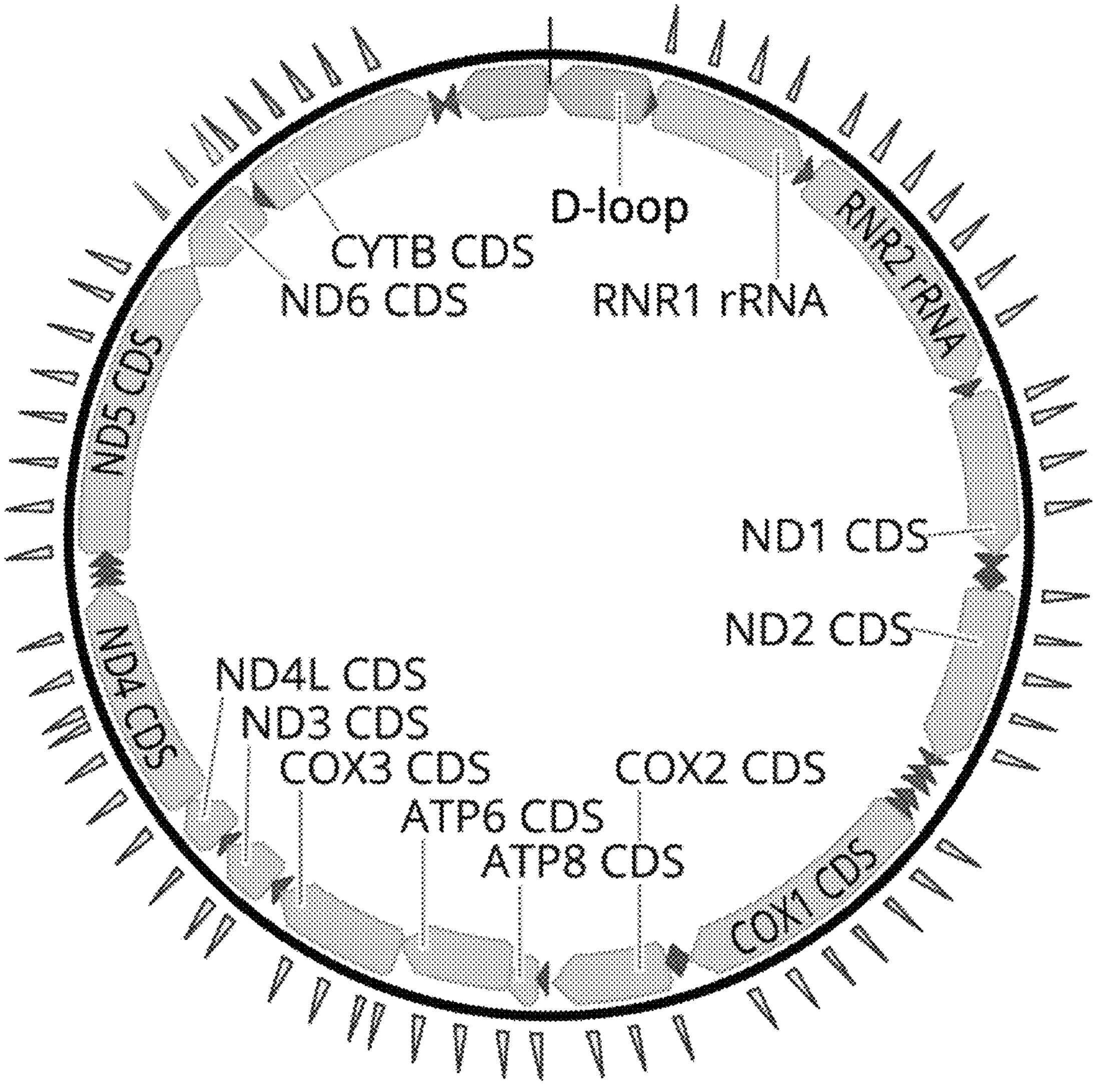
Figure 18:
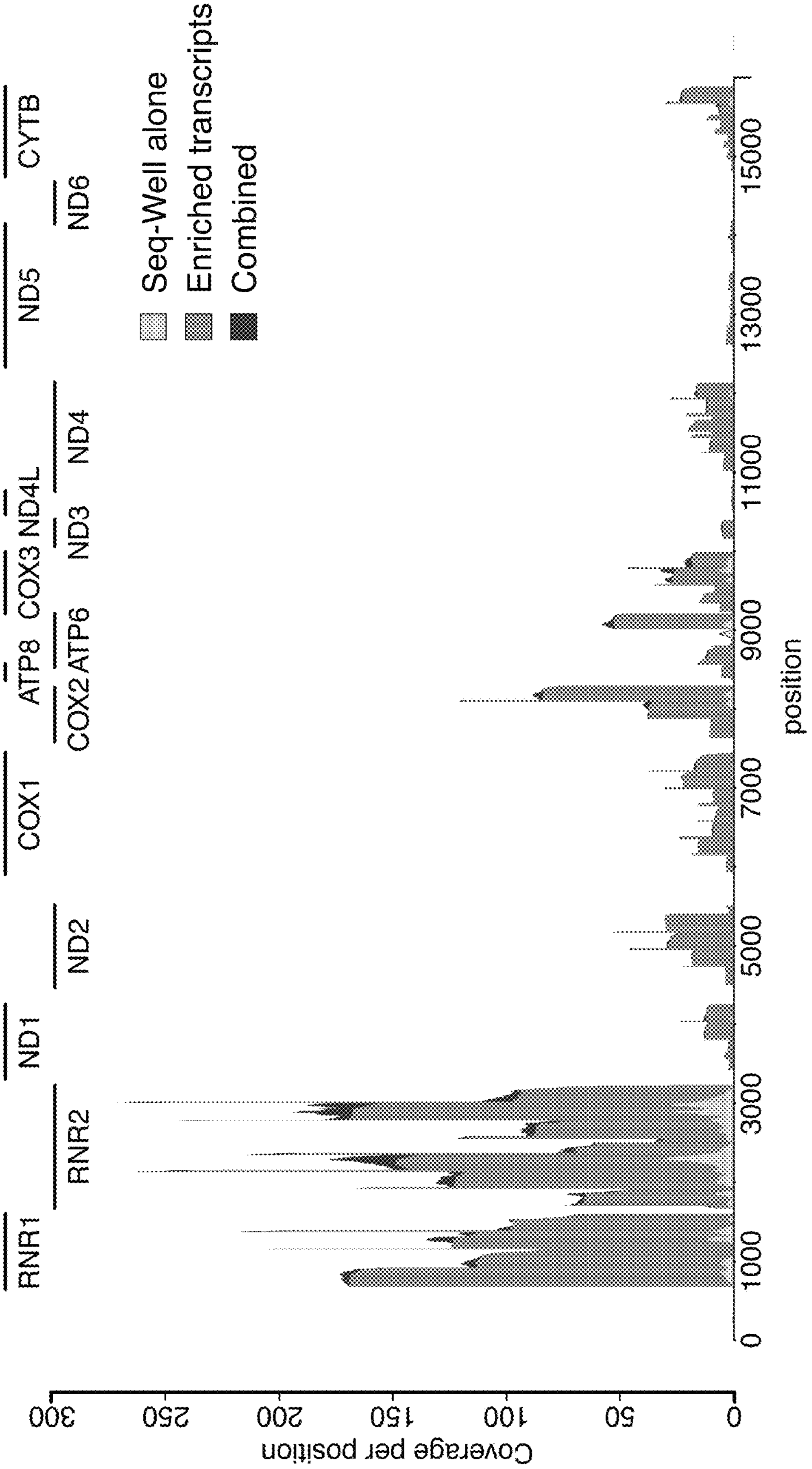
FIG. 18—Increased coverage of mitochondrial genome. Graph showing the coverage of the mitochondrial genome using Seq-well alone, enriched transcripts and combined.
Figure 23:
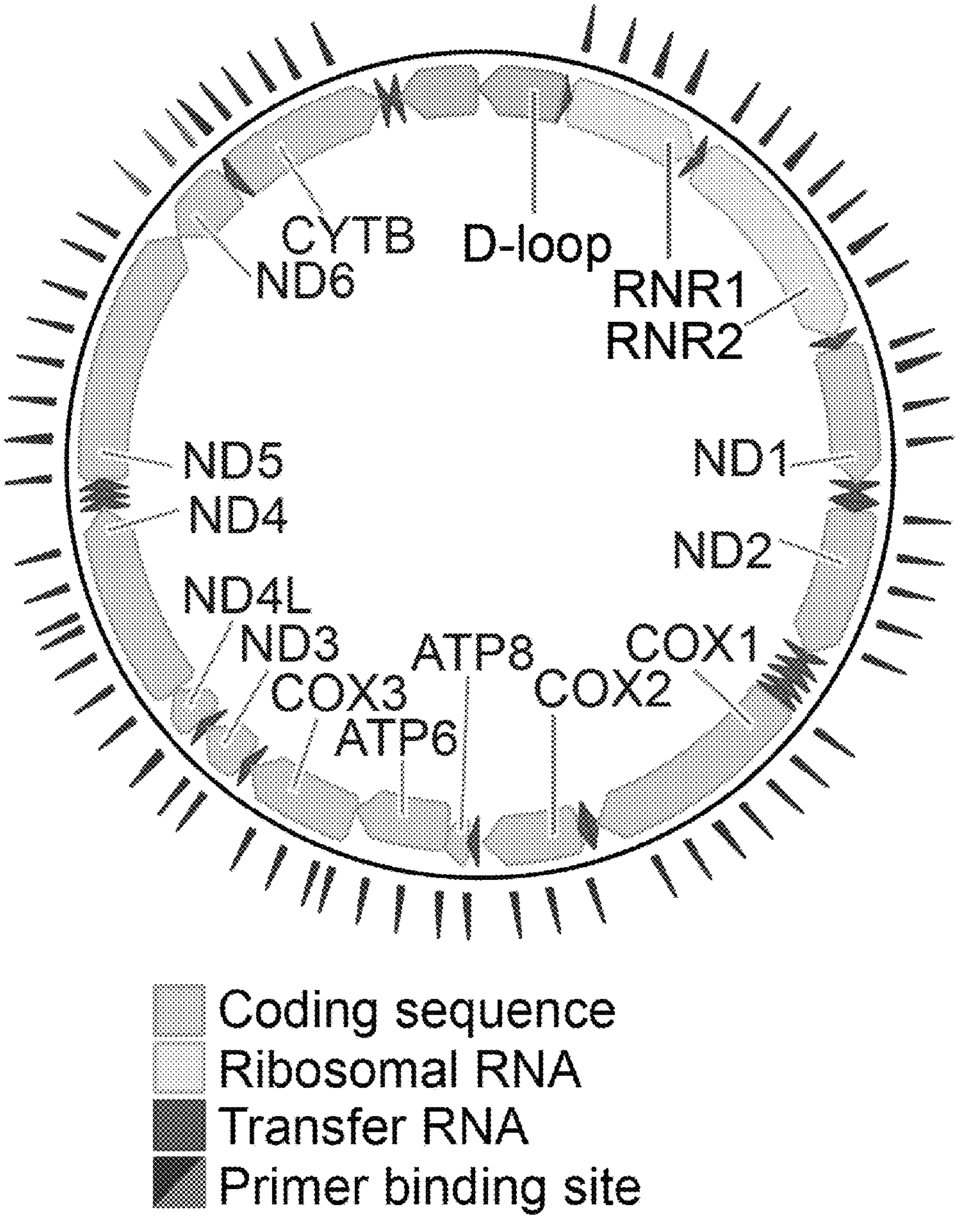
FIG. 23—Diagram depicts the circular mitochondrial genome (NC_012920), which is 16,569 bp, with annotations such as mitochondrial ribosomal RNAs and expressed genes. The triangles outside the circular representation indicate where Applicants designed primers to amplify cDNA derived from RNA that was transcribed from the mitochondrial genome.
Figure 24:
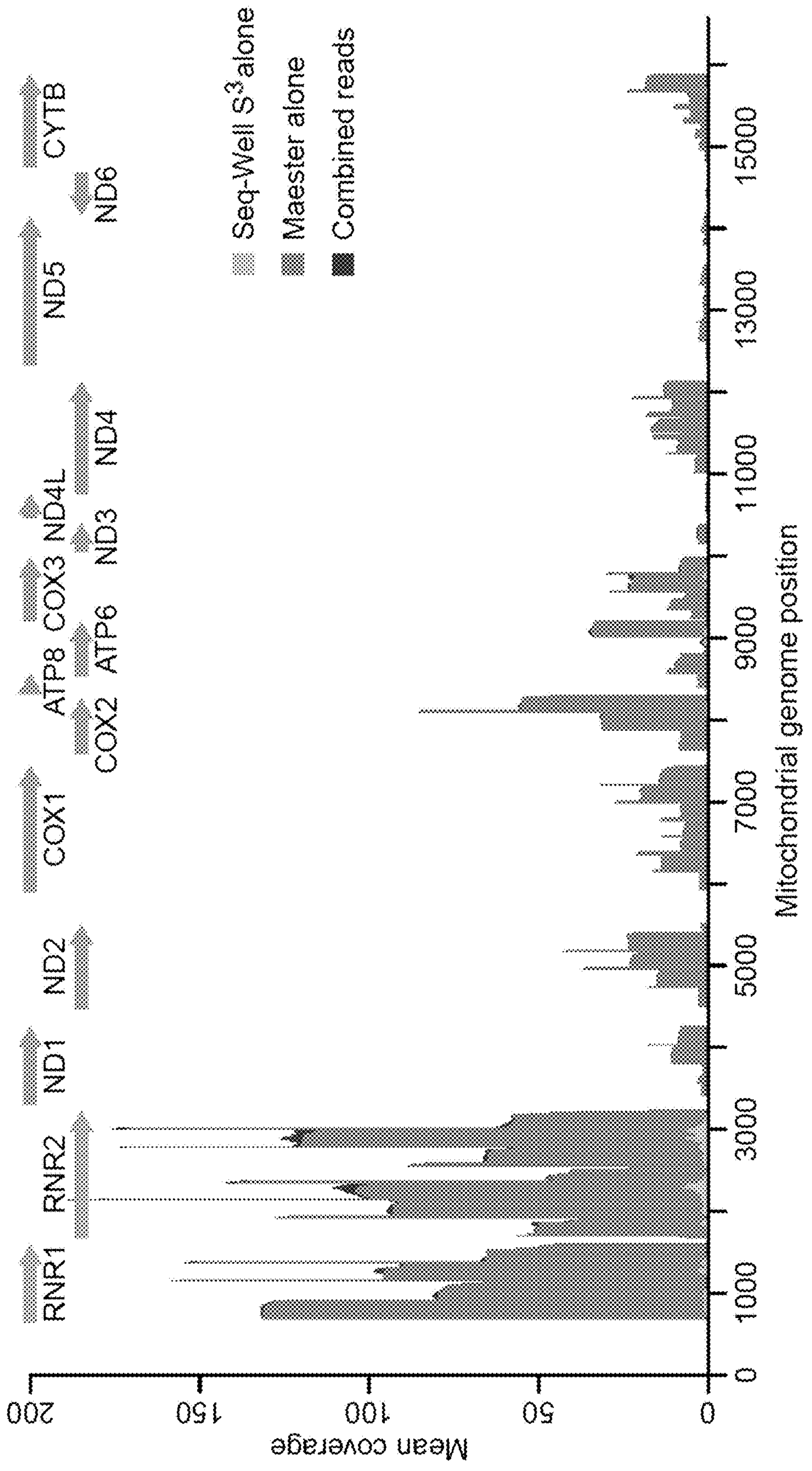
FIG. 24—Bar plot depicts coverage (y-axis) of the mitochondrial genome (x-axis) with and without amplification using the protocol, Mitochondrial Alteration Enrichment from Single-cell Transcriptomes to Establish Relatedness (Maester). Seq-Well alone yields very low coverage along the mitochondrial genome, which is dramatically enhanced using the targeted enrichment procedures. Mean coverage for 2,399 K562 and BT142 cells is shown (minimum 3 reads per UMI).
Figure 25:
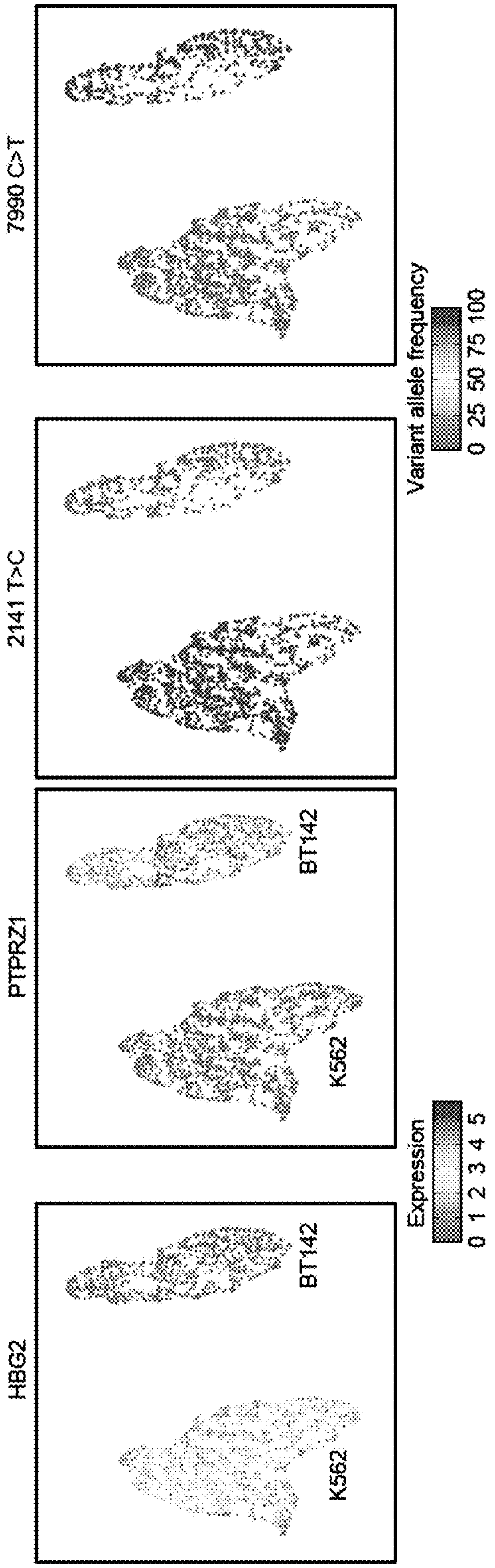
FIG. 25—UMAP plots show detection of genes (top two panels) and mitochondrial variants (bottom two panels) in a cell line mixing experiment. Each symbol represents a cell; x and y coordinates are calculated based on gene expression using standard procedures for single-cell RNA-seq processing. Based on clustering and marker gene expression, Applicants identified 1463 K562 cells and 936 BT142 cells. The identity of these clusters is confirmed by mRNA expression of HGB2, a K562-specific gene in the left cluster, and mRNA expression of PTPRZ1, a BT142-specific gene in the right cluster. Using the enrichment procedures, Applicants found the mitochondrial variant 2141 T>C to be specifically detected in K562 cells, whereas the variant 7990 C>T was specifically detected in BT142 cells.

FIGS. 16A and 22 show an experimental overview for identifying mtDNA variants from high-throughput single cell RNA-seq libraries (e.g., Seq-well). Transcripts from single cells are captured on barcoded beads. The captured transcripts are extended by reverse transcription and the cDNA is subjected whole transcriptome amplification (WTA). The amplified cDNA is subjected to Biotin-PCR to enrich for the mtDNA transcripts. The PCR primers are described in Tables 1 and 2 (also, FIG. 16B and FIG. 23) The forward primers can be 5' labeled with biotin. After amplification with the forward and reverse primers the targets can be captured using streptavidin beads. Enrichment of transcripts provides for increased coverage of the mitochondrial genome (FIG. 18 and FIG. 24).

Table 2 also provides for primers that are optimized for enrichment from single cell sequencing libraries (e.g., Seq-well, 10×). The primers are designed about 250 bp apart so that all bases can be captured using the Illumina NovaSeq 300 cycle kit. The "transcript binding sequence" is targeted to mitochondrial transcripts. In the "Complete sequence" column, additional bases are added that serve as primer binding sites for a subsequent PCR to generate Illumina compatible libraries. Primers can be pooled ("Mix" column) to conserve input material and decrease labor and cost. The mixes were designed and tested to maximize coverage:

1. Never mix two primers targeting the same transcript together, which would cause technical artifacts.
2. Mix together primers that will yield fragments of similar length (i.e. similar distance to the polyA tail), to minimize bias towards shorter fragments during PCR or sequencing.
3. Avoid mixing primers that target transcripts with very different expression levels.

Mix 1: The closest 250 bp to the 3' end.
Mix 2: The region 500-250 bp away from the 3' end.
Mix 3: The region 750-500 bp away from the 3' end.
Mix 4: The region 1000-750 bp away from the 3' end.
Mix 5: The region 1250-1000 bp away from the 3' end.
Mix 6: The region 1500-1250 bp away from the 3' end.
Mix 7: The region 1750-1500 bp away from the 3' end.
Mix 8: The region 2000-1750 bp away from the 3' end.

Mix R1: Most abundant transcripts, all within 250 bp of 3' end.

Mix R2: Most abundant transcripts, all within 500-250 bp of 3' end.

Mix R3: Most abundant transcripts, all within 500-1000 bp of 3' end.

Mix R4: Most abundant transcripts, within 750-1000 bp of 3' end.

Figure 17:
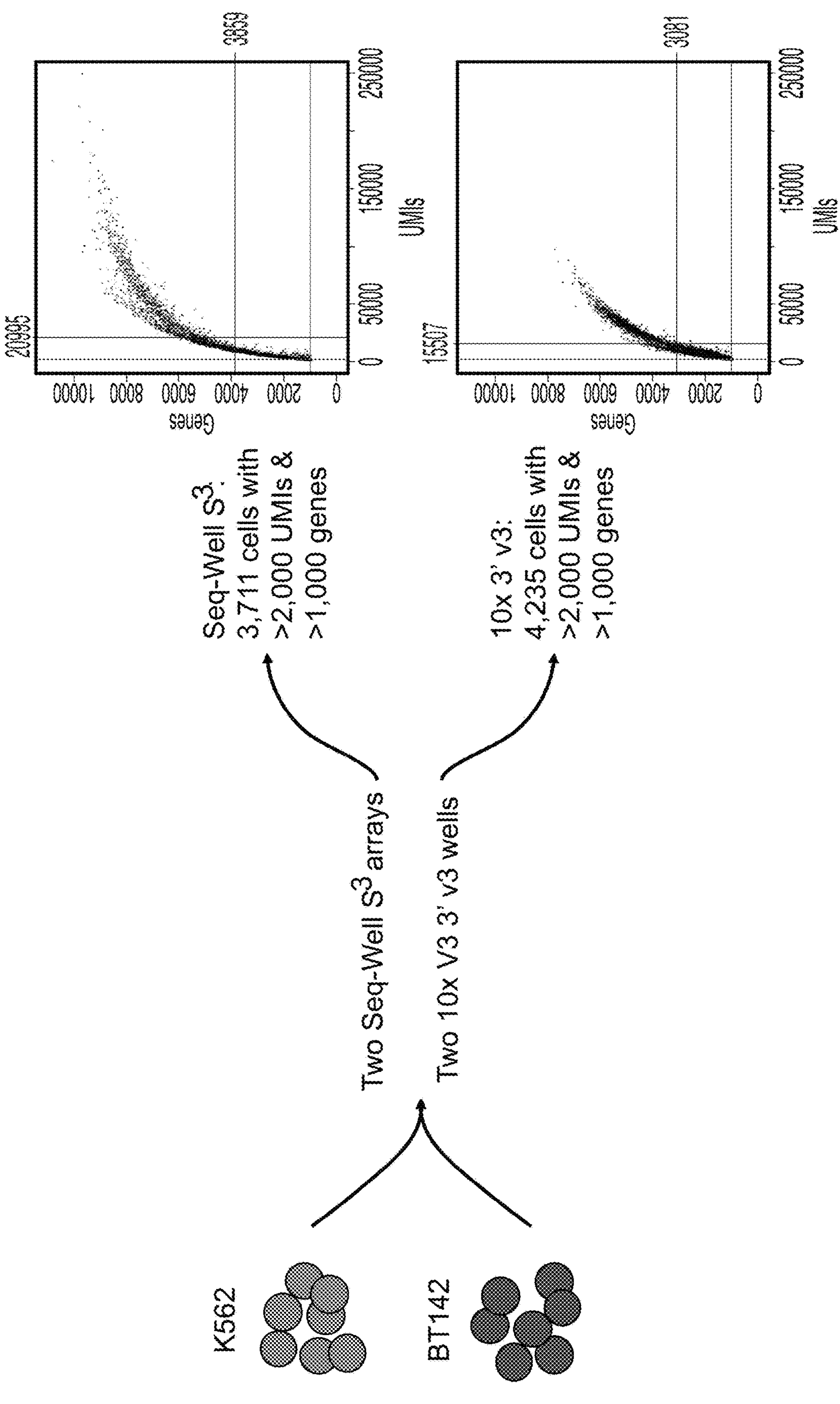
FIG. 17—Cell line mixing experiment for technology validation. Schematic depicts experimental overview for mixing two cell lines and analyzing the cells by either Seq-well or 10× single cell sequencing. Plots show the number of UMIs compared to the number of genes identified by sequencing.
Figure 26:
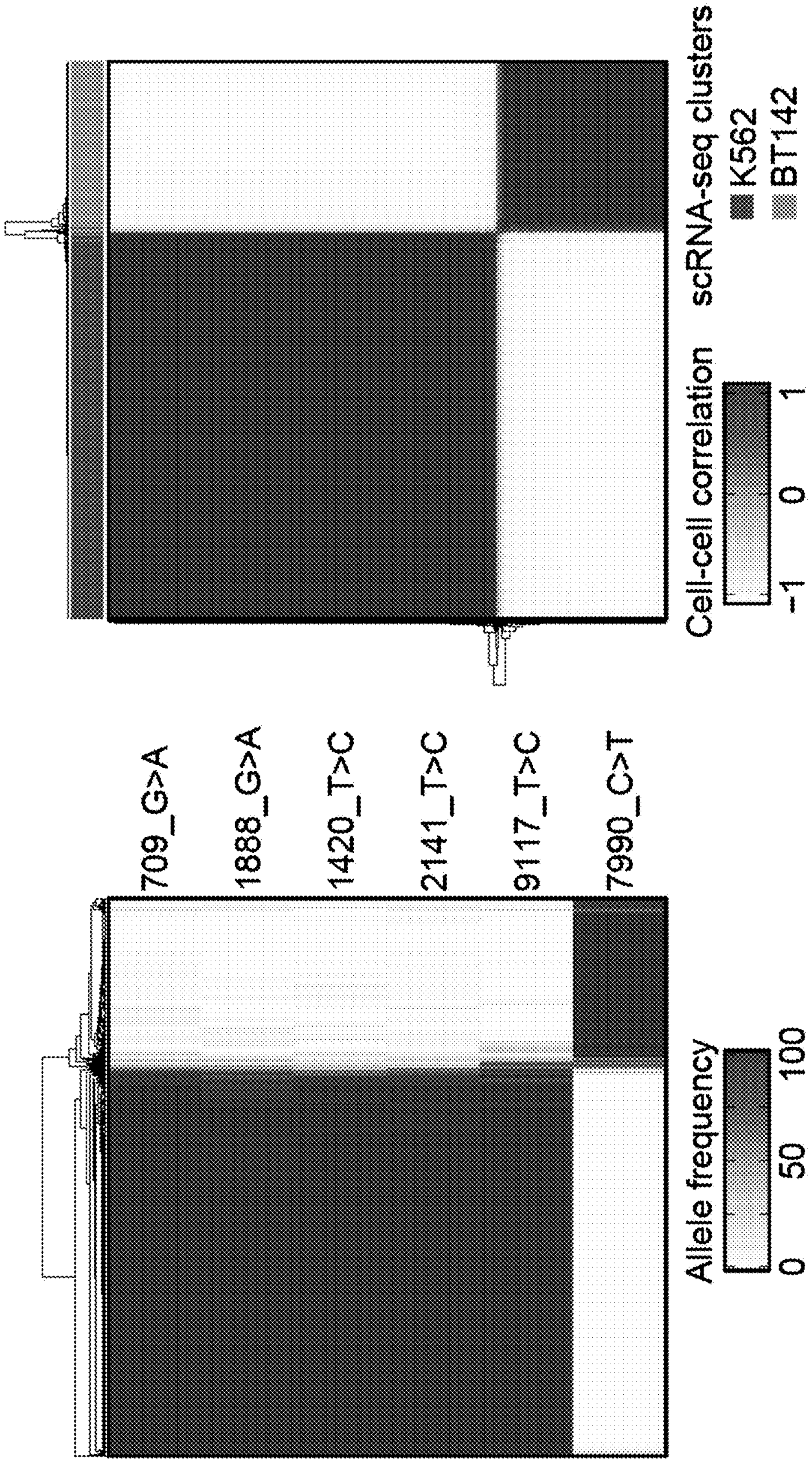
FIG. 26—Heatmaps depict separation of K562 and BT142 cells based on mitochondrial variants detected using Maester. Left: the variant allele frequency (VAF) is shown for six variants (rows) in 1761 high-quality cells (columns). Unsupervised clustering based on these VAFs identified two clusters. Right: correlation matrix shows cell similarity based on the six variants shown in the heatmap on the left (the rows and columns depict 1761 high-quality cells). Two distinct clusters are evident that highly correlate with cell identities as defined by single-cell RNA-seq clustering (shown on top). These results establish the concordance between cell identity based on RNA-seq and the detection of specific mitochondrial variants.

Single cells from two different cell types can be mixed and analyzed by any single cell sequencing method to obtain and count transcripts. FIG. 17 shows a mixing experiment where K562 and BT142 cells are mixed and analyzed by Seq-well and 10× sequencing. For Seq-well 3,711 cells were sequenced with greater than 2,000 UMIs and greater than 1,000 genes. For 10× 4,235 cells were sequenced with greater than 2000 UMIs and greater than 1000 genes. The cells could be clustered by mitochondrial DNA variant allele frequency (FIG. 19A-B, FIG. 25, and FIG. 26). The clustering matched clustering using RNA expression. The cell types could be completely resolved using the clustering based on mitochondrial DNA variants. The mitochondrial variants clustered the same single cells (K562 and BT142) as the cell-cell correlation (e.g., genes go up and down together in cells) (FIG. 26).

Figure 20:
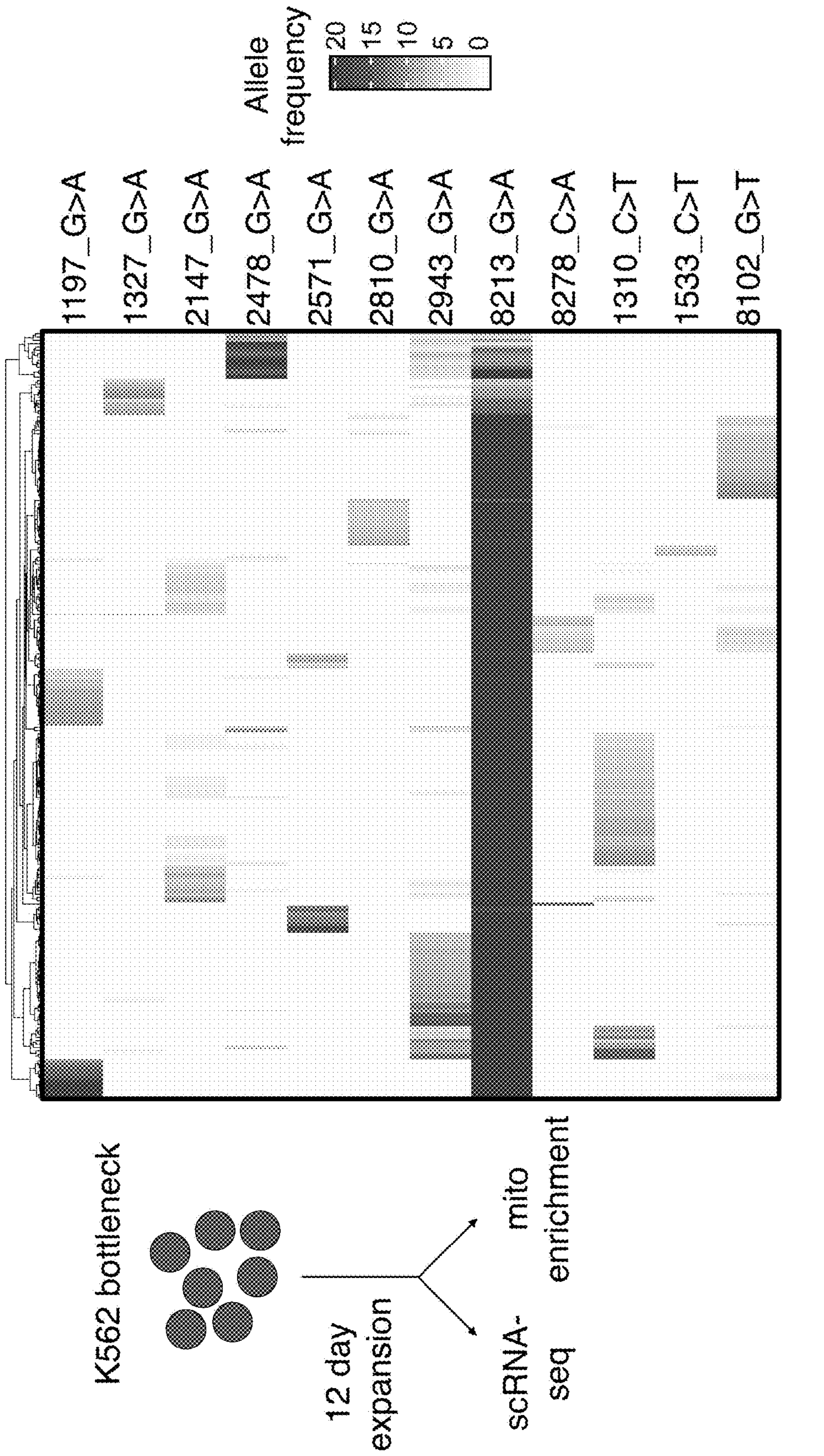
FIG. 20—Clonal structure from mitochondrial variants. (left) Schematic depicts experimental overview for determining the clonal structure of K562 cells after expansion for 12 days. (right) Heatmap showing the mitochondrial variants (rows) identified in the single cells (columns).

FIG. 20 shows that subclones can be identified in K562 cells that have been expanded for 12 days. The cells can be used for transcriptome analysis and mito-enrichment. Subclones were identified having increased allele frequency for specific mitochondrial variants.

Figure 21:
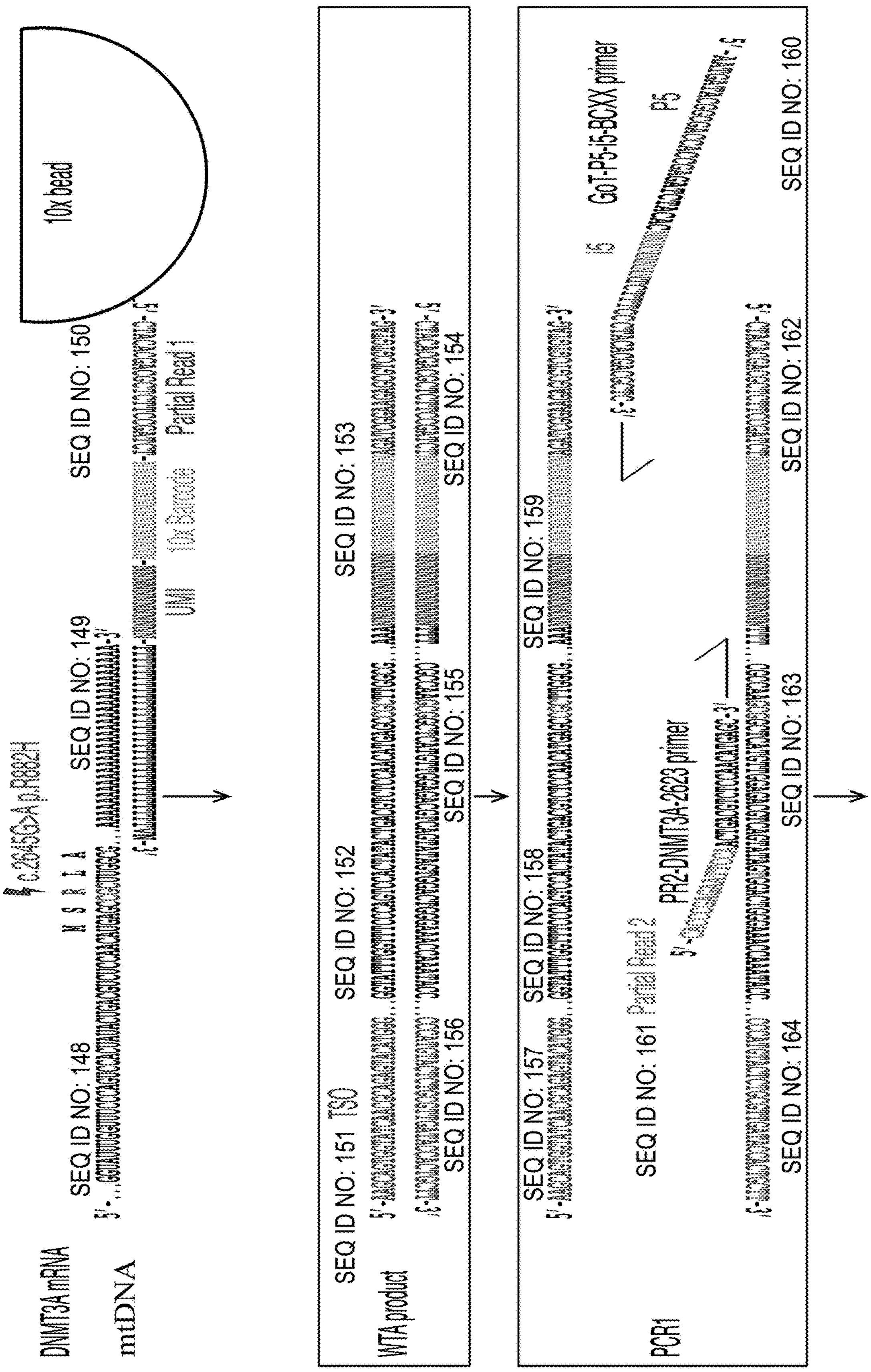
FIG. 21—Enriching transcripts from 10× 3' libraries. Schematic depicts experimental overview for enriching mitochondrial transcripts using 10× beads.
Figure 21:
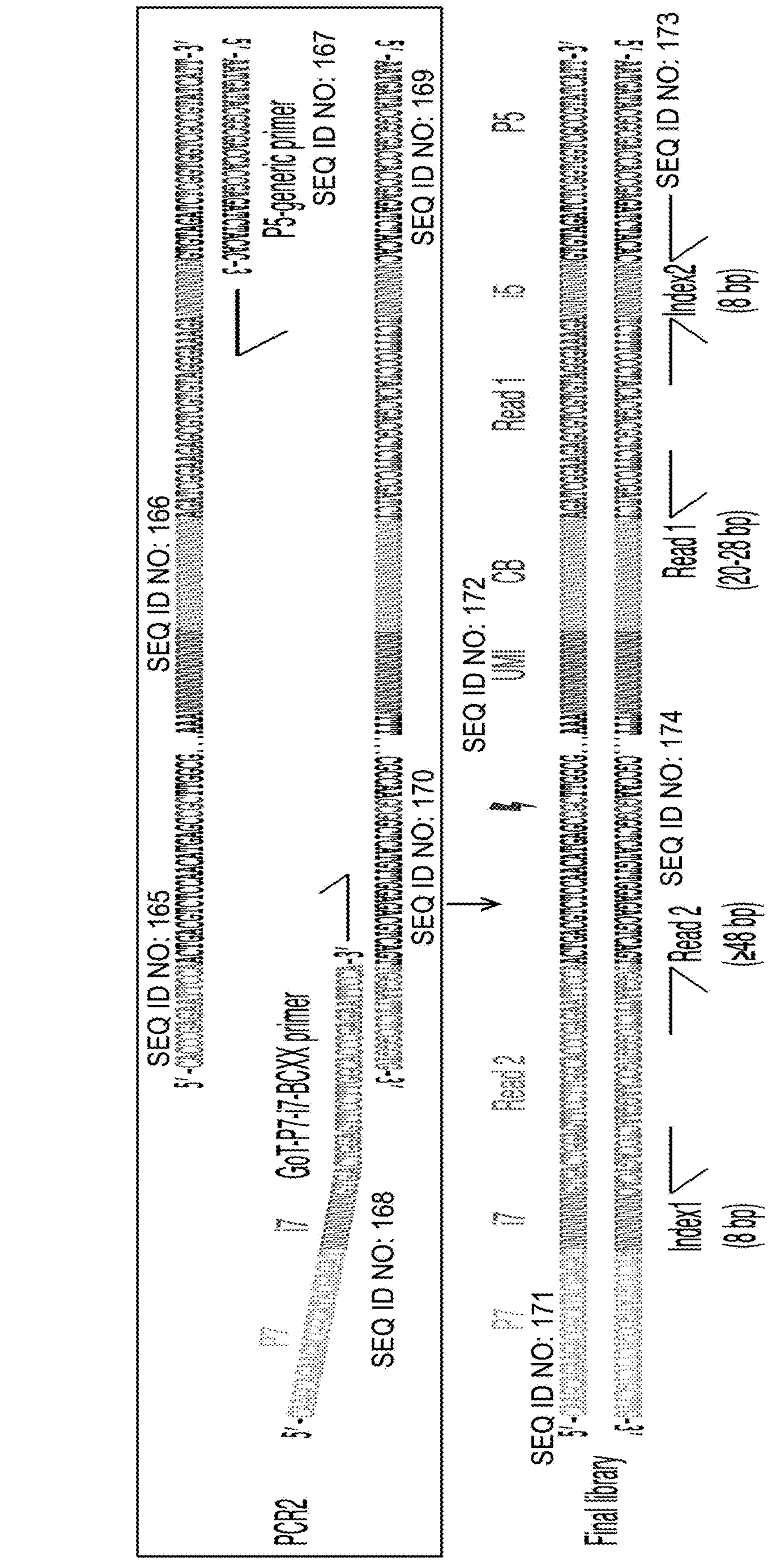

The methods described herein are adaptable for 10× single cell sequencing. FIG. 21 describes an embodiment of how to use 10× libraries. The method is partially based on Nam et al., 2019 (Somatic mutations and cell identity linked by Genotyping of Transcriptomes. Nature. 2019 July; 571 (7765): 355-360). Instead of genomic targets, Applicants target mitochondrial transcripts. Applicants included an i5 library barcode to the P5 side of the fragment (Table 2). This can substantially reduce a technical artifact that occurs on Illumina machines with patterned flow cells, which causes Read2 cDNA sequences to be linked to the wrong Read1 cell barcode sequences.

The cycle number for Read 1 can adjusted based on the technology used: 20 bp for Seq-Well (12 bp CB, 8 bp UMI), 26 bp for 10× v2 (16 bp CB, 10 bp UMI), and 28 bp for 10× v3 (16 bp CB, 12 bp UMI).

For the Second index (15): Not an option when using 10× 17 Multiplex Kit, product 120262. It is read from the “inside” on the NextSeq and read from the P5 side on the NovaSeq. This index will work on the NovaSeq, MiSeq & HiSeq 2000/2500, but requires a custom spike-in on the MiniSeq, NextSeq & HiSeq 3000/4000 (10×-Ci5P, 5'-AGATCGGAAGAGCGTCGTGTAGGGAAAGA-3' (SEQ ID NO: 147).

The Read 2 length depends on the Illumina instrument and kit used and can be up to 300 cycles on NovaSeq.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of determining a lineage and/or clonal structure of single cells in a multicellular eukaryotic organism, comprising:

a) enriching mitochondrial cDNA from a barcoded single cell cDNA library derived from transcripts obtained from single cells from a subject, wherein enriching mitochondrial cDNA comprises amplification with at least 4 primers each targeting different transcripts, wherein the at least 4 primers comprises:

i) a primer targeting the MT-RNR2 transcript, ii) a primer targeting the MT-CO1 transcript, iii) a primer targeting the MT-ND4 transcript, and iv) a primer targeting the MT-ND5 transcript, wherein the cDNA comprises a cell barcode that identifies the cell of origin for the transcripts and a UMI that identifies each individual transcript;

b) detecting somatic mutations in sequencing reads of the enriched mitochondrial cDNA; and c) clustering the single cells based on the presence of the mutations in mitochondria in the single cells, whereby a lineage and/or clonal structure for the single cells is retrospectively inferred.

2. The method of claim 1, wherein the cDNA library is generated by whole transcriptome amplification (WTA); and/or wherein the method further comprises enriching nuclear cDNA from the barcoded single cell cDNA library; and determining somatic nuclear mutations in the clustered cells, thereby determining somatic nuclear mutations in the lineage and/or clonal structure; and/or wherein the method further comprises generating an RNA-seq library from the barcoded single cell cDNA library; and determining the transcriptome of the clustered cells, thereby determining cell transcriptional states in the lineage and/or clonal structure; and/or wherein somatic nuclear mutations and cell transcriptional states are determined in the lineage and/or clonal structure; and/or wherein enriching cDNA comprises PCR amplification, wherein the PCRs s comprise a binding moiety and the method further comprises enriching for the target cDNA with a solid support specific for the binding moiety, wherein the binding moiety is biotin and the solid support is streptavidin; and/or wherein the PCR primers comprise a binding moiety and the method further comprises enriching for the target cDNA with a solid support specific for the binding moiety, wherein the binding moiety is biotin and the solid support is streptavidin; and/or wherein the cDNA is flanked by sequencing adaptors at the 5' and 3' ends; and/or wherein enriching comprises hybridization of cDNA molecules to oligonucleotides specific for target transcript sequences; and separating the oligonucleotides hybridized to the target transcript sequences from the library.

3. The method of claim 2, wherein heritable cell states are identified; and/or wherein the establishment of a cell state along a lineage is identified.

4. The method of claim 1, wherein enriching and detecting mutations comprises:

a) amplifying each cDNA in the library to create a first PCR product using a tagged 5' primer comprising a binding site for a second PCR product and a sequence complementary to a specific gene of interest and a 3' primer complementary to the adapter sequence at the 3' end of the cDNA, thereby generating a first PCR product;

b) selectively enriching the first PCR product by binding to the tag introduced by the 5' primer or a targeted 3' capture with a bifunctional bead or targeted capture bead;

c) amplifying the tag-enriched first PCR product with a 5' primer comprising the binding site for the second PCR product and a 3' primer complementary to the adapter sequence at the 3' end of the cDNA, thereby generating a second PCR product;

d) amplifying the second PCR product with a 5' primer comprising the binding site for a third PCR product and a 3' primer complementary to the adapter sequence at the 3' end of the cDNA, thereby generating the third PCR product; and e) detecting somatic mutations, barcodes and UMIs in single sequencing reads of the enriched cDNA.

5. The method of claim 4, wherein the tagged 5' primer comprises a biotin tag; and/or wherein the tagged 5' primer and the 3' primer further comprise Uracil DNA glycosylase (UDG) and the DNA glycosylase-lyase Endonuclease VIII recognition sites, thereby generating a first PCR product comprising a sequence targetable by an excision enzyme, and the method further comprises:

a) treating the first PCR product with a mixture of Uracil DNA glycosylase (UDG) and the DNA glycosylase-lyase Endonuclease VIII;

b) circularizing the first PCR product by sticky end ligation; and c) amplifying the tag-enriched circularized PCR product with a 5' primer complementary to gene of interest and having a sequence adapter and a 3' primer having a poly A tail and another sequence adapter thereby generating the second PCR product.

6. The method of claim 1, wherein the single cells are obtained from a tissue, wherein the tissue is associated with a disease state, thereby determining the lineage of the tissue associated with the disease and/or phylogeny of cell lineages for the tissue, wherein the disease is a degenerative disease; or wherein the tissue is healthy tissue; or wherein the tissue is diseased tissue.

7. The method of claim 6, wherein the tissue is a tumor sample, thereby determining clonal populations of cells in a tumor sample, wherein the clonal structure of tumor cells is determined; and/or wherein the clonal structure of tumor infiltrating immune cells is determined, wherein the immune cells are selected from the group consisting of T cells, B cells, macrophages, neutrophils, dendritic cells, megakaryocytes, monocytes, basophils, and eosinophils; and/or wherein the tumor sample is obtained before cancer treatment, and obtaining a tumor sample after treatment and comparing the presence of clonal populations before and after treatment, wherein clonal populations of cells sensitive and resistant to the treatment are identified, wherein the cancer treatment comprises chemotherapy, radiation therapy, immunotherapy, targeted therapy, or a combination thereof.

8. The method of claim 6, wherein the tissue comprises immune cells, thereby determining the clonal relatedness of immune cells, wherein the immune cells are of the myeloid or lymphoid lineage, wherein mitochondrial mutations associated with the bone marrow or tissue are detected in the myeloid cells, thereby determining whether the myeloid cells are derived from the bone marrow or are tissue-resident; or wherein a lineage and/or clonal structure is determined for T cells, thereby determining the clonal relatedness of the T cells, wherein the T cells are obtained from a subject undergoing an immune response.

9. The method of claim 1, wherein the cells obtained from a subject are selected for a cell type, wherein stem and progenitor cells are selected, wherein CD34+ hematopoietic stem and progenitor cells are selected; or wherein peripheral blood mononuclear cells (PBMCs) and/or bone marrow mononuclear cells (BMMCs) are selected, wherein PBMCs and/or BMMCs are selected before and after stem cell transplantation in a subject.

10. The method of claim 1, further comprising determining a lineage and/or clonal structure for single cells from two or more tissues.

11. The method of claim 1, wherein a lineage and/or clonal structure is determined for cells obtained from an in vivo model of cancer before, during, or after induction of cancer, wherein the cells comprise pre-malignant stem cells.

12. The method of claim 1, wherein the somatic mutations detected are detected in at least 5 sequencing reads and have at least 0.5% heteroplasmy in the single cells obtained from the subject, wherein the mutations have at least 5% heteroplasmy in the single cells obtained from the subject; and/or wherein the method further comprises sequencing mitochondrial genomes in a bulk sample obtained from the subject, preferably, wherein the bulk sequencing comprises ATAC-seq, DNA-seq, RNA-seq, or RCA-seq; and/or wherein the somatic mutations detected are detected in at least 5 sequencing reads and have at least 0.5% heteroplasmy in a bulk sample obtained from the subject, preferably, wherein the bulk sequencing comprises ATAC-seq, DNA-seq, RNA-seq, or RCA-seq; and/or wherein the mutations are detected in the D loop of the mitochondrial genomes; and/or wherein the detected mitochondrial mutations have a Phred quality score greater than 20;

and/or wherein the clustering is hierarchical clustering; and/or wherein the method further comprises generating a lineage map; and/or wherein nuclei isolated from the single cells are used; and/or wherein the method further comprises excluding RNA modifications, RNA transcription errors and/or RNA sequencing errors from the mutations detected; and/or wherein the subject is a mammal.

13. The method of claim 12, wherein DNA-seq comprises whole genome, whole exome or targeted sequencing.

14. The method of claim 12, wherein nuclei are isolated from frozen tissue samples, preferably, wherein nuclei are isolated under conditions that enhance recovery of mitochondria; and/or wherein single cells are lysed under conditions that release mitochondrial transcripts, preferably, wherein the lysing conditions comprise one or more of NP-40, Triton X-100, SDS, guanidine isothiocyante, guanidine hydrochloride or guanidine thiocyanate.

15. The method of claim 12, wherein the RNA modifications comprise previously identified RNA modifications; and/or wherein RNA modifications, RNA transcription errors and/or RNA sequencing errors are determined by comparing the mutations detected in the cDNA library to mutations detected by DNA-seq, ATAC-seq or RCA-seq in a bulk sample from the subject.

16. The method of claim 1, wherein the primer targeting the MT-RNR2 transcript is selected from the group consisting of: SEQ ID NOs: 5-11, 68, and 69;

wherein the primer targeting the MT-CO1 transcript is selected from the group consisting of: SEQ ID NOs: 21-27, 72, and 73;

wherein the primer targeting the MT-ND4 transcript is selected from the group consisting of: SEQ ID NOs: 42-48 and 76; and wherein the primer targeting the MT-ND5 transcript is selected from the group consisting of: SEQ ID NOs: 49-56.

17. A method of identifying a cancer therapeutic target comprising:

a) detecting clonal populations of cells in a tumor sample according to claim 1;

b) identifying differential cell states between the clonal populations, wherein the cell state is a differentially expressed gene, differentially expressed gene signature, or a differentially accessible chromatin loci; and c) identifying a cell state present in resistant clonal populations, thereby identifying a therapeutic target.

18. A method of treatment comprising administering a treatment targeting a differentially expressed gene, differentially expressed gene signature, or a differentially accessible chromatin loci, wherein the method comprises identifying a cancer therapeutic target according to claim 17, and administering the treatment to a subject in need thereof.

19. A method of screening for a cancer treatment, comprising:

a) growing a tumor sample obtained from a subject in need thereof;

b) determining clonal populations in the tumor sample according to claim 1;

c) treating the tumor sample with one or more agents;

d) determining the effect of the one or more agents on the clonal populations; and e) identifying differential cell states between sensitive and resistant clonal populations.

20. The method of claim 19, wherein the tumor sample is grown in vitro; or wherein the tumor sample is grown in vivo; or wherein the tumor sample is grown as a patient derived xenograft (PDX).

21. A method of identifying changes in clonal populations having a cell state between healthy and diseased tissue comprising determining clonal populations of cells having a cell state in healthy and diseased cells according to claim 1; and comparing the clonal populations.

* * * * *